United States Patent
Lin et al.

(10) Patent No.: US 10,550,379 B2
(45) Date of Patent: Feb. 4, 2020

(54) DEGRON FUSION CONSTRUCTS AND METHODS FOR CONTROLLING PROTEIN PRODUCTION

(71) Applicant: THE BOARD OF TRUSTEES OF THE LELAND STANFORD JUNIOR UNIVERSITY, Stanford, CA (US)

(72) Inventors: Michael Z. Lin, Stanford, CA (US); Hokyung Chung, Mountain View, CA (US); Conor Jacobs, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/737,712

(22) PCT Filed: Jun. 28, 2016

(86) PCT No.: PCT/US2016/039792
§ 371 (c)(1),
(2) Date: Dec. 18, 2017

(87) PCT Pub. No.: WO2017/004022
PCT Pub. Date: Jan. 5, 2017

(65) Prior Publication Data
US 2018/0179509 A1 Jun. 28, 2018

Related U.S. Application Data

(60) Provisional application No. 62/186,339, filed on Jun. 29, 2015.

(51) Int. Cl.
*C12N 9/50* (2006.01)
*C12N 15/86* (2006.01)
*G01N 33/68* (2006.01)

(52) U.S. Cl.
CPC ............. *C12N 9/506* (2013.01); *C12N 15/86* (2013.01); *C12Y 304/21098* (2013.01);
(Continued)

(58) Field of Classification Search
None
See application file for complete search history.

(56) References Cited

U.S. PATENT DOCUMENTS

| | | | |
|---|---|---|---|
| 6,210,962 B1 | 4/2001 | Brechot et al. | |
| 2009/0074803 A1* | 3/2009 | Sallberg | A61K 39/29 424/186.1 |
| 2010/0041092 A1 | 2/2010 | Lin et al. | |

FOREIGN PATENT DOCUMENTS

| | | |
|---|---|---|
| GB | 2212511 | 7/1989 |
| WO | 1989/04669 | 6/1989 |

OTHER PUBLICATIONS

Banaszynski et al. (2006) "A Rapid, Reversible, and Tunable Method to Regulate Protein Function in Living Cells Using Synthetic Small Molecules" Cell, Cell Press, 126(5):995-1004.
(Continued)

*Primary Examiner* — Addison D Ault
(74) *Attorney, Agent, or Firm* — Brian E. Davy; Bozicevic, Field & Francis LLP

(57) ABSTRACT

Engineered fusion proteins comprising a self-excising degron for controlling protein production are disclosed. In particular, the inventors have constructed fusion proteins comprising a degron connected to a protein of interest through a cleavable linker comprising a hepatitis C virus (HCV) protease site. The degron can be removed from the protein of interest by a czs-encoded HCV protease such that the protein of interest can be produced with minimal structural modification. Clinically available HCV protease inhibitors can be used to block protease cleavage such that the degron is retained after inhibitor addition on subsequently synthesized protein copies. The degron when attached causes rapid degradation of the linked protein. Such fusions
(Continued)

of a degron to a protein of interest will be especially useful when control over protein production with minimal structural modification is desired.

40 Claims, 41 Drawing Sheets

Specification includes a Sequence Listing.

(52) U.S. Cl.
CPC ......... *G01N 33/68* (2013.01); *C07K 2319/50* (2013.01); *C07K 2319/95* (2013.01); *C12N 2760/18443* (2013.01)

(56) References Cited

OTHER PUBLICATIONS

Chung et al. (2015) "Tunable and reversible drug control of protein production via a self-excising degron" Nature Chem. Biol., 11(9):713-720.

Database UniProt (2014) Accession No. U5Y7Q5, 2pgs.

Hannah et al. (2015) "A small-molecule SMASh hit: Methods" Nature Chem. Biol., 11(9):637-638.

Hokyung et al. (2014) "Control of Protein Production and Virus Replication by Pharmacological Blockade of Degron Detachment" Protein Science, 23:171-172.

Iwamoto et al. (2010) "A General Chemical Method to Regulate Protein Stability in the Mammalian Central Nervous System" Chem. and Biol., 17(9):981-988.

Lienert et al. (2014) "Synthetic biology in mammalian cells: next generation research tools and therapeutics" Nature Reviews Molecular Cell Biology, 15(2):95-107.

Thibeault et al. (2009) "Use of the fused NS4A Peptide-NS3 protease domain to study the importance of the helicase domain for protease inhibitor binding to hepatitis C virus N3-NS4A" Biochem. Am. Chem. Soc., 48(4):744-753.

House, Colin S., et al., "Elucidation of the Substrate Binding Site of Siah Ubiquitin Ligase," Structure (2006) 14 (4):695-701.

* cited by examiner

DEMEEECSQHLPGAGSSGDIMDYKDDDDKGSSGTGSGSGTSAPITAYAQQTRGLLGCIITSLTG
―――――――――△――――――――― ――――――   ―――――――――――△――――――――――――――――
     cleavage site       Flag tag            NS3 protease              α0 helix

RDKNQVEGEVQIVSTATQTFLATCINGVCWAVYHGAGTRTIASPKGPVIQMYTNVDQDLVGWP

APQGSRSLLTPCTCGSSDLYLVTRHADVIPVRRRGDSRGSLLSPRPISYLKGSSGGPLLCPAGH
                                                        NS3 helicase AVGLFRAAVCTRGVAKAVDFIPVENLETTMRSPVFTDNSSPPAVTLTHPITKIDTKYIMTCMS
                                                     ―――――△――――――――
                                                     helicase domain deletion ADLEVVTSTWVLVGGVLAALAAYCLSTGCVVIVGRIVLSGKPATIPDREVLY
·····―――――――――――― ·············
 NS4A   TM helix              β-strand

FIG. 1B

MDYKDDDDKGSSGTGSGSGTSAPITAYAQQTRGLLGCIITSLTGRDKNQVEGEVQIVSTATQT
_Flag tag_   NS3 protease

FLATCINGVCWAVYHGAGTRTIASPKGPVIQMYTNVDQDLVGWPAPQGSRSLTPCTCGSSDLY

LVTRHADVIPVRRRGDSRGSLLSPRPISYLKGSSGGPLLCPAGHAVGLFRAAVCTRGVAKAVD
NS3 helicase                                                 NS4A FIPVENLETTMRSPVFTDNSSPPAVTLTHPITKIDTKYIMTCMSADLEVVTSTWVLVGGVLAA
                        helicase domain deletion

LAAYCLSTGCVVIVGRI

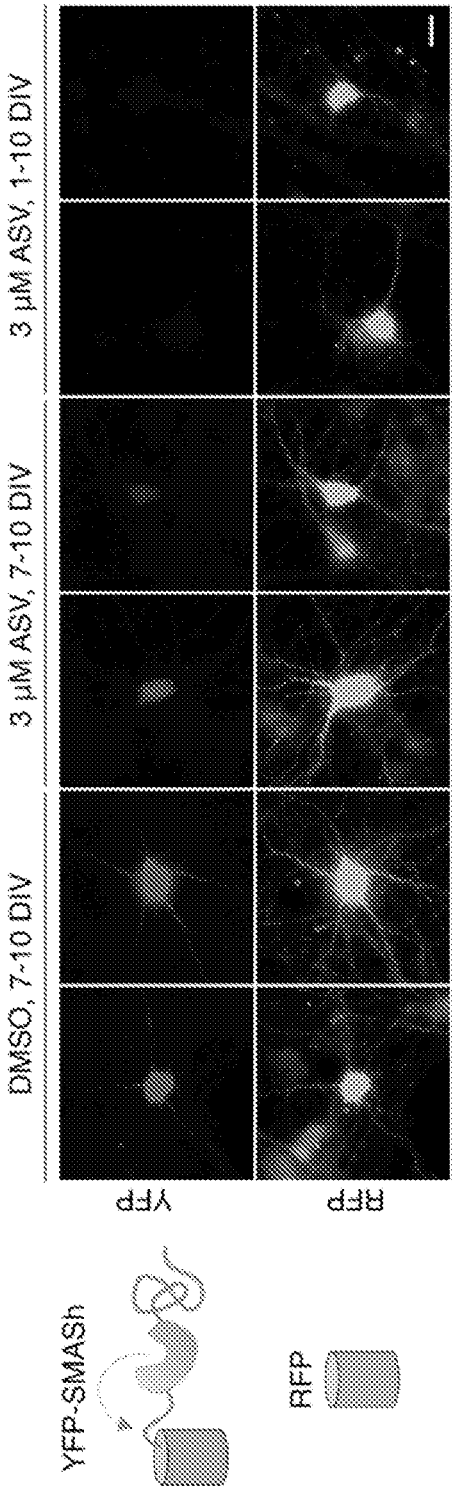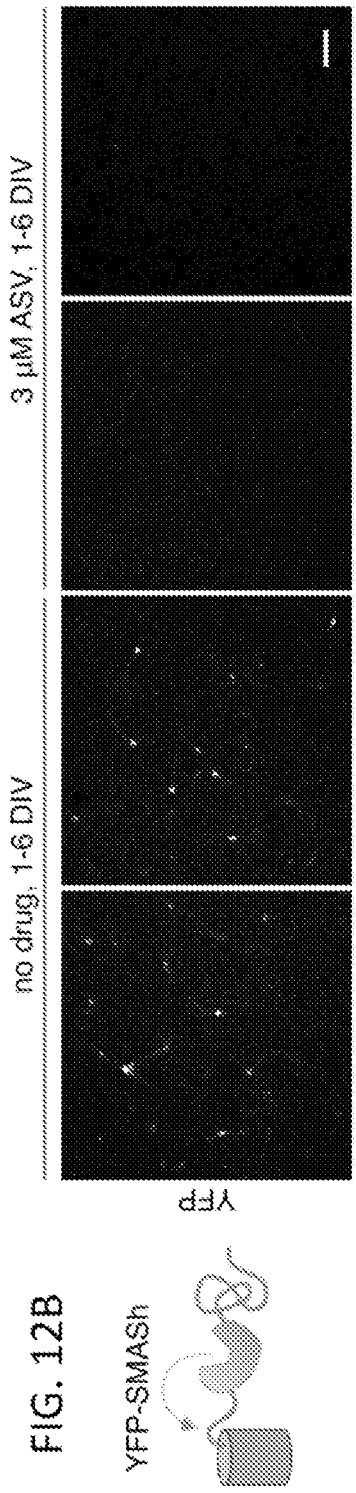
FIG. 12A
FIG. 12B

DEGRON FUSION CONSTRUCTS AND METHODS FOR CONTROLLING PROTEIN PRODUCTION

STATEMENT REGARDING FEDERALLY SPONSORED RESEARCH OR DEVELOPMENT

This invention was made with Government support under contract GM098734 awarded by the National Institutes of Health. The Government has certain rights in the invention.

TECHNICAL FIELD

The present invention pertains generally to the field of protein engineering and methods of controlling the production of proteins. In particular, the invention relates to engineered fusion proteins comprising a degron fused to a polypeptide of interest through a cleavable linker comprising a protease site whose cleavage can be inhibited with a protease inhibitor such that degradation of the polypeptide of interest is controllable.

BACKGROUND

Technology for rapidly shutting off the production of specific proteins in eukaryotes would be of widespread utility as a research tool and for gene or cell therapy applications, but a simple and effective method has yet to be developed. Controlling protein production through repression of transcription is slow in onset, as existing mRNA molecules continue to be translated into proteins after transcriptional inhibition. RNA interference (RNAi) directly induces mRNA destruction, but RNAi is often only partially effective and can exhibit both sequence-independent and sequence-dependent off-target effects (Sigoillot et al. (2011) ACS Chem Biol 6:47-60). Furthermore, mRNA and protein abundance are not always correlated due to regulation of the translation rate of specific mRNAs (Vogel et al. (2012) Nat Rev Genet 13:227-232; Wu et al. (2013) Nature 499:79-82; Battle et al. (2015) Science 347:664-667). Lastly, both transcriptional repression and RNAi take days to reverse (Liu et al. (2008) J Gene Med 10:583-592; Matsukura et al. (2003) Nucleic Acids Res 31:e77).

Thus, there remains a need for a simple to use system for controlling protein production.

SUMMARY

The invention relates to degron fusion constructs and methods of using them for controlling protein production. In particular, the inventors have constructed fusion proteins containing a degron fused to a polypeptide of interest through a cleavable linker comprising a protease site whose cleavage can be inhibited with a protease inhibitor such that degradation of the polypeptide of interest is controllable.

In one aspect, the invention includes a degron comprising the amino acid sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the degron is capable of promoting degradation of a polypeptide.

In another aspect, the invention includes a degron fusion protein comprising: a) a polypeptide of interest; b) a degron, wherein the degron is operably linked to the polypeptide of interest when the fusion protein is in an uncleaved state, such that the degron promotes degradation of the polypeptide of interest in a cell; c) a protease, wherein the protease can be inhibited by contacting the fusion protein with a protease inhibitor; and c) a cleavable linker that is located between the polypeptide of interest and the degron, wherein the cleavable linker comprises a cleavage site recognized by the protease, wherein cleavage of the cleavable linker by the protease releases the polypeptide of interest from the fusion protein, such that when the fusion protein is in a cleaved state, the degron no longer controls degradation of the polypeptide of interest.

In certain embodiments, the fusion protein comprises a degron comprising the amino acid sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the degron is capable of promoting degradation of the polypeptide of interest when the fusion protein is in an uncleaved state.

In certain embodiments, the protease contained in the fusion protein is a hepatitis C virus (HCV) nonstructural protein 3 (NS3) protease, and the cleavable linker of the fusion protein comprises an NS3 protease cleavage site. Exemplary NS3 protease cleavage sites include the HCV polyprotein NS3/NS4A, NS4A/NS4B, NS4B/NS5A, and NS5A/NS5B junction cleavage sites.

The degron may be linked to the C-terminus of the polypeptide of interest in the fusion protein. In certain embodiments, the fusion protein comprises components arranged from N-terminus to C-terminus in the uncleaved state as follows: a) the polypeptide of interest, b) the cleavable linker, c) the protease, and d) the degron. In one embodiment, the fusion protein comprises a polypeptide comprising the amino acid sequence of SEQ ID NO:7, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the polypeptide comprises a biologically active degron capable of promoting degradation of the polypeptide of interest and a protease capable of cleaving the fusion protein at the cleavage site, wherein the polypeptide is linked to the C-terminus of the polypeptide of interest.

Alternatively, the degron may be linked to the N-terminus of the polypeptide of interest in the fusion protein. In certain embodiments, the fusion protein comprises components arranged from N-terminus to C-terminus in the uncleaved state as follows: a) the protease, b) the degron, c) the cleavable linker, and c) the polypeptide of interest. In one embodiment, the fusion protein comprises a polypeptide comprising the amino acid sequence of SEQ ID NO:8, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the polypeptide comprises a biologically active degron capable of promoting degradation of the polypeptide of interest and a protease capable of cleaving the fusion protein at the cleavage site, wherein the polypeptide is linked to the N-terminus of the polypeptide of interest.

In certain embodiments, the fusion protein further comprises a targeting sequence. Exemplary targeting sequences includes a secretory protein signal sequence, a membrane protein signal sequence, a nuclear localization sequence, a nucleolar localization signal sequence, an endoplasmic reticulum localization sequence, a peroxisome localization sequence, a mitochondrial localization sequence, and a protein binding motif sequence.

In certain embodiments, the fusion protein further comprises a tag. Exemplary tags include a His-tag, a Strep-tag, a TAP-tag, an S-tag, an SBP-tag, an Arg-tag, a calmodulin-binding peptide tag, a cellulose-binding domain tag, a DsbA tag, a c-myc tag, a glutathione S-transferase tag, a FLAG tag, a HAT-tag, a maltose-binding protein tag, a NusA tag, and a thioredoxin tag.

In certain embodiments, the fusion protein further comprises a detectable label. The detectable label may comprise any molecule capable of detection. For example, the detectable label may be a fluorescent, bioluminescent, chemiluminescent, colorimetric, or isotopic label. In certain embodiments, the detectable label is a fluorescent protein or bioluminescent protein.

In certain embodiments, the polypeptide of interest in the degron fusion protein is a membrane protein, a receptor, a hormone, a transport protein, a transcription factor, a cytoskeletal protein, an extracellular matrix protein, a signal-transduction protein, an enzyme, or any other protein of interest. The polypeptide of interest may comprise an entire protein, or a biologically active domain (e.g., a catalytic domain, a ligand binding domain, or a protein-protein interaction domain), or a polypeptide fragment of a selected protein of interest.

In another aspect, the invention includes a polynucleotide encoding a degron fusion protein described herein. In one embodiment, the polynucleotide is a recombinant polynucleotide comprising a polynucleotide encoding a degron fusion protein operably linked to a promoter. The recombinant polynucleotide may comprise an expression vector, for example, a bacterial plasmid vector or a viral expression vector. Exemplary viral vectors include measles virus, vesicular stomatitis virus, adenovirus, retrovirus (e.g., γ-retrovirus and lentivirus), poxvirus, adeno-associated virus, baculovirus, or herpes simplex virus vectors.

In certain embodiments, the recombinant polynucleotide comprises a polynucleotide encoding a fusion protein comprising a sequence selected from the group consisting of SEQ ID NO:7 and SEQ ID NO:8, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fusion protein comprises a degron operably linked to a polypeptide of interest, which is capable of promoting degradation of the polypeptide of interest, and a protease capable of cleaving the fusion protein at a cleavage site.

In another aspect, the invention includes a host cell comprising a recombinant polynucleotide encoding a degron fusion protein operably linked to a promoter. In one embodiment, the host cell is a eukaryotic cell. In another embodiment, the host cell is a mammalian cell. In certain embodiments, the host cell is a stem cell (e.g., embryonic stem cell or adult stem cell). Host cells may be cultured as unicellular or multicellular entities (e.g., tissue, organs, or organoids comprising the recombinant vector). The promoter may be an endogenous or exogenous promoter. In certain embodiments, the recombinant polynucleotide encoding the degron fusion protein resides on an extrachromosomal plasmid or vector. In other embodiments, the recombinant polynucleotide encoding the degron fusion protein is integrated into the cellular genome. For example, the recombinant polynucleotide may integrate into the cellular genome at a position where the polynucleotide sequence encoding the fusion protein is operably linked to an endogenous promoter of a gene.

In another embodiment, the invention includes a descendant of the host cell, wherein the descendant has inherited a recombinant polynucleotide encoding the degron fusion protein.

In another embodiment, the invention includes an organoid comprising a recombinant polynucleotide encoding a degron fusion protein operably linked to a promoter. The promoter may be an endogenous or exogenous promoter. In certain embodiments, the recombinant polynucleotide encoding the degron fusion protein resides on an extrachromosomal plasmid or vector. In other embodiments, the recombinant polynucleotide encoding the degron fusion protein is integrated into the organoid genome. For example, the recombinant polynucleotide may integrate into the organoid genome at a position where the polynucleotide sequence encoding the fusion protein is operably linked to an endogenous promoter of a gene.

In another embodiment, the invention includes a recombinant animal comprising a recombinant polynucleotide encoding a degron fusion protein operably linked to a promoter. The promoter may be an endogenous or exogenous promoter. In certain embodiments, the recombinant polynucleotide encoding the degron fusion protein resides on an extrachromosomal plasmid or vector. In other embodiments, the recombinant polynucleotide encoding the degron fusion protein is integrated into the genome of the recombinant animal. For example, the recombinant polynucleotide may integrate into the genome at a position where the polynucleotide sequence encoding the fusion protein is operably linked to an endogenous promoter of a gene.

In another embodiment, the invention includes a descendant of the recombinant animal, wherein the descendant has inherited the recombinant polynucleotide encoding the degron fusion protein.

In another aspect, the invention includes a method for producing a degron fusion protein, the method comprising: transforming a host cell with a recombinant polynucleotide encoding the fusion protein operably linked to a promoter; culturing the transformed host cell under conditions whereby the fusion protein is expressed; and isolating the fusion protein from the host cell.

In another aspect, the invention includes a method for controlling production of a polypeptide of interest, the method comprising: a) transforming a host cell with a recombinant polynucleotide encoding a degron fusion protein described herein; b) culturing the transformed host cell under conditions whereby the fusion protein is expressed; and c) contacting the cell with a protease inhibitor that inhibits the protease of the fusion protein when production of the polypeptide of interest is no longer desired. The protease inhibitor can be removed when resuming production of the polypeptide of interest is desired.

The recombinant polynucleotide encoding the degron fusion protein preferably is capable of providing efficient production of the polypeptide of interest with biological activity comparable to the wild-type polypeptide. Additionally, production of the polypeptide of interest from the recombinant polynucleotide preferably can be rapidly and nearly completely suppressed in the presence of a protease inhibitor. For example, a protease inhibitor may reduce production of the polypeptide of interest by at least 80%, 90%, or 100%, or any amount in between as compared to levels of the polypeptide in the absence of the protease inhibitor. In certain embodiments, production of the polypeptide of interest by the recombinant polynucleotide in the host cell in the presence of the protease inhibitor is at least about 90% to 100% suppressed, including any percent identity within this range, such as 90, 91, 92, 93, 94, 95, 96, 97, 98, or 99%.

In certain embodiments, the fusion protein used for controlling production of a polypeptide of interest comprises an HCV NS3 protease. NS3 protease inhibitors that can be used in the practice of the invention include, but are not limited to, simeprevir, danoprevir, asunaprevir, ciluprevir, boceprevir, sovaprevir, paritaprevir and telaprevir.

In another aspect, the invention includes a method for controlling production of a polypeptide of interest in a subject, the method comprising: a) administering a recombinant polynucleotide encoding a degron fusion protein to the subject, such that the fusion protein is expressed in the subject; and b) administering a protease inhibitor that inhibits the protease of the fusion protein to the subject when production of the polypeptide of interest is not desired. The method may further comprise ceasing administration of the protease inhibitor when resuming production of the polypeptide of interest in the subject is desired. The recombinant polynucleotide may comprise an expression vector, for example, a viral expression vector, such as, but not limited to, an adenovirus, retrovirus (e.g., γ-retrovirus and lentivirus), poxvirus, adeno-associated virus, baculovirus, or herpes simplex virus vector. In one embodiment, the recombinant polynucleotide comprises a polynucleotide sequence encoding the fusion protein operably linked to an exogenous promoter. In another embodiment, the recombinant polynucleotide is integrated into the genome of the subject. For example, the recombinant polynucleotide may integrate into the genome at a position where the polynucleotide sequence encoding the fusion protein is operably linked to an endogenous promoter of a gene in the subject.

In another aspect, the invention includes a method for controlling production of a polypeptide of interest in a recombinant animal, the method comprising: a) administering a recombinant polynucleotide encoding a degron fusion protein to the recombinant animal, such that the fusion protein is expressed in the recombinant animal and b) administering a protease inhibitor that inhibits the protease of the fusion protein to the recombinant animal when production of the polypeptide of interest is not desired.

In another aspect, the invention includes a method of controlling production of a polypeptide of interest in an organoid, the method comprising: a) introducing a recombinant polynucleotide encoding the fusion protein of claim 4 into an organoid; b) culturing the organoid under conditions whereby the fusion protein is produced in the organoid; and c) contacting the organoid with a protease inhibitor that inhibits the protease of the fusion protein when production of the polypeptide of interest is no longer desired.

In another aspect, the invention includes a method of measuring the turnover of a polypeptide of interest, the method comprising: a) introducing a recombinant polynucleotide encoding a degron fusion protein described herein into a cell; b) measuring amounts of the polypeptide of interest in the cell before and after contacting the cell with a protease inhibitor that inhibits the protease of the fusion protein; and c) calculating the turnover of the polypeptide of interest based on the amounts of the polypeptide of interest in the cell before and after adding the protease inhibitor. Additionally, the half-life of the polypeptide of interest in the cell can be calculated. The amount of the polypeptide of interest in the cell can be measured either continuously or periodically over a period of time.

In another aspect, the invention includes a conditionally replicating viral vector comprising a modified genome of a virus such that production of a polypeptide required for efficient replication of the virus is controllable, wherein the viral vector comprises a nucleic acid encoding a fusion protein comprising: i) the polypeptide required for efficient replication of the virus; ii) a degron, wherein the degron is operably linked to the polypeptide required for efficient replication of the virus when the fusion protein is in an uncleaved state, such that the degron promotes degradation of the polypeptide in a cell; iii) a protease, wherein the protease can be inhibited by contacting said fusion protein with a protease inhibitor; and iv) a cleavable linker that is located between the polypeptide required for efficient replication of the virus and the degron, wherein the cleavable linker comprises a cleavage site recognized by the protease, wherein cleavage of the cleavable linker by the protease releases the polypeptide required for efficient replication of the virus from the fusion protein, such that when the fusion protein is in a cleaved state, the degron no longer controls degradation of the polypeptide required for efficient replication of the virus. In certain embodiments, the virus is an RNA virus (e.g., measles virus or a vesicular stomatitis virus). In another embodiment, the conditionally replicating viral vector is a plasmid. The viral vector may further comprise a multiple cloning site, transcription promoter, transcription enhancer element, transcription termination signal, polyadenylation sequence, or exogenous nucleic acid, or any combination thereof.

In certain embodiments the conditionally replicating viral vector comprises a modified measles virus genome comprising a nucleic acid encoding a degron fusion protein, wherein the polypeptide required for efficient replication of the virus is a measles virus phosphoprotein. In one embodiment, the conditionally replicating viral vector comprises the nucleotide sequence of SEQ ID NO:9, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein replication of the virus can be inhibited with an HCV NS3 protease inhibitor.

In another aspect, the invention includes a method of controlling production of a virus, the method comprising: a) introducing a conditionally replicating viral vector described herein into a host cell; b) culturing the host cell under conditions suitable for producing the virus; and c) contacting the host cell with a protease inhibitor, such that the polypeptide required for efficient replication of the virus is degraded when production of the virus is no longer desired. The protease inhibitor can be removed when resuming production of the virus is desired.

The conditionally replicating viral vector preferably is capable of providing efficient production of the virus in the host cell in the absence of a protease inhibitor, comparable to the level of the virus produced by the wild-type viral genome. In certain embodiments, the level of the virus produced by the conditionally replicating viral vector in the absence of the protease inhibitor is at least about 30%, 35%, 40%, 45%, 50%, 55%, 60%, 65%, 70%, 75%, 80%, 85%, 90%, 95%, or 100%, or any amount in between as compared to levels of the virus produced by the wild-type viral genome.

Additionally, production of the virus from the conditionally replicating viral vector preferably can be nearly completely suppressed in the presence of a protease inhibitor. For example, a protease inhibitor may reduce production of the virus by 80%, 90%, 100%, or any amount in between as compared to levels of the virus in the absence of the protease inhibitor. In certain embodiments, production of the virus by the conditionally replicating viral vector in the host cell in the presence of the protease inhibitor is at least about 90% to 100% suppressed, including any percent identity within this range, such as 90, 91, 92, 93, 94, 95, 96, 97, 98, or 99%.

In certain embodiments, the conditionally replicating viral vector, used in controlling production of a virus, expresses a degron fusion protein comprising an HCV NS3 protease, wherein addition of an NS3 protease inhibitor can be used to suppress production of the virus. NS3 protease inhibitors that can be used include, but are not limited to, simeprevir, danoprevir, asunaprevir, ciluprevir, boceprevir, sovaprevir, paritaprevir and telaprevir.

In another aspect, the invention includes a recombinant virion comprising a conditionally replicating viral vector described herein.

In another aspect, the invention includes a kit for preparing or using degron fusion proteins according to the methods described herein. Such kits may comprise one or more degron fusion proteins, nucleic acids encoding such fusion proteins, expression vectors, conditionally replicating viral vectors, cells, or other reagents for preparing or using degron fusion proteins, as described herein. The kit may further include a protease inhibitor, such as an HCV NS3 protease inhibitor, including, for example, simeprevir, danoprevir, asunaprevir, ciluprevir, boceprevir, sovaprevir, paritaprevir or telaprevir.

In certain embodiments, the kit comprises a recombinant polynucleotide encoding a degron fusion protein described herein. In one embodiment, the kit comprises a recombinant polynucleotide encoding a fusion protein comprising a sequence selected from the group consisting of SEQ ID NO:7 and SEQ ID NO:8, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fusion protein comprises a degron operably linked to a polypeptide of interest, which is capable of promoting degradation of the polypeptide of interest, and a protease capable of cleaving the fusion protein at a cleavage site.

In other embodiments, the kit comprises a conditionally replicating viral vector as described herein. In one embodiment, the kit comprises a conditionally replicating viral vector comprising the nucleotide sequence of SEQ ID NO:9, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein production of the virus can be inhibited with a protease inhibitor.

These and other embodiments of the subject invention will readily occur to those of skill in the art in view of the disclosure herein.

BRIEF DESCRIPTION OF THE FIGURES

FIGS. 1A-1D show the Small Molecule-Assisted Shutoff (SMASh) concept and development. FIG. 1A illustrates the SMASh concept. FIG. 1A (Top) shows a protein of interest fused to the SMASh tag via a HCV NS3 protease recognition site. After protein folding, the SMASh tag is removed by its internal NS3 protease activity, and is degraded due to an internal degron activity. FIG. 1A (Bottom) shows that addition of a protease inhibitor induces the rapid degradation of subsequently synthesized copies of the tagged protein, effectively shutting off further protein production. FIG. 1B shows the amino acid sequence (SEQ ID NO:7) of the SMASh tag. The NS3 protease sequence (light gray), sequence derived from NS3 helicase (dark gray), and sequence derived from NS4A (light gray) are shown. Secondary structures (α-helices and /β-strands) in the context of the original HCV polyprotein are underlined. The NS4A/4B protease cleavage site is in dark gray, with an arrow indicating the site of cleavage. The degron region is marked with a dotted line. FIG. 1C (Top) shows the organization of fusions of PSD95 with NS3protease (NS3pro) or NS3pro-NS4A, with predicted protein fragment sizes indicated. FIG. 1C (Bottom) shows that for both constructs, PSD95 appears in HEK293 cells 24 hours post-transfection in the absence of the protease inhibitor asunaprevir (ASV) at the expected cleaved size. The PSD95-NS3 pro fusion was expressed at full-length size with asunaprevir, indicating efficient drug-inhibition of cleavage. However, the PSD95-NS3proNS4A fusion failed to exhibit expression with asunaprevir. Locations of size markers are indicated at left. GAPDH serves as a loading control. FIG. 1D shows that a specific element in the NS3proNS4A sequence is responsible for degron activity. HeLa cells were transfected to express YFP fused to the NS3pro-NS4A cassette (wt), or to a modified cassette in which the putatively unstructured and hydrophobic stretch derived from NS3helicase and the NS4A α-helix (dotted line in FIG. 1B) was mutated to a GGS-repeat linker of the same length (GGS). Constructs were expressed for 24 hours in either DMSO or 2 µM ASV, and lysates were analyzed by immunoblotting as indicated. Disruption of the hydrophobic region significantly reduced degradation of YFP in the +ASV condition. β-actin served as a loading control.

FIGS. 2A-2C show that proteins can be regulated by SMASh tags at either terminus. FIG. 2A shows the amino acid sequence (SEQ ID NO:8) of the N-terminal SMASh tag. NS3 protease sequence (light gray), sequence derived from NS3 helicase (dark gray), and sequence derived from NS4A (medium gray) are shown. NS5A/5B-based protease substrate site is in dark gray. FIG. 2B shows that SMASh can regulate YFP when fused to either terminus. SMAShYFP and YFP-SMASh were expressed in HEK293 cells in the absence or presence of ASV for 24 hours. Immunoblotting revealed shutoff of YFP expression by ASV for both constructs. DMSO was used as vehicle control. β-actin served as a loading control. FIG. 2C that fluorescence microscopy confirmed shutoff of YFP expression by ASV for both constructs. Scale bar, 50 pm.

FIG. 3A shows a test of dose-dependent regulation of protein expression by SMASh. HEK293 cells transfected with YFP-SMASh were cultured for 24 hours without or with ASV (15 pM to 15 pM) and YFP was detected by immunoblot. GAPDH served as a loading control. FIG. 3B shows quantification of YFP levels by immunoblot. Background-subtracted YFP signal was normalized to background-subtracted GAPDH signal, and then plotted as a percent of the signal in the untreated condition (n=3, error bars represent standard deviations). FIG. 3C shows restoration of YFP expression following drug washout, assayed by immunoblot. HeLa cells transfected with YFP-SMASh were grown 12 hours in the presence of 2 pM ASV, then washed and exchanged into fresh media. Parallel wells were lysed at indicated times afterwards. β-actin served as a loading control. FIG. 3D shows restoration of YFP expression following drug washout, assayed by fluorescence microscopy. HeLa cells cotransfected with untagged RFP and YFP-SMASh were grown 12 hours in the presence of 2 µM ASV, washed, exchanged into fresh media, and imaged at indicated times afterwards. Similarly transfected HeLa cells grown 12 hours in DMSO are shown at left for comparison. Representative images are shown. Scale bar, 20 µm.

FIG. 4A shows that SMASh functions on multimerizing protein, CaMKIIα. TimeSTAMP2-tagged CaMKIIα (T52-CaMKIIα) or SMASh-CaMKIIα were expressed in HEK293 cells for 24 hours in the absence or presence of ASV. TimeSTAMP2 (TS2) tags contain cis-cleaving NS3 protease domains but lack NS4A sequences, verifying that drug inhibition of protein expression is specific to SMASh. Immunoblotting revealed shutoff of CaMKIIα expression by ASV when it was tagged with SMASh but not when it was tagged with TimeSTAMP2. GAPDH served as a loading control. The asterisk indicates a cross-reactive protein also detected in untransfected cells. FIG. 4B shows GluRIIA-CFP fused to TimeSTAMP2 with an orange fluorescent protein readout (GluRIIA-CFP-TS2:OFP) or GluRIIA-CFP-SMASh expressed in HEK293 cells for 24 hours in the absence or presence of ciluprevir (CLV). Immunoblotting revealed shutoff of GluRIIA expression by CLV. The non-degron-containing TS2:OFP tag verified that drug inhibition of protein expression is specific to SMASh. Cross-reactive bands at 80 kDa (asterisk) served as a lysate loading control. FIG. 4C shows CYP21A2 fused to either TimeSTAMP2 or SMASh tested by the same method as in FIG. 4A. The CYP21A2 level was detected by immunoblotting. β-actin served as a loading control.

FIG. 5A shows SMASh-YFP or YFP-SMASh expressed from the strong constitutive GPD promoter in wild-type or drug efflux pump-deficient yeast cells. The yeast cells were cultured in SD media in the absence or presence of ASV for 24 hours. Immunoblotting revealed shutoff of YFP expression by ASV for both constructs. DMSO was used as vehicle control. GAPDH served as a loading control. FIG. 5B shows quantification of YFP levels in the yeast extract by immunoblot. Background-subtracted YFP signal was normalized to background-subtracted GAPDH signal, then plotted as a percent of the signal in the untreated condition (n=3, error bars represent standard deviations). FIG. 5C shows fluorescence images of yeast cultures in (FIG. 5A) showing that the episomally expressed YFP signal is controlled in a drug-dependent manner. Imaging was done in SD media. Scale bar, 10 µm.

FIG. 6A shows that YFP-SMASh under strong GPD promoter is integrated into the yeast chromosomal LUE locus. Recombinant yeast was cultured in SD media in the absence or presence of ASV for 24 hours. Immunoblotting revealed shutoff of YFP expression by ASV. DMSO was used as vehicle control. GAPDH served as a loading control. FIG. 6B shows fluorescence images of yeast cultures in FIG. 6A showing that chromosomally-expressed YFP signal is controlled in a drug-dependent manner. Imaging was done in SD media. Scale bar, 10 FIG. 6C shows results when the HA tag and the SMASh tag were inserted at the C-terminus of the endogenous SEC14 coding sequence. Serial dilutions of cells were plated and incubated for 48 hours at 30° C. and 23° C. in the absence or presence of ASV (3 µM). FIG. 6D shows results when a SMASh tag was inserted at the C-terminus of the endogenous YSH1 coding sequence. Serial dilutions of cells were plated and incubated for 48 hours at 30° C. and 37° C. in the absence or presence of ASV (10 µM).

FIG. 7A shows the concept of controlling MeV replication with P-SMASh. In the absence of the drug, essentially unmodified phosphoprotein (P, dark gray) is released and can successfully form replication complexes with nucleocapsid (N, light gray) and large (L) proteins. FIG. 7B shows genome organization of MeV-EGFP-PSMASh. Scale bar is 1 kilobase. FIG. 7C shows regulation of MeV-EGFP-P-SMASh by a drug. Vero cells infected with MeV-EGFP or MeV-EGFP-P-SMASh at multiplicity of infection (MOI) of 1 were grown for 72 hours in the absence or presence of ASV. Drug inhibited syncytium formation and GFP expression in MeV-EGFP-P-SMASh-infected but not MeV-EGFP-infected cells. Scale bar, 50 FIG. 7D shows the quantification of fluorescence from Vero cells infected with MeV-EGFP-P-SMASh at MOI 1 and 0.1 in the absence or presence of 3 µM ASV (n=3, error bars are standard deviation). FIG. 7E shows that a drug inhibited P expression in MeV-EGFP-P-SMASh-infected but not MeVEGFP-infected cells, as assayed by immunoblotting. GAPDH served as a loading control.

FIG. 8A shows that in the native HCV polyprotein, the non-consensus NS3/4A site is positioned in the active site of NS3 protease by the NS3 helicase domain and cleaved. The hydrophobic N-terminal of NS4A then inserts into the membrane (right). Elements are numbered from N-terminus to C-terminus to clarify order of linkage. FIG. 8B shows that in NS3pro-NS4A, most of NS3 helicase is deleted, so that the C-terminus of NS3 protease is connected to a short C-terminal segment of NS3 helicase followed by NS4A. Removal of the NS3 helicase domain may expose hydrophobic residues in the helicase C-terminus and prevent cleavage at the NS3/4A site, preventing membrane insertion of NS4A. Models were generated using PDB file 1CU1. FIGS. 8C and 8D shows mechanisms of degradation of proteins fused to NS3pro-NS4A. HeLa cells expressed YFP (FIG. 8C) or PSD95 (FIG. 8D) fused to NS3pro-NS4A (wt), or the degron-disrupted mutant (GGS). From 18 to 24 hours post-transfection, cells were treated with ASV (1 µM) and degradation inhibitors (MG, MG132 10 µM; BTZ, bortezomib 66 nM; CHQ, chloroquine 100 µM; BAF, bafilomycin-A1 200 nM). This short time window was used to avoid toxicity by degradation inhibitors. Final DMSO concentration was 0.23% (v/v) for all conditions in (FIG. 8C) and 0.33% for all conditions in (FIG. 8D). The combination of MG132 and chloroquine inhibited degradation of YFP-NS3pro-NS4A or PSD95-NS3pro-NS4A cassette to a degree approaching that of the GGS mutation. β-actin served as a loading control.

FIG. 9A shows that poly-GSS linkers of 6, 12, or 18 amino acids (aa) inserted in NS4A to improve accessibility of C-terminal sites to cis cleavage. Two substrate sequences, NS4A/4B (slow-cleaving) and NS5A/5B (fast-cleaving) were tested. Constructs were expressed in HEK293 cells for 24 hours without or with ASV, and then lysates were immunoblotted for Arc. Increasing linker length from 0 to 6 amino acids reduced off-target cleavage with the NS4A/4B substrate, which may be due to improving its accessibility (lanes 1-8). A 6-aa linker with the NS5A/5B substrate allowed specific cleavage at the desired site without ASV and complete protein suppression with ASV, while suppression was incomplete with an 18-aa linker (lanes 9-12). GAPDH served as a loading control. FIG. 9B shows that SMASh functions at either end of Arc. SMASh-Arc and Arc-SMASh were transiently expressed in HEK293 cells for 24 hours with or without ASV, and then lysates were immunoblotted for Arc. β-actin served as a loading control.

FIG. 10A shows determination of the half-life of PSD95 in HEK293 cells. PSD95-SMASh was expressed in the absence of ASV so that the SMASh tag removed itself for 24 hours, then 1 µM ASV was added to switch production to uncleaved PSD95-SMASh. Levels of cleaved PSD95 over time were then followed by immunoblotting. Background-subtracted PSD95 signal was normalized to background-subtracted β-actin signal and then divided by the mean signal at 0 hour (n=3, error bars represent standard deviations). Values fit an exponential decay function with a half-life of 12.4 hours. FIG. 10B shows that the half-life of PSD95-SMASh can be calculated from the half-life of PSD95 and the ratio of PSD95-SMASh to PSD95 accumulated within the same amount of time, if they are produced at equal rates (see Methods). To obtain this ratio, PSD95-SMASh was first expressed with 1 µM ASV for 24 hours, then ASV was washed out for 4 hours (procedure i). Additional new PSD95 appearing at the cleaved size of 84 kDa was apparent at 28 hours (lane 2). In parallel, PSD95-SMASh was expressed without ASV so that all PSD95-SMASh was cleaved to PSD95 for 24 hours, then new PSD95-SMASh was inhibited from cleavage by addition of 1 µM ASV for 4 hours (procedure ii). The level of PSD95-SMASh (lane 4) was quantified relative to that of PSD95 produced from the same plasmid over the same time (lane 2). Background-subtracted PSD95 and PSD95-SMASh signals were normalized to background-subtracted β-actin signal. To calculate the produced amount of PSD95 and PSD95-SMASh in 4 hours, normalized signals at 24 hours (lanes 1 and 3) were subtracted from those at 28 hours (lanes 2 and 4). With these values inputted into the mathematical model, the half-life of PSD95-SMASh was calculated to be 1.1 hour.

FIG. 11A shows determination of the half-life of CYP21A2 in HEK293 cells. CYP21A2-SMASh was expressed in the absence of ASV so that the SMASh tag removed itself for 24 hours, then 1 µM ASV was added to switch production to uncleaved CYP21A2-SMASh. Levels of cleaved CYP21A2 over time were then followed by immunoblotting. Background-subtracted CYP21A2 signal was normalized to background-subtracted β-actin signal and then divided by the mean signal at 0 hour (n=3, error bars represent standard deviations). Values fit an exponential decay function with a half-life of 130 minutes. FIG. 11B shows that the half-life of CYP21A2-SMASh can be calculated from the half-life of CYP21A2 and the ratio of CYP21A2-SMASh to CYP21A2 accumulated within the same amount of time, if they are produced at equal rates (see Methods). To obtain this ratio, CYP21A2-SMASh was first expressed with 1 µM ASV for 24 hours, then ASV was washed out for 4 hours (procedure i). Additional new CYP21A2 appearing at the cleaved size of 84 kDa was apparent at 28 hours (lane 2). In parallel, CYP21A2-SMASh was expressed without ASV so that all CYP21A2-SMASh was cleaved to CYP21A2 for 24 hours, then new CYP21A2-SMASh was inhibited from cleavage by addition of 1 µM ASV for 4 hours (procedure ii). The level of CYP21A2-SMASh (lane 4) was quantified relative to that of CYP21A2 produced from the same plasmid over the same time (lane 2). Background-subtracted CYP21A2 and CYP21A2-SMASh signals were normalized to background-subtracted β-actin signal. To calculate the produced amount of CYP21A2 and CYP21A2-SMASh in 4 hours, normalized signals at 24 hours (lanes 1 and 3) were subtracted from those at 28 hours (lanes 2 and 4). With these values inputted into the mathematical model, the half-life of CYP21A2-SMASh was calculated to be 15 minutes.

FIGS. 12A and 12B show that SMASh mediates drug-inducible YFP shutoff in mammalian neurons. FIG. 12A shows rat embryonic day 15 cortico-hippocampal tissue that was dissected, dissociated, and nucleofected with plasmids encoding RFP and YFP-SMASh. Neurons were treated with either DMSO at 7 days in vitro (DIV), 3 µM ASV at 7 DIV, or 3 µM ASV at 1 DIV followed by replacement of 50% of old media with new media containing 3 µM ASV at 4 and 7 DIV. Untagged RFP verified that drug inhibition of expression was specific to the SMASh-tagged protein. Live neurons were imaged at 10 DIV in glass-bottom chambers. Representative images are shown. Scale bar, 20 µm. FIG. 12B shows mouse embryonic day 18 cortical tissue that was dissected, dissociated, and nucleofected with plasmid encoding YFP-SMASh. At 1 DIV, neurons were placed in media with or without 3 µM ASV. ASV-containing chambers had ASV replenished at 4 DIV via replacement of 50% of old media with new media containing 2 µM ASV. Live neurons were imaged at 6 DIV in glass-bottom chambers. Representative images are shown. Scale bar, 100 µm.

FIG. 13A shows dynamics of SMASh induction studied by metabolic incorporation of unnatural amino acids and labeling by click chemistry. HeLa cells expressed P-SMASh for 20 hours before the addition of combinations of the methionine analog azidohomoalanine (AHA) and/or ASV. For negative wells, an equivalent volume of DMSO was used as vehicle control. For AHA-treated wells, methionine-free media was used. Treatment lasted for 3 hours, after which cells were lysed. FIG. 13B shows a portion of lysate analyzed by immunoblot to visualize total protein. ASV treatment for 3 hours caused a drop in P protein consistent with shutoff (lane 4). HeLa lysate from an empty vector transfection was used as a control to reveal nonspecific bands (lane 1). The remainder of the lysate was reacted with biotin-alkyne to label AHA-containing proteins via azide-alkyne cycloaddition click chemistry, and labeled proteins were purified with magnetic streptavidin beads to visualize protein produced in the 3-hour labeling window. β-actin serves as a loading control for lanes 6-7, and also verifies selectivity of purification, as only minimal endogenous β-actin is purified without AHA incubation (lane 5). While cleaved P protein produced in the presence of AHA and absence of ASV is detected after purification (lane 6), no cleaved P is produced after ASV addition (lane 7), indicating rapid access of the drug to the protease. Additionally, no P-SMASh is visible, indicating efficient SMAShinduced degradation of P.

Figure 14B:
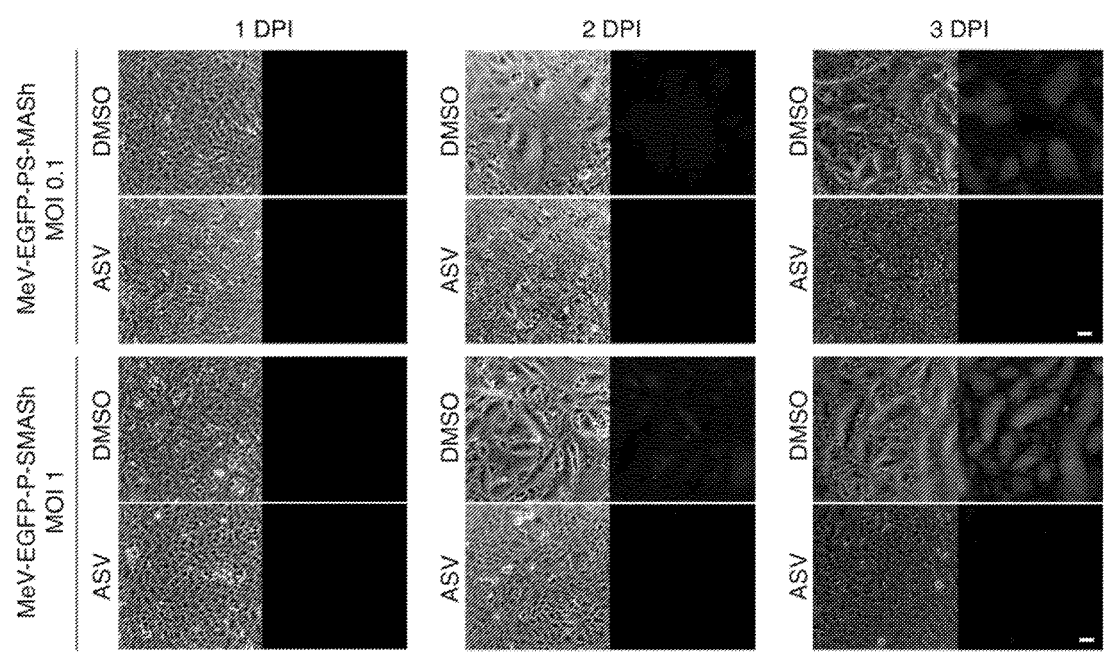

FIGS. 14A and 14B show MeV-EGFP-P-SMASh validation. FIG. 14A (Left) shows the design of RT-PCR reactions to verify MeV-EGFP-P-SMASh RNA genomic structure. Arrows denote primer locations. FIG. 14A (Right) shows the expected 1659-bp band was obtained by RT-PCR from Vero cells infected with MeV-EGFPPSMASh passages 1 and 2 viruses, and by PCR of MeV-EGFP-P-SMASh plasmid DNA as a positive control. RT-PCR from Vero cells infected with MeV-EGFP control virus yielded the expected 747-bp band. FIG. 14B shows time-lapse imaging of Vero cells infected with MeV-EGFP-P-SMASh at MOI of 0.1 or 1, grown in the absence or presence of 3 µM ASV. Images are representative of 3 replicates. Scale bar, 50 µm.

DETAILED DESCRIPTION

Figure 1A:
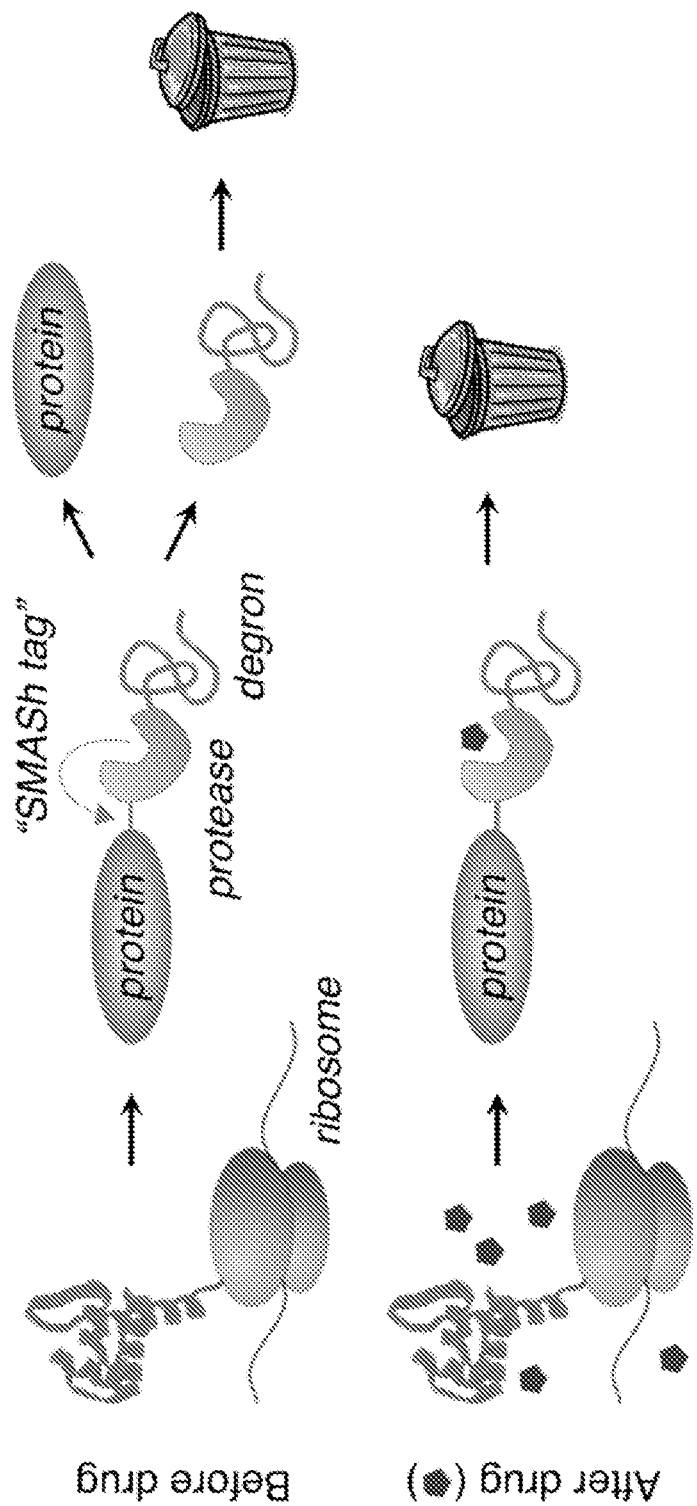

The practice of the present invention will employ, unless otherwise indicated, conventional methods of molecular biology, chemistry, biochemistry, virology, and immunology, within the skill of the art. Such techniques are explained fully in the literature. See, e.g., *Hepatitis C Viruses: Genomes and Molecular Biology* (S. L. Tan ed., Taylor & Francis, 2006); *Fundamental Virology*, 3rd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); A. L. Lehninger, Biochemistry (Worth Publishers, Inc., current addition); Sambrook, et al., *Molecular Cloning: A Laboratory Manual* (3rd Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a fusion protein" includes a mixture of two or more fusion proteins, and the like.

The term "about," particularly in reference to a given quantity, is meant to encompass deviations of plus or minus five percent.

A nonstructural protein 3 (NS3) nucleic acid, oligonucleotide, protein, polypeptide, or peptide refers to a molecule derived from hepatitis C virus (HCV), including any isolate of HCV having any genotype (e.g., seven genotypes 1-7) or subtype. The molecule need not be physically derived from HCV, but may be synthetically or recombinantly produced. A number of NS3 nucleic acid and protein sequences are known. A representative NS3 sequence is presented in SEQ ID NO:4. Additional representative sequences are listed in the National Center for Biotechnology Information (NCBI) database. See, for example, NCBI entries: Accession Nos. YP_001491553, YP_001469631, YP_001469632, NP_803144, NP_671491, YP_001469634, YP_001469630, YP_001469633, ADA68311, ADA68307, AFP99000, AFP98987, ADA68322, AFP99033, ADA68330, AFP99056, AFP99041, CBF60982, CBF60817, AHH29575, AIZ00747, AIZ00744, ABI36969, ABN05226, KF516075, KF516074, KF516056, AB826684, AB826683, JX171009, JX171008, JX171000, EU847455, EF154714, GU085487, JX171065, JX171063; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein or a recombinant polynucleotide encoding such a fusion protein, as described herein.

A nonstructural protein 4A (NS4A) nucleic acid, oligonucleotide, protein, polypeptide, or peptide refers to a molecule derived from HCV, including any isolate of HCV having any genotype (e.g., seven genotypes 1-7) or subtype. The molecule need not be physically derived from HCV, but may be synthetically or recombinantly produced. A number of NS4A nucleic acid and protein sequences are known. A representative NS4A sequence is presented in SEQ ID NO:6. Additional representative sequences are listed in the National Center for Biotechnology Information (NCBI) database. See, for example, NCBI entries: Accession Nos. NP_751925, YP_001491554, GU945462, HQ822054, FJ932208, FJ932207, FJ932205, and FJ932199; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein or a recombinant polynucleotide encoding such a fusion protein, as described herein.

A polyprotein nucleic acid, oligonucleotide, protein, polypeptide, or peptide refers to a molecule derived from HCV, including any isolate of HCV having any genotype (e.g., seven genotypes 1-7) or subtype. The molecule need not be physically derived from HCV, but may be synthetically or recombinantly produced. A number of polyprotein nucleic acid and protein sequences are known. Representative HCV polyprotein sequences are listed in the National Center for Biotechnology Information (NCBI) database. See, for example, NCBI entries: Accession Nos. YP_001469631, NP_671491, YP_001469633, YP_001469630, YP_001469634, YP_001469632, NC_009824, NC_004102, NC_009825, NC_009827, NC_009823, NC_009826, and EF108306; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein or a recombinant polynucleotide encoding such a fusion protein, as described herein.

For a discussion of genetic diversity and phylogenetic analysis of hepatitis C virus, see also Smith et al. (2014) Hepatology 59(1):318-327, Simmonds et al. (2005) Hepatology 42(4):962-973, Kuiken et al. (2009) Methods Mol. Biol. 510:33-53, Ho et al. (2015) J. Virol. Methods 219:28-37, Echeverria et al. (2015) World J. Hepatol. 7(6):831-845, and Jackowiak et al. (2014) Infect Genet Evol. 21:67-82; herein incorporated by reference in their entireties.

The terms "fusion protein," "fusion polypeptide," "degron fusion protein," or "degron fusion" as used herein refer to a fusion comprising a degron in combination with a protease and a selected polypeptide of interest as part of a single continuous chain of amino acids, which chain does not occur in nature. The degron is connected to the polypeptide of interest through a cleavable linker comprising a cleavage site capable of being recognized by the protease of the fusion to allow self-removal of the protease and degron from the polypeptide of interest. The position of the cleavage site in the fusion is preferably chosen to allow release of the polypeptide of interest from the fusion essentially unmodified or with little modification (e.g., less than 10 extra amino acids). The fusion polypeptides may be designed for N-terminal or C-terminal attachment of the degron to the polypeptide of interest. The fusion polypeptides may also contain sequences exogenous to the degron, protease, and polypeptide of interest. For example, the fusion may include targeting or localization sequences, detectable labels, or tag sequences.

The term "cleavage site" refers to the bond (e.g. a scissile bond) cleaved by an agent. A cleavage site for a protease includes the specific amino acid sequence recognized by the protease during proteolytic cleavage and typically includes the surrounding one to six amino acids on either side of the scissile bond, which bind to the active site of the protease and are needed for recognition as a substrate.

The term "cleavable linker" refers to a linker comprising a cleavage site. The cleavable linker may include a cleavage site specific for an enzyme, such as a protease or other cleavage agent. A cleavable linker is typically cleavable under physiological conditions.

The terms "polypeptide" and "protein" refer to a polymer of amino acid residues and are not limited to a minimum length. Thus, peptides, oligopeptides, dimers, multimers, and the like, are included within the definition. Both full length proteins and fragments thereof are encompassed by the definition. The terms also include postexpression modifications of the polypeptide, for example, glycosylation, acetylation, phosphorylation, hydroxylation, and the like. Furthermore, for purposes of the present invention, a "polypeptide" refers to a protein which includes modifications, such as deletions, additions and substitutions to the native sequence, so long as the protein maintains the desired activity. These modifications may be deliberate, as through site directed mutagenesis, or may be accidental, such as through mutations of hosts which produce the proteins or errors due to PCR amplification.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, as long as the desired biological activity of the native polypeptide is retained. Methods for making polypeptide fragments, analogs, and derivatives are generally available in the art.

By "fragment" is intended a molecule consisting of only a part of the intact full length sequence and structure. The fragment can include a C-terminal deletion an N-terminal deletion, and/or an internal deletion of the polypeptide. Active fragments of a particular protein or polypeptide will generally include at least about 5-10 contiguous amino acid residues of the full length molecule, preferably at least about 15-25 contiguous amino acid residues of the full length molecule, and most preferably at least about 20-50 or more contiguous amino acid residues of the full length molecule, or any integer between 5 amino acids and the full length sequence, provided that the fragment in question retains biological activity, such as catalytic activity, ligand binding activity, regulatory activity, degron protein degradation signaling, or fluorescence characteristics.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The terms "label" and "detectable label" refer to a molecule capable of detection, including, but not limited to, radioactive isotopes, stable (non-radioactive) heavy isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to radiolabels (e.g., $^3$H, $^{125}$I, $^{35}$S, $^{14}$C, or $^{32}$P), stable (non-radioactive) heavy isotopes (e.g., $^{13}$C or $^{15}$N), phycoerythrin, Alexa dyes, fluorescein, 7-nitrobenzo-2-oxa-1,3-diazole (NBD), YPet, CyPet, Cascade blue, allophycocyanin, Cy3, Cy5, Cy7, rhodamine, dansyl, umbelliferone, Texas red, luminol, acradimum esters, biotin or other streptavidin-binding proteins, magnetic beads, electron dense reagents, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), Dronpa, Padron, mApple, mCherry, rsCherry, rsCherryRev, firefly luciferase, *Renilla* luciferase, NADPH, beta-galactosidase, horseradish peroxidase, glucose oxidase, alkaline phosphatase, chloramphenical acetyl transferase, and urease. Enzyme tags are used with their cognate substrate. The terms also include color-coded microspheres of known fluorescent light intensities (see e.g., microspheres with xMAP technology produced by Luminex (Austin, Tex.); microspheres containing quantum dot nanocrystals, for example, containing different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, Calif.). As with many of the standard procedures associated with the practice of the invention, skilled artisans will be aware of additional labels that can be used.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively.

Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, D.C., which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells," "host cells," "cells," "cell lines," "cell cultures," and other such terms denoting microorganisms or higher eukaryotic cell lines, refer to cells which can be, or have been, used as recipients for a recombinant vector or other transferred DNA, and include the progeny of the cell which has been transfected. Host cells may be cultured as unicellular or multicellular entities (e.g., tissue, organs, or organoids comprising the recombinant vector).

A "coding sequence" or a sequence that "encodes" a selected polypeptide is a nucleic acid molecule that is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. For example, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence. In another example, a degron operably linked to a polypeptide is capable of promoting degradation of the polypeptide when the proper cellular degradation system (e.g., proteasome or autophagosome degradation) is present. The degron need not be contiguous with the polypeptide, so long as it functions to direct degradation of the polypeptide.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, $3^{rd}$ edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

The terms "variant," "analog" and "mutein" refer to biologically active derivatives of the reference molecule that retain desired activity, such as fluorescence or oligomerization characteristics. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and U.S. Pat. No. 5,977,301; Nguyen et al., Chem. Biol. (2000) 7:463-473; and Simon et al., Proc. Natl. Acad. Sci. USA (1992) 89:9367-9371 for descriptions of peptoids). Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region (s) from which the polynucleotide is derived. As such, it may represent either a sense or an antisense orientation of the original polynucleotide.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "recombinant virus" is meant a virus that has been genetically altered, e.g., by the addition or insertion of a heterologous nucleic acid construct into the particle.

"Recombinant virion," as used herein, refers to a viral particle containing a recombinant viral vector (e.g., conditionally replicating viral vector encoding a degron fusion protein). Generally, a recombinant virion comprises one or more structural proteins and the viral vector. The recombinant virion may also contain a nucleocapsid structure, and in some cases, a lipid envelope derived from the host cell membrane.

The terms "subject" refers to any invertebrate or vertebrate subject, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

"Recombinant animal" refers to a nonhuman subject which has been a recipient of a recombinant vector or other transferred DNA, and also includes the progeny of a recombinant animal.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of a novel degron comprising sequences derived from NS3 and NS4A components of HCV. This degron can be used in the Small Molecule-Assisted Shutoff (SMASh) technique, described in Example 1, in which a protein of interest is fused to a self-excising degron and thereby expressed in a minimally modified form. The degron can be removed from the protein of interest by a cis-encoded HCV protease. Clinically available HCV protease inhibitors can be used to block protease cleavage such that the degron is retained after inhibitor addition on subsequently synthesized protein copies. The degron when attached causes rapid degradation of the linked protein. The inventors have shown that SMASh allows reversible and dose-dependent shutoff of various proteins with high dynamic range in multiple cell types, including yeast and neurons. SMASh was also used with this degron to confer drug responsiveness on an RNA virus for which no licensed drug inhibitors exist. As SMASh does not require permanent fusion of a large domain, this technique will be useful when control over protein production with minimal structural modification is desired.

In order to further an understanding of the invention, a more detailed discussion is provided below regarding the identified degron and its use in the SMASh method for controlling production of proteins and viral replication.

A. Degron Fusion Proteins

Degron fusion proteins comprise a degron in combination with a protease connected to a selected polypeptide of interest in an arrangement designed to control production of the polypeptide of interest. The degron is connected to the polypeptide of interest through a cleavable linker comprising a cleavage site capable of being recognized by the protease of the fusion protein in order to allow self-removal of the protease and degron from the polypeptide of interest. The position of the cleavage site in the fusion is preferably chosen to allow release of the polypeptide of interest from the fusion protein essentially unmodified or with little modification (e.g., less than 10 extra amino acids). The fusion polypeptides may be designed with N-terminal or C-terminal attachment of the degron to the polypeptide of interest. The degron need not be contiguous with the polypeptide of interest, as long as it functions to direct degradation of the polypeptide. The fusion protein may also contain sequences exogenous to the degron, protease, and polypeptide of interest. For example, the fusion may include targeting or localization sequences, or tag sequences. In addition, the fusion protein may comprise a detectable label (e.g., fluorescent, bioluminescent, chemiluminescent, colorimetric, or isotopic label) to facilitate monitoring production and degradation of the polypeptide of interest.

The polypeptide of interest selected for inclusion in the fusion protein may be from a membrane protein, a receptor, a hormone, a transport protein, a transcription factor, a cytoskeletal protein, an extracellular matrix protein, a signal-transduction protein, an enzyme, or any other protein of interest. The polypeptide of interest may comprise an entire protein, or a biologically active domain (e.g., a catalytic domain, a ligand binding domain, or a protein-protein interaction domain), or a polypeptide fragment of a selected protein.

The degron comprises a sequence of amino acids, which provides a degradation signal that directs a polypeptide for cellular degradation. The degron may promote degradation of an attached polypeptide through either the proteasome or autophagy-lysosome pathways. In the fusion protein, the degron must be operably linked to the polypeptide of interest, but need not be contiguous with it as long as the degron still functions to direct degradation of the polypeptide of interest. Preferably, the degron induces rapid degradation of the polypeptide of interest. For a discussion of degrons and their function in protein degradation, see, e.g., Kanemaki et al. (2013) Pflugers Arch. 465(3):419-425, Erales et al. (2014) Biochim Biophys Acta 1843(1):216-221, Schrader et al. (2009) Nat. Chem. Biol. 5(11):815-822, Ravid et al. (2008) Nat. Rev. Mol. Cell. Biol. 9(9):679-690, Tasaki et al. (2007) Trends Biochem Sci. 32(11):520-528, Meinnel et al. (2006) Biol. Chem. 387(7):839-851, Kim et al. (2013) Autophagy 9(7):1100-1103, Varshaysky (2012) Methods Mol. Biol. 832:1-11, and Fayadat et al. (2003) Mol Biol Cell. 14(3):1268-1278; herein incorporated by reference.

In certain embodiments, the degron comprises portions of the HCV nonstructural proteins NS3 and NS4A (as described in Example 1). In one embodiment, the degron comprises the amino acid sequence of SEQ ID NO:1 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the degron is capable of promoting degradation of a polypeptide. It is to be understood that degrons comprising the residues corresponding to the reference sequence of SEQ ID NO:1 in HCV nonstructural proteins NS3 and NS4A obtained from other strains of HCV are also intended to be encompassed by the present invention.

In the fusion protein, the degron may be linked to the N-terminus or the C-terminus of the polypeptide of interest. For example, the fusion protein can be represented by the formula $NH_2$-P-D-L-X-COOH or $NH_2$-X-L-P-D-COOH, wherein: P is an amino acid sequence of a protease; D is an amino acid sequence of a degron; L is an amino acid sequence of a linker comprising a cleavage site for the protease; and X is an amino acid sequence of a selected polypeptide of interest.

The cleavable linker between the polypeptide of interest and the degron is designed for selective cleavage by the particular protease included in the fusion protein. The cleavage site of the linker includes the specific amino acid sequence recognized by the protease during proteolytic cleavage and typically includes the surrounding one to six amino acids on either side of the scissile bond, which bind to the active site of the protease and are needed for recognition as a substrate. The cleavable linker may contain any protease recognition motif known in the art and is typically cleavable under physiological conditions.

Exemplary proteases which can be used in fusion proteins include hepatitis C virus proteases (e.g., NS3 and NS2-3); signal peptidase; proprotein convertases of the subtilisin/kexin family (furin, PC1, PC2, PC4, PACE4, PC5, PC); proprotein convertases cleaving at hydrophobic residues (e.g., Leu, Phe, Val, or Met); proprotein convertases cleaving at small amino acid residues such as Ala or Thr; proopiomelanocortin converting enzyme (PCE); chromaffin granule aspartic protease (CGAP); prohormone thiol protease; carboxypeptidases (e.g., carboxypeptidase E/H, carboxypeptidase D and carboxypeptidase Z); aminopeptidases (e.g., arginine aminopeptidase, lysine aminopeptidase, aminopeptidase B); prolyl endopeptidase; aminopeptidase N; insulin degrading enzyme; calpain; high molecular weight protease; and, caspases 1, 2, 3, 4, 5, 6, 7, 8, and 9. Other proteases include, but are not limited to, aminopeptidase N; puromycin sensitive aminopeptidase; angiotensin converting enzyme; pyroglutamyl peptidase II; dipeptidyl peptidase IV; N-arginine dibasic convertase; endopeptidase 24.15; endopeptidase 24.16; amyloid precursor protein secretases alpha, beta and gamma; angiotensin converting enzyme secretase; TGF alpha secretase; TNF alpha secretase; FAS ligand secretase; TNF receptor-I and -II secretases; CD30 secretase; KL1 and KL2 secretases; IL6 receptor secretase; CD43, CD44 secretase; CD16-I and CD16-II secretases; L-selectin secretase; Folate receptor secretase; MMP 1, 2, 3, 7, 8, 9, 10, 11, 12, 13, 14, and 15; urokinase plasminogen activator; tissue plasminogen activator; plasmin; thrombin; BMP-1 (procollagen C-peptidase); ADAM 1, 2, 3, 4, 5, 6, 7, 8, 9, 10, and 11; and, granzymes A, B, C, D, E, F, G, and H. The protease chosen for use in the fusion protein is preferably highly selective for the cleavage site in the cleavable linker. Additionally, protease activity is preferably inhibitable with inhibitors that are cell-permeable and not toxic to the cell or subject under study. For a discussion of proteases, see, e.g., V.

Y. H. Hook, Proteolytic and cellular mechanisms in prohormone and proprotein processing, RG Landes Company, Austin, Tex., USA (1998); N. M. Hooper et al., Biochem. J. 321: 265-279 (1997); Z. Werb, Cell 91: 439-442 (1997); T. G. Wolfsberg et al., J. Cell Biol. 131: 275-278 (1995); K. Murakami and J. D. Etlinger, Biochem. Biophys. Res. Comm. 146: 1249-1259 (1987); T. Berg et al., Biochem. J. 307: 313-326 (1995); M. J. Smyth and J. A. Trapani, Immunology Today 16: 202-206 (1995); R. V. Talanian et al., J. Biol. Chem. 272: 9677-9682 (1997); and N. A. Thornberry et al., J. Biol. Chem. 272: 17907-17911 (1997), the disclosures of which are incorporated herein.

In certain embodiments, the protease used in the fusion protein is a hepatitis C virus (HCV) nonstructural protein 3 (NS3) protease. NS3 consists of an N-terminal serine protease domain and a C-terminal helicase domain. The protease domain of NS3 forms a heterodimer with the HCV nonstructural protein 4A (NS4A), which activates proteolytic activity. An NS3 protease may comprise the entire NS3 protein or a proteolytically active fragment thereof and may further comprise an activating NS4A region. Advantages of using an NS3 protease include that it is highly selective and can be well-inhibited by a number of non-toxic, cell-permeable drugs, which are currently clinically available. NS3 protease inhibitors that can be used in the practice of the invention include, but are not limited to, simeprevir, danoprevir, asunaprevir, ciluprevir, boceprevir, sovaprevir, paritaprevir and telaprevir.

When an NS3 protease is used in a degron fusion protein, the cleavable linker of the fusion protein should comprise an NS3 protease cleavage site. Exemplary NS3 protease cleavage sites, which can be used in the cleavable linker, include the four junctions between nonstructural (NS) proteins of the HCV polyprotein normally cleaved by the NS3 protease during HCV infection, including the NS3/NS4A, NS4A/NS4B, NS4B/NS5A, and NS5A/NS5B junction cleavage sites. For a description of NS3 protease and representative sequences of its cleavage sites for various strains of HCV, see, e.g., *Hepatitis C Viruses: Genomes and Molecular Biology* (S. L. Tan ed., Taylor & Francis, 2006), Chapter 6, pp. 163-206; herein incorporated by reference in its entirety.

NS3 nucleic acid and protein sequences may be derived from HCV, including any isolate of HCV having any genotype (e.g., seven genotypes 1-7) or subtype. A number of NS3 nucleic acid and protein sequences are known. A representative NS3 sequence is presented in SEQ ID NO:4. Additional representative sequences are listed in the National Center for Biotechnology Information (NCBI) database. See, for example, NCBI entries: Accession Nos. YP_001491553, YP_001469631, YP_001469632, NP_803144, NP_671491, YP_001469634, YP_001469630, YP_001469633, ADA68311, ADA68307, AFP99000, AFP98987, ADA68322, AFP99033, ADA68330, AFP99056, AFP99041, CBF60982, CBF60817, AHH29575, AIZ00747, AIZ00744, ABI36969, ABN05226, KF516075, KF516074, KF516056, AB826684, AB826683, JX171009, JX171008, JX171000, EU847455, EF154714, GU085487, JX171065, JX171063; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein or a recombinant polynucleotide encoding such a fusion protein, as described herein.

NS4A nucleic acid and protein sequences may be derived from HCV, including any isolate of HCV having any genotype (e.g., seven genotypes 1-7) or subtype. A number of NS4A nucleic acid and protein sequences are known. A representative NS4A sequence is presented in SEQ ID NO:6. Additional representative sequences are listed in the National Center for Biotechnology Information (NCBI) database. See, for example, NCBI entries: Accession Nos. NP_751925, YP_001491554, GU945462, HQ822054, FJ932208, FJ932207, FJ932205, and FJ932199; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein or a recombinant polynucleotide encoding such a fusion protein, as described herein.

HCV polyprotein nucleic acid and protein sequences may be derived from HCV, including any isolate of HCV having any genotype (e.g., seven genotypes 1-7) or subtype. A number of HCV polyprotein nucleic acid and protein sequences are known. Representative HCV polyprotein sequences are listed in the National Center for Biotechnology Information (NCBI) database. See, for example, NCBI entries: Accession Nos. YP_001469631, NP_671491, YP_001469633, YP_001469630, YP_001469634, YP_001469632, NC_009824, NC_004102, NC_009825, NC_009827, NC_009823, NC_009826, and EF108306; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein or a recombinant polynucleotide encoding such a fusion protein, as described herein.

The polypeptides included in the fusion construct may be connected directly to each other by peptide bonds or may be separated by intervening amino acid sequences. The fusion polypeptides may also contain sequences exogenous to the protease or the selected protein of interest. For example, the fusion protein may include targeting or localization sequences, tag sequences, or sequences of fluorescent or bioluminescent proteins.

In certain embodiments, tag sequences are located at the N-terminus or C-terminus of the fusion protein. Exemplary tags that can be used in the practice of the invention include a His-tag, a Strep-tag, a TAP-tag, an S-tag, an SBP-tag, an Arg-tag, a calmodulin-binding peptide tag, a cellulose-binding domain tag, a DsbA tag, a c-myc tag, a glutathione S-transferase tag, a FLAG tag, a HAT-tag, a maltose-binding protein tag, a NusA tag, and a thioredoxin tag.

In certain embodiments, the fusion protein comprises a targeting sequence. Exemplary targeting sequences that can be used in the practice of the invention include a secretory protein signal sequence, a membrane protein signal sequence, a nuclear localization sequence, a nucleolar localization signal sequence, an endoplasmic reticulum localization sequence, a peroxisome localization sequence, a mitochondrial localization sequence, and a protein-protein interaction motif sequence. Examples of targeting sequences include those targeting the nucleus (e.g., KKKRK, SEQ ID NO:12), mitochondrion (e.g., MLRTSSLF-TRRVQPSLFRNILRLQST, SEQ ID NO:13), endoplasmic reticulum (e.g., KDEL, SEQ ID NO:14), peroxisome (e.g., SKL), synapses (e.g., S/TDV or fusion to GAP 43, kinesin or tau), plasma membrane (e.g., CaaX (SEQ ID NO:15) where "a" is an aliphatic amino acid, CC, CXC, CCXX (SEQ ID NO:16) at C-terminus), or protein-protein interaction motifs (e.g., SH2, SH3, PDZ, WW, RGD, Src homology domain, DNA-binding domain, SLiMs).

In certain embodiments, the fusion protein comprises a detectable label. The detectable label may comprise any molecule capable of detection. Detectable labels that may be used in the practice of the invention include, but are not limited to, radioactive isotopes, stable (non-radioactive) heavy isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. Particular examples of labels that may be used with the invention include, but are not limited to radiolabels (e.g., $^3$H, $^{125}$I, $^{35}$S, $^{14}$C, or $^{32}$P), stable (non-radioactive) heavy isotopes (e.g., $^{13}$C or $^{15}$N), phycoerythrin, Alexa dyes, fluorescein, 7-nitrobenzo-2-oxa-1,3-diazole (NBD), YPet, CyPet, Cascade blue, allophycocyanin, Cy3, Cy5, Cy7, rhodamine, dansyl, umbelliferone, Texas red, luminol, acradimum esters, biotin or other streptavidin-binding proteins, magnetic beads, electron dense reagents, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), Dronpa, Padron, mApple, mCherry, rsCherry, rsCherryRev, firefly luciferase, *Renilla* luciferase, NADPH, beta-galactosidase, horseradish peroxidase, glucose oxidase, alkaline phosphatase, chloramphenical acetyl transferase, and urease. Enzyme tags are used with their cognate substrate. The terms also include color-coded microspheres of known fluorescent light intensities (see e.g., microspheres with xMAP technology produced by Luminex (Austin, Tex.); microspheres containing quantum dot nanocrystals, for example, containing different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, Calif.). As with many of the standard procedures associated with the practice of the invention, skilled artisans will be aware of additional labels that can be used.

B. Production of Degron Fusion Proteins

Degron fusion proteins can be produced using recombinant techniques well known in the art. One of skill in the art can readily determine nucleotide sequences that encode the desired polypeptides using standard methodology and the teachings herein. Oligonucleotide probes can be devised based on the known sequences and used to probe genomic or cDNA libraries. The sequences can then be further isolated using standard techniques and, e.g., restriction enzymes employed to truncate the gene at desired portions of the full-length sequence. Similarly, sequences of interest can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The sequences encoding polypeptides can also be produced synthetically, for example, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311; Stemmer et al. (1995) *Gene* 164:49-53.

Recombinant techniques are readily used to clone sequences encoding polypeptides useful in the claimed fusion proteins that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409.

Once coding sequences have been isolated and/or synthesized, they can be cloned into any suitable vector or replicon for expression. (See, also, Examples). As will be apparent from the teachings herein, a wide variety of vectors encoding modified polypeptides can be generated by creating expression constructs which operably link, in various combinations, polynucleotides encoding polypeptides having deletions or mutations therein.

Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), 0.161 (*Streptomyces*), pUC6 (*Streptomyces*), YIp5 (*Saccharomyces*), YCp19 (*Saccharomyces*) and bovine papilloma virus (mammalian cells). See, generally, *DNA Cloning*: Vols. I & II, supra; Sambrook et al., supra; B. Perbal, supra.

Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

Plant expression systems can also be used to produce the fusion proteins described herein. Generally, such systems use virus-based vectors to transfect plant cells with heterologous genes. For a description of such systems see, e.g., Porta et al., *Mol. Biotech.* (1996) 5:209-221; and Hackland et al., *Arch. Virol.* (1994) 139:1-22.

Viral systems, such as a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. With the present invention, both the naturally occurring signal peptides and heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector that already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the fusion proteins of the present invention are produced by growing host cells transformed by an expression vector described above under conditions whereby the protein of interest is expressed. The selection of the appropriate growth conditions is within the skill of the art.

In one embodiment, the transformed cells secrete the polypeptide product into the surrounding media. Certain regulatory sequences can be included in the vector to enhance secretion of the protein product, for example using a tissue plasminogen activator (TPA) leader sequence, an interferon (γ or α) signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the recombinant polypeptides substantially intact. Intracellular proteins can also be obtained by removing components from the cell wall or membrane, e.g., by the use of detergents or organic solvents, such that leakage of the polypeptides occurs. Such methods are known to those of skill in the art and are described in, e.g., *Protein Purification Applications: A Practical Approach*, (Simon Roe, Ed., 2001).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular polypeptides of the present invention involves affinity purification, such as by immunoaffinity chromatography using antibodies (e.g., previously generated antibodies), or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the polypeptides can be further purified using conventional techniques well known in the art, such as by any of the techniques described above.

C. Nucleic Acids Encoding Degron Fusion Proteins

Nucleic acids encoding degron fusion proteins can be used, for example, to control production of a polypeptide of interest in a cell, tissue, organ, organoid, or subject (e.g., invertebrate or vertebrate animal). Upon delivery or expression of the fusion protein in a cell, tissue, organ, organoid, or subject, the degron is continuously cleaved from the fusion protein in the absence of a protease inhibitor, thereby preventing the degron from directing degradation of the polypeptide of interest. In the presence of a protease inhibitor (e.g., a drug or small molecule), the degron remains linked to the polypeptide of interest resulting in rapid degradation of the polypeptide of interest in any fusion proteins synthesized after the time of addition of the inhibitor. Thus, production of the polypeptide of interest is readily controlled.

The ability of constructs to produce degron fusion proteins can be empirically determined (e.g., see Example 1 describing detection of fusion proteins labeled with EGFP or AHA by fluorescence microscopy or immunoblotting, respectively). Additionally, production and degradation of the polypeptide of interest in the presence and absence of protease inhibitors can be monitored. Because the presence of a protease inhibitor prevents accumulation of new protein copies without affecting old copies, the overall levels of a polypeptide of interest after adding the protease inhibitor depend on its degradation rate. Accordingly, the half-life of the polypeptide of interest in a cell can be readily calculated by monitoring its decay. Additionally, the turnover of the polypeptide of interest can be determined by measuring amounts of the polypeptide of interest in a transformed cell before and after contacting the cell with a protease inhibitor and calculating the turnover of the polypeptide of interest based on the amounts of the polypeptide of interest in the cell before and after adding the protease inhibitor. The amount of the polypeptide of interest in the cell can be measured either continuously or periodically over a period of time by any suitable method (e.g., immunoblotting or microscopy).

Nucleic acids described herein can be inserted into an expression vector to create an expression cassette capable of producing the degron fusion proteins in a suitable host cell (e.g. in a tissue, organ, organoid, or subject). Expression cassettes typically include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of mammalian constructs. Examples include the SV40 early gene enhancer, as described in Dijkema et al., EMPO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Constructs encoding degron fusion proteins can be administered to a subject or introduced into cells, tissue, organs, or organoids using standard gene delivery protocols. Methods for gene delivery are known in the art. See, e.g., U.S. Pat. Nos. 5,399,346, 5,580,859, 5,589,466. Genes can be delivered either directly to a subject or, alternatively, delivered ex vivo, to cells derived from the subject and the cells reimplanted in the subject.

A number of viral based systems have been developed for gene transfer into mammalian cells. These include adenoviruses, retroviruses (γ-retroviruses and lentiviruses), poxviruses, adeno-associated viruses, baculoviruses, and herpes simplex viruses (see e.g., Warnock et al. (2011) Methods Mol. Biol. 737:1-25; Walther et al. (2000) Drugs 60(2):249-271; and Lundstrom (2003) Trends Biotechnol. 21(3):117-122; herein incorporated by reference).

For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; Boris-Lawrie and Temin (1993) Cur. Opin. Genet. Develop. 3:102-109; and Ferry et al. (2011) Curr Pharm Des. 17(24):2516-2527). Lentiviruses are a class of retroviruses that are particularly useful for delivering polynucleotides to mammalian cells because they are able to infect both dividing and nondividing cells (see e.g., Lois et al (2002) Science 295:868-872; Durand et al. (2011) Viruses 3(2):132-159; herein incorporated by reference).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding the degron fusion proteins include those derived from the pox family of viruses, including vaccinia virus and avian poxvirus. By way of example, vaccinia virus recombinants expressing the fusion proteins can be constructed as follows. The DNA encoding the particular fusion protein coding sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as, but not limited to, vectors derived from the Sindbis virus (SIN), Semliki Forest virus (SFV), and Venezuelan Equine Encephalitis virus (VEE), will also find use as viral vectors for delivering the polynucleotides of the present invention. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J.

Virol. 77: 10394-10403 and International Publication Nos. WO 02/099035, WO 02/080982, WO 01/81609, and WO 00/61772; herein incorporated by reference in their entireties.

A vaccinia based infection/transfection system can be conveniently used to provide for inducible, transient expression of the coding sequences of interest (for example, a degron fusion protein expression cassette) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135,855.

The synthetic expression cassette of interest can also be delivered without a viral vector. For example, the synthetic expression cassette can be packaged as DNA or RNA in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, e.g., Hug and Sleight, Biochim. Biophys. Acta (1991) 1097:1-17; Straubinger et al., in Methods of Enzymology (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Feigner et al., Proc. Natl. Acad. Sci. USA (1987) 84:7413-7416); mRNA (Malone et al., Proc. Natl. Acad. Sci. USA (1989) 86:6077-6081); and purified transcription factors (Debs et al., J. Biol. Chem. (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Feigner et al., Proc. Natl. Acad. Sci. USA (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., Proc. Natl. Acad. Sci. USA (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., Proc. Natl. Acad. Sci. USA (1978) 75:4194-4198; Papahadjopoulos et al., Biochim. Biophys. Acta (1975) 394:483; Wilson et al., Cell (1979) 17:77); Deamer and Bangham, Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); Enoch and Strittmatter, Proc. Natl. Acad. Sci. USA (1979) 76:145); Fraley et al., J. Biol. Chem. (1980) 255:10431; Szoka and Papahadjopoulos, Proc. Natl. Acad. Sci. USA (1978) 75:145; and Schaefer-Ridder et al., Science (1982) 215:166.

The DNA and/or peptide(s) can also be delivered in cochleate lipid compositions similar to those described by Papahadjopoulos et al., Biochem. Biophys. Acta (1975) 394:483-491. See, also, U.S. Pat. Nos. 4,663,161 and 4,871,488.

The expression cassette of interest may also be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; McGee J. P., et al., J Microencapsul. 14(2):197-210, 1997; O'Hagan D. T., et al., Vaccine 11(2):149-54, 1993.

Furthermore, other particulate systems and polymers can be used for the in vivo or ex vivo delivery of the nucleic acid of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., Advanced Drug Delivery Reviews (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, Vaccine 12:1503-1509, 1994; Bioject, Inc., Portland, Oreg.).

Recombinant vectors can be formulated into compositions for delivery to a vertebrate subject. The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, surfactants and the like, may be present in such vehicles. Certain facilitators of nucleic acid uptake and/or expression can also be included in the compositions or coadministered.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) in liposomes, and direct microinjection of the DNA into nuclei.

Direct delivery of synthetic expression cassette compositions in vivo will generally be accomplished with or without viral vectors, as described above, by injection using either a conventional syringe, needless devices such as Bioject™ or a gene gun, such as the Accell gene delivery system (PowderMed Ltd, Oxford, England).

D. Conditionally Replicating Viral Vectors Encoding Degron Fusion Proteins

Conditionally replicating viral vectors controllable with protease inhibitors can be designed by modifying a viral genome to express a polypeptide required for efficient replication of the virus as part of a degron fusion protein, as described herein. In the presence of a protease inhibitor, the degron promotes degradation of the polypeptide required for efficient replication of the virus. In the absence of a protease inhibitor, cleavage of the fusion protein by the protease releases the polypeptide required for efficient replication of the virus from control of the degron allowing the virus to replicate. Such conditionally replicating viral vectors will be useful in any situation where safety is a concern, for example, when using viruses engineered for enhanced cytotoxicity or immune evasion or viruses for which no inhibitors are currently available, and for treating immunodeficient or immunosuppressed subjects.

For example, this method can be used to enhance the safety of RNA virus-based therapies. There are currently no clinically available inhibitors for most RNA viruses. The options for controlling RNA viruses are limited because their life cycles bypass DNA replication and transcription. Viral vectors, engineered to encode degron fusion proteins, as described herein, can be used to regulate protein production directly and provide a way to switch off replication of viruses that would otherwise be difficult to control.

In particular, this method can be used to enhance the safety of oncolytic viruses. RNA viruses, such as measles virus and vesicular stomatitis virus, which infect and lyse tumor cells, have found use in cancer therapy. Such oncolytic viruses can be brought under the control of a protease inhibitor by incorporating a polypeptide required for efficient replication of the virus into a degron fusion construct. For example, the viral phosphoprotein in measles virus is needed for efficient replication. The phosphoprotein brings the viral large protein, an RNA-dependent RNA polymerase, to the nucleoprotein-encapsidated viral genome, a critical step in viral replication. Engineering the measles virus to express the viral phosphoprotein as a degron fusion protein allows production of the phosphoprotein, and in turn viral replication, to be controlled by protease inhibitors.

In one embodiment, a conditionally replicating measles viral vector comprises the nucleotide sequence of SEQ ID NO:9, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein production of the virus can be inhibited with an HCV NS3 protease inhibitor. An exemplary conditionally replicating measles virus vector is described in Example 1.

Packaging of viral vectors into particles can be accomplished by introducing the viral vector into cells (e.g., RNA or DNA transfection, or particle infection) and culturing cells under conditions suitable for production of virions. Conditionally replicating viral vectors preferably are capable of providing efficient production of virions in a host cell in the absence of a protease inhibitor, comparable to the level of virions produced by the wild-type viral genome. In certain embodiments, the level of virions produced by a conditionally replicating viral vector in the absence of a protease inhibitor is at least about 30%, 35%, 40%, 45%, 50%, 55%, 60%, 65%, 70%, 75%, 80%, 85%, 90%, 95%, or 100%, or any amount in between as compared to levels of virions produced by the wild-type viral genome.

Additionally, production of virions from a conditionally replicating viral vector preferably can be nearly completely suppressed in the presence of a protease inhibitor. For example, a protease inhibitor may reduce production of virions by at least 80%, 90%, or 100%, or any amount in between as compared to levels of virions in the absence of the protease inhibitor. In certain embodiments, production of virions by the conditionally replicating viral vector in the host cell in the presence of the protease inhibitor is at least about 90% to 100% suppressed, including any percent identity within this range, such as 90, 91, 92, 93, 94, 95, 96, 97, 98, or 99%.

E. Kits

Degron fusion proteins or nucleic acids encoding them as well as conditionally replicating viral vectors can be provided in kits with suitable instructions and other necessary reagents for preparing or using them, as described above. The kit may contain in separate containers fusion proteins, and/or recombinant constructs for producing fusion proteins, and/or conditionally replicating viral vectors, and/or cells (either already transfected or separate). Additionally, instructions (e.g., written, tape, VCR, CD-ROM, DVD, Blu-ray, flash drive, etc.) for using the fusion proteins or viral vectors may be included in the kit. The kit may further include a protease inhibitor, such as an HCV NS3 protease inhibitor, including, for example, simeprevir, danoprevir, asunaprevir, ciluprevir, boceprevir, sovaprevir, paritaprevir, or telaprevir. The kit may also contain other packaged reagents and materials (e.g., transfection reagents, buffers, media, and the like).

In certain embodiments, the kit comprises a recombinant polynucleotide encoding a degron fusion protein described herein. In one embodiment, the kit comprises a recombinant polynucleotide encoding a fusion protein comprising a sequence selected from the group consisting of SEQ ID NO:7 and SEQ ID NO:8, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fusion protein comprises a degron operably linked to a polypeptide of interest, which is capable of promoting degradation of the polypeptide of interest, and a protease capable of cleaving the fusion protein at a cleavage site.

In other embodiments, the kit comprises a conditionally replicating viral vector as described herein. In one embodiment, the kit comprises a conditionally replicating viral vector comprising the nucleotide sequence of SEQ ID NO:9, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein production of the virus can be inhibited with a protease inhibitor.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Small Molecule-Assisted Shutoff: A Widely Applicable Method for Tunable and Reversible Control of Protein Production Introduction The ability to quickly control the production of specific proteins would be useful in biomedical research and biotechnology. An ideal method would feature 1) genetic specification of the target protein, 2) a single genetic element for simplicity, 3) minimal modification of the expressed protein, 4) generalizability to many proteins and cell types, and 5) control by a drug with proven safety and bioavailability at the required doses in mammals. While methods have been devised with some of these characteristics (Table 1), none have encompassed all of them.

We envisaged that a degron that removes itself in a drug-controllable manner could serve as the basis for a new method with all the desired features. In particular, we reasoned that if a site-specific drug-inhibitable protease and a degron were fused to a protein of interest via an intervening protease site, then by default the protease and degron would be removed by cis-cleavage and the protein expressed in a minimally modified form. However, in the presence of the protease inhibitor, the degron would remain attached and lead to rapid degradation of the protein (FIG. 1A).

Here, we show that a system of this design using the hepatitis C virus (HCV) nonstructural protein 3 (NS3) protease and elements in the NS4A protein enables clinically tested HCV protease inhibitors to effectively shut off expression. We termed this method "small-molecule assisted shutoff", or SMASh. SMASh enabled drug-induced inhibition of the production of various proteins in multiple eukaryotic cell types. In contrast to other single-component methods of post-translational regulation of protein expression, SMASh functions robustly in yeast as well. Finally, we used SMASh to confer HCV protease inhibitor sensitivity onto an RNA virus currently in clinical trials for cancer but for which no licensed drug inhibitor exists. SMASh thus enables post-translational regulation of protein production with rapid onset and minimal protein modification in a broad array of experimental systems, while requiring only the fusion of a single genetic element to the coding sequence of a protein of interest.

Results

Development of the SMASh Tag, a Drug-Controllable Self-Removing Degron

We had previously utilized HCV NS3 protease to control protein tagging in a drug-dependent manner (Butko et al. (2012) Nat Neurosci 15(12):1742-1751; Lin et al. (2008) Proc Natl Acad Sci USA 105:7744-7749) because it is monomeric and highly selective, and because multiple non-toxic cell-permeable inhibitors are available, such as simeprevir, danoprevir, asunaprevir, and ciluprevir (Jiang et al. (2014) J Med Chem 57:1753-1769; Lamarre et al. (2003) Nature 426:186-189; McPhee et al. (2012) Antimicrob Agents Chemother 56(10):5387-5396; Talwani, et al. (2013) Drugs Today (Barc) 49:769-779). We hypothesized that we could use a NS3 protease fused in cis to remove a degron from a protein of interest shortly after translation by default, then apply a protease inhibitor to block degron removal on subsequently synthesized copies. If the degron is sufficiently strong, then the protease inhibitor would cause new proteins to be rapidly degraded, in effect shutting off further protein production. We refer to this strategy as Small Molecule-Assisted Shutoff, or SMASh (FIG. 1A).

Figure 1C:
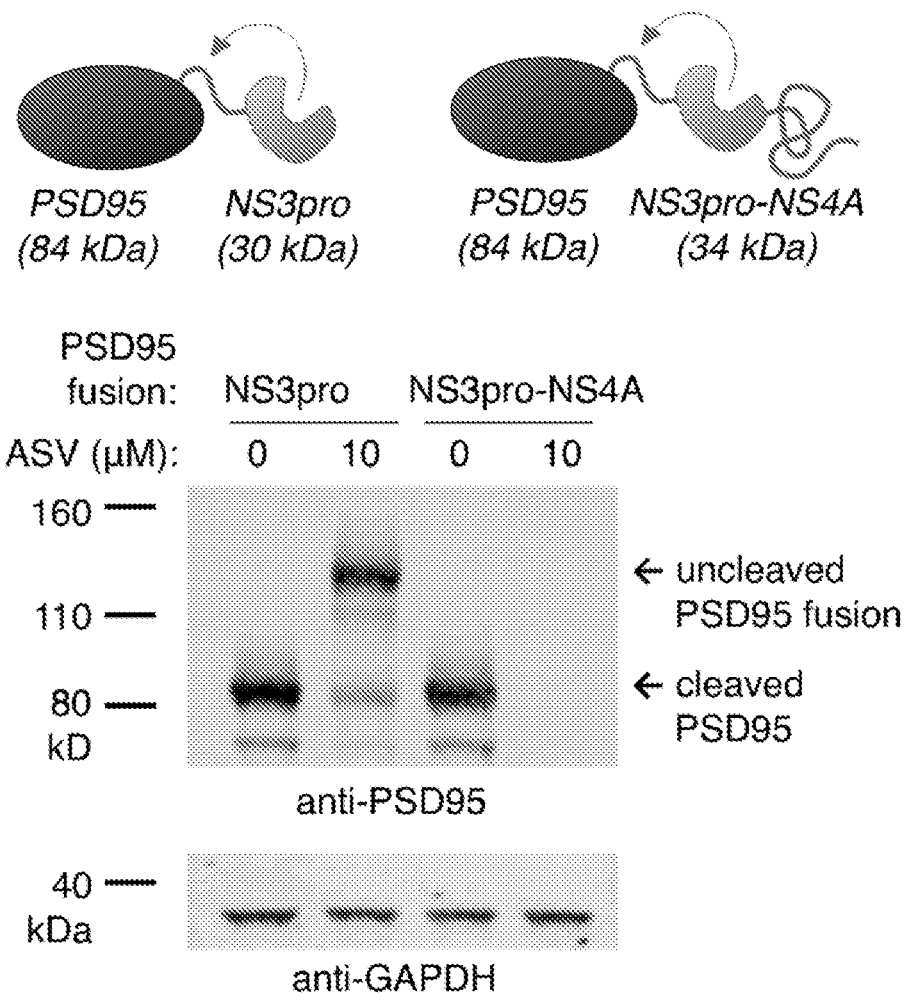

During the development of a tag for newly synthesized proteins called TimeSTAMP2 (TS2) that incorporated the NS3 protease domain (Butko et al. (2012) Nat Neurosci 15(12):1742-1751), we cloned a sequence encoding the NS3 protease domain (hereafter referred to as NS3pro) followed by the NS4A protein (FIG. 1B). We noticed that when we fused the neuronal synaptic protein PSD95 to NS3pro alone via a linker containing a cognate substrate sequence, PSD95 was well expressed regardless of whether self-removal of NS3pro was allowed to occur or was inhibited by asunaprevir (FIG. 1C, lanes 1 and 2). However, when we fused PSD95 via the same linker to NS3pro followed by NS4A, PSD95 was well expressed when self-removal of the NS3pro-NS4A cassette was allowed to occur, but was poorly expressed when self-removal was inhibited by asunaprevir (FIG. 1C, lanes 3 and 4).

Figure 8A:
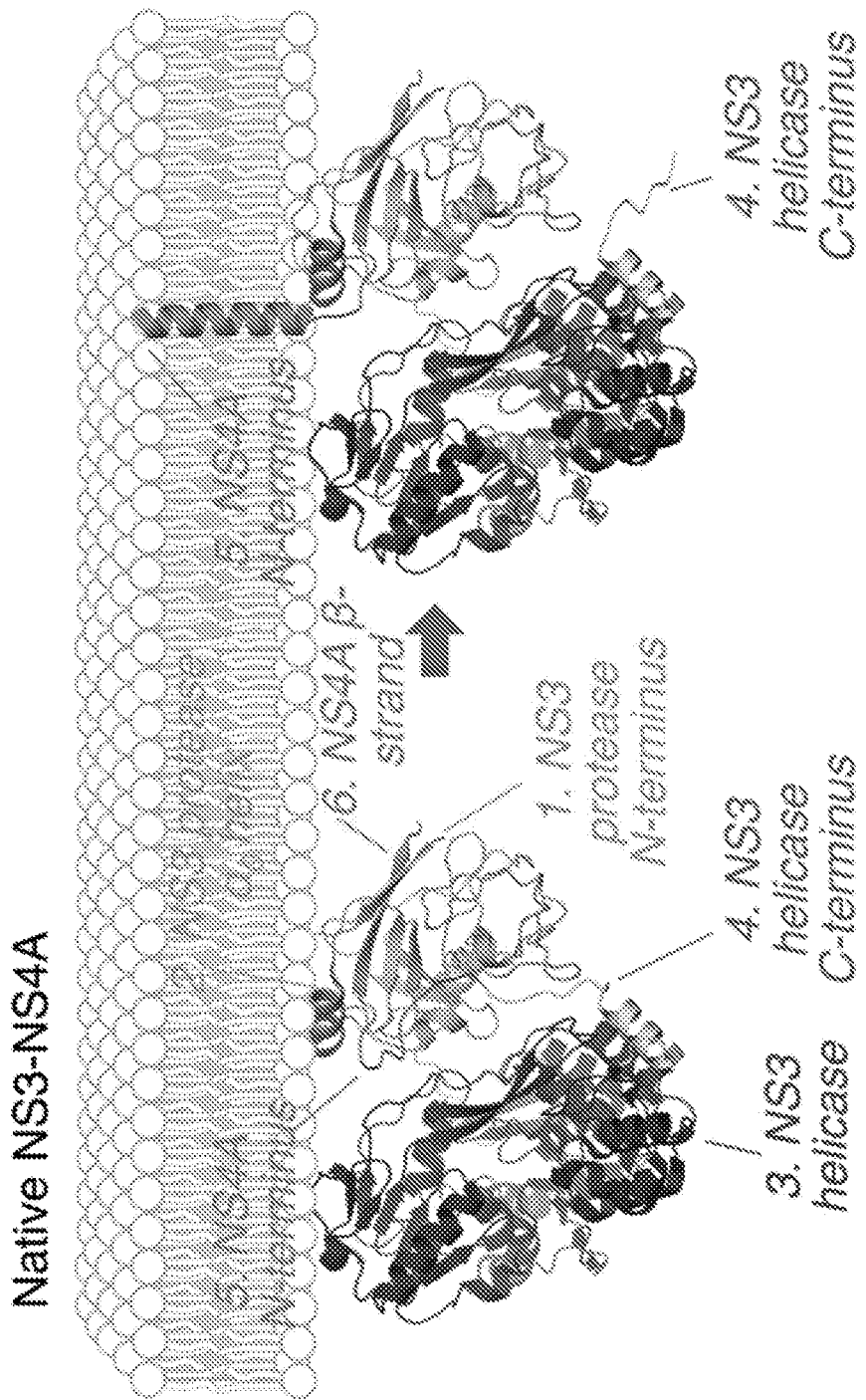
FIGS. 8A-8D show characterization of a degron contained in NS3pro-NS4A.
Figure 8B:
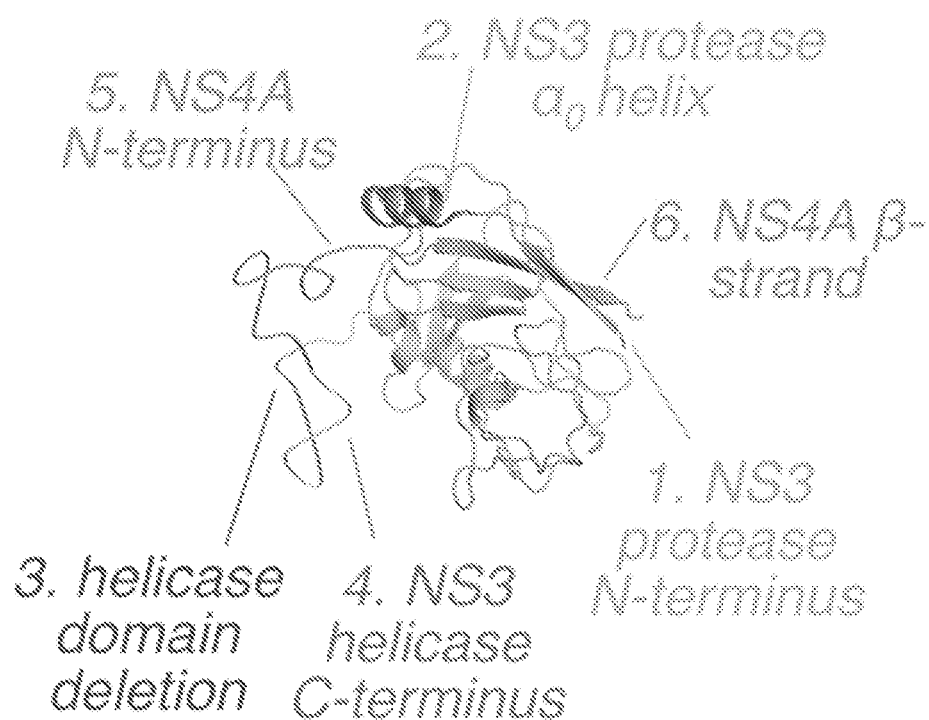

To explain the above results, we surmised that the arrangement of NS3pro and NS4A sequences in our construct had created a functional degron. During normal HCV replication, the free NS4A N-terminus forms a hydrophobic α-helix that is inserted into the endoplasmic reticulum membrane (Brass et al. (2008) Proc Natl Acad Sci USA 105:14545-14550) (FIG. 8A), while a β-strand C-terminal to this helix forms a complex with NS3pro, enhancing its catalytic activity and tethering it to the membrane. When the native full-length HCV nonstructural polypeptide is expressed, the NS4A N-terminus is created by cleavage at the NS3/4A junction (FIG. 8A). Despite NS3/4A not conforming to a consensus NS3 protease substrate sequence, cleavage is believed to occur due to its positioning in the NS3 protease active site by the adjacent NS3 helicase domain (Yao et al. (1999) Structure 7:1353-1363). However, as our engineered construct lacks the NS3 helicase domain, NS3/4A cleavage may be disfavored, and the entire NS4A sequence may remain fused to the NS3 protease without a free N-terminus (FIG. 8B). The hydrophobic sequences of NS4A, unable to insert into the membrane, might then exhibit degron-like activity.

Figure 1D:
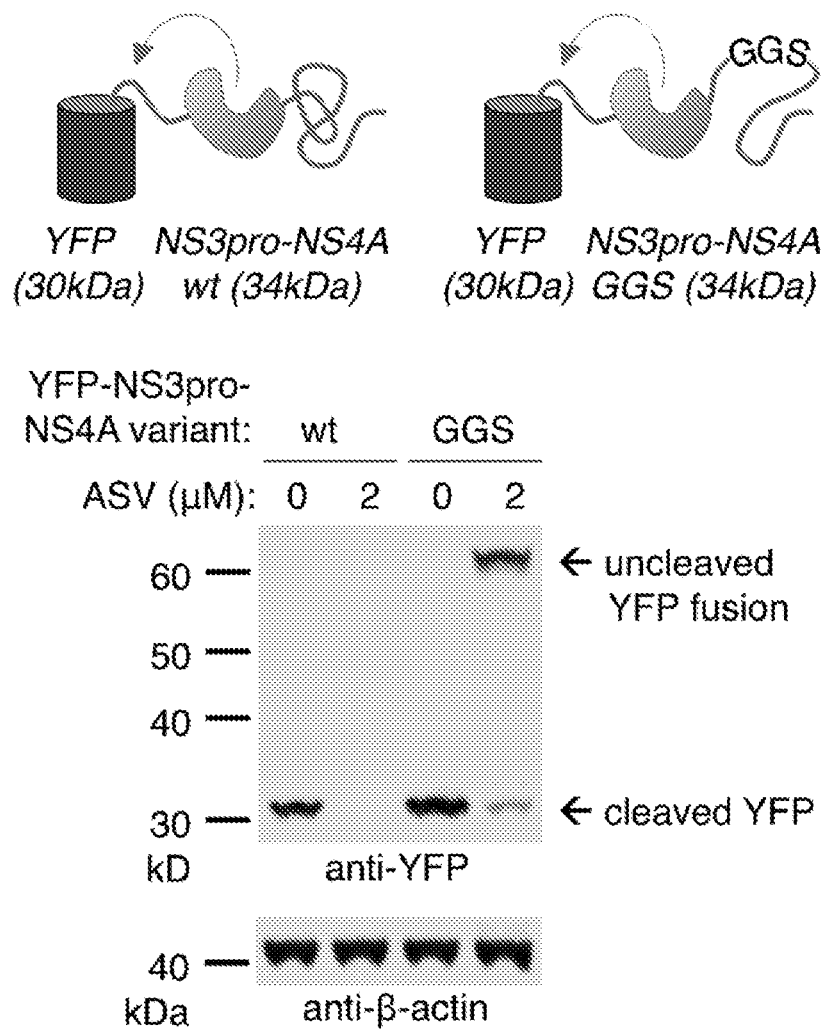

We tested the role of these putative destabilizing elements in suppressing expression of a yellow fluorescent protein (YFP) fused to the self-removing NS3pro-NS4A cassette. In the absence of asunaprevir, a 30-kDa YFP fragment was released as expected (FIG. 1D, lane 1). In contrast, with asunaprevir, virtually no full-length 64-kDa YFP-NS3pro-NS4A fusion was detected (FIG. 1D, lane 2), similar to the earlier observations with PSD95. Mutation of a 41-residue stretch comprising putatively unstructured sequence from NS3 helicase and hydrophobic sequence from NS4A (dotted line in FIG. 1B) to a glycine-serine linker of the same length rescued expression of the full-length protein in cells treated with asunaprevir to levels similar to YFP expressed in the absence of asunaprevir (FIG. 1D, lanes 3-4), indicating this region is essential for degron function. These results indicate that an unstructured, hydrophobic sequence derived from NS3 helicase and NS4A triggers rapid degradation of fused proteins.

Figure 8C:
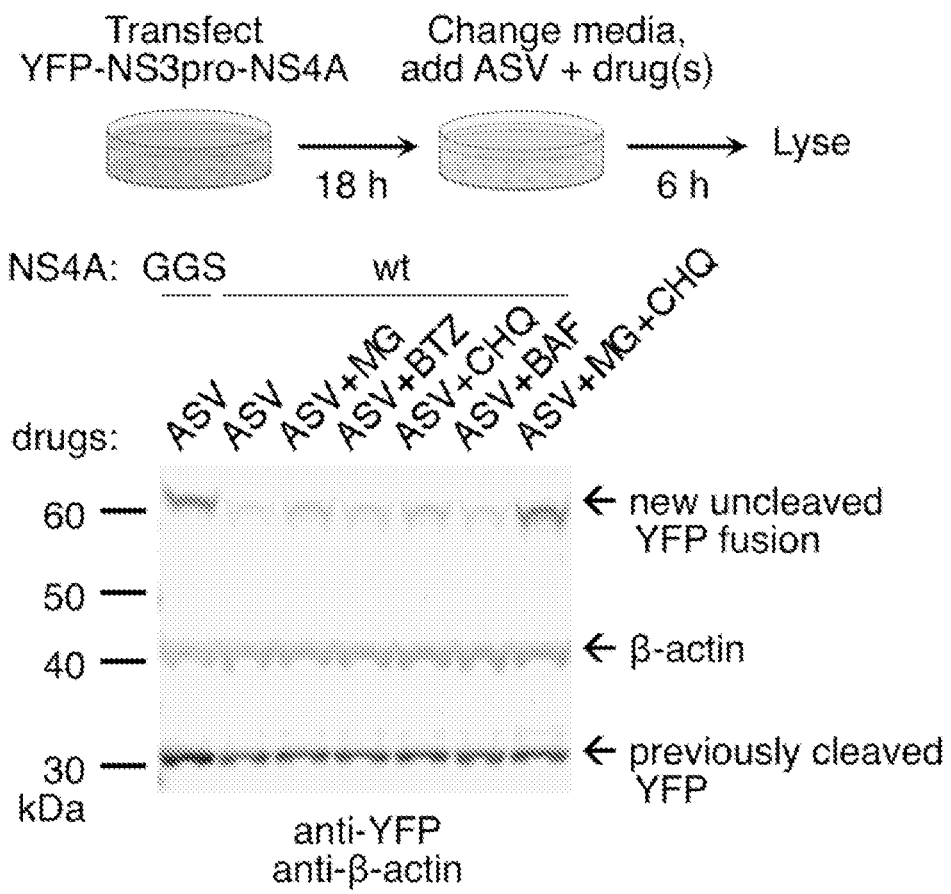
Figure 8D:
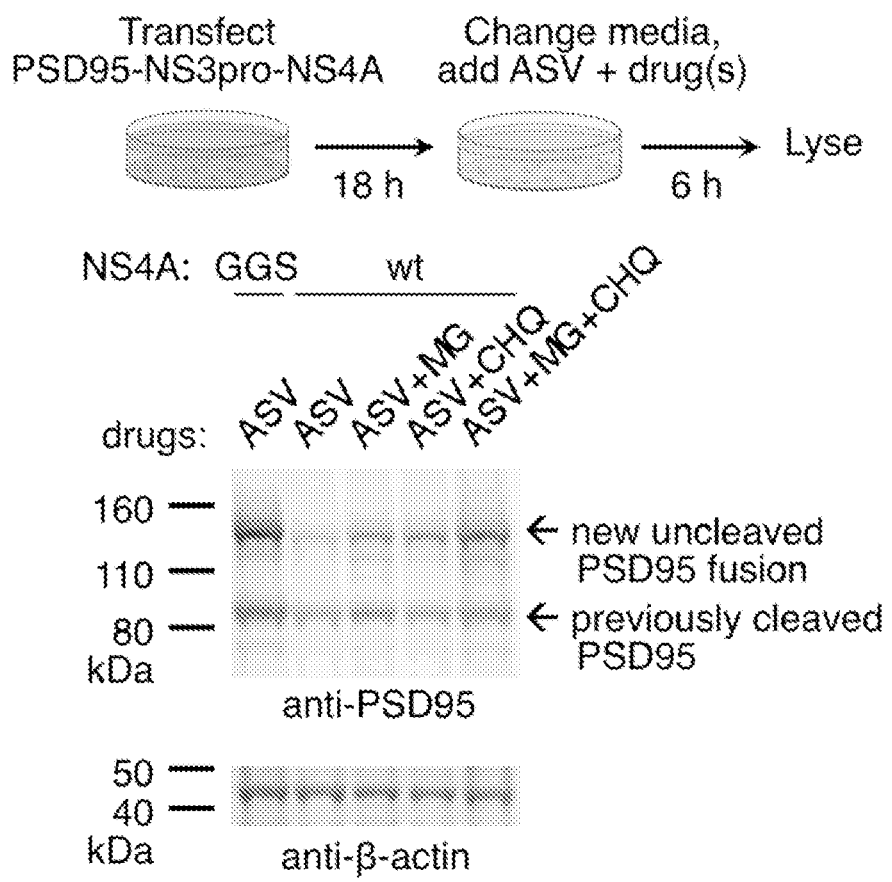

To determine which cellular proteolytic pathways were responsible for degrading NS3pro-NS4A fusions, we examined the effect of inhibiting proteasomes or autophagosomes. We allowed cells expressing YFP-NS3pro-NS4A to produce uncleaved YFP-NS3pro-NS4A in asunaprevir while applying inhibitors of proteasome or autophagosome degradation (FIG. 8C). Proteasome inhibition (by MG132 or bortezomib) or autophagy inhibition (by chloroquine or bafilomycin A1) each modestly increased YFP-NS3pro-NS4A protein levels (FIG. 8C, lanes 2-6). However, combined inhibition of the proteasome and the autophagosome (by MG132 and chloroquine) rescued YFP-NS3pro-NS4A expression to the same level as the mutant in which unstructured and hydrophobic amino acids were replaced with a glycine-serine linker (FIG. 8C, lanes 1 and 7). This effect was not restricted to YFP fusions, as a PSD95-NS3pro-NS4A fusion exhibited the same selective sensitivity to combined inhibition of the proteasome and autophagosome (FIG. 8D). The finding that only the combined blockade of both the proteasome and autophagy is able to significantly impede degradation suggests the strong possibility that the NS3pro-NS4A cassette harbors a bifunctional degron.

To summarize our results so far, proteins fused to the NS3 protease-NSA cassette via an intervening NS3 protease substrate sequence were well expressed in the absence of NS3 protease inhibitor at the size expected for released protein. By contrast, in the presence of NS3 inhibitor, steady-state levels of the fusion protein were drastically reduced, indicating that degradation occurred quickly enough to prevent the accumulation of newly synthesized proteins. This implies that fusion of a NS3pro-NS4A cassette with an intervening protease site would allow NS3 protease inhibitor application to effectively stop further protein production, as desired for our SMASh scheme (FIG. 1A). We thus designated the cassette comprising the NS3 protease domain, the NS4A protein, and a cis-cleavage site as a "SMASh tag".

SMASh Functions on Either Terminus

Figure 2B:
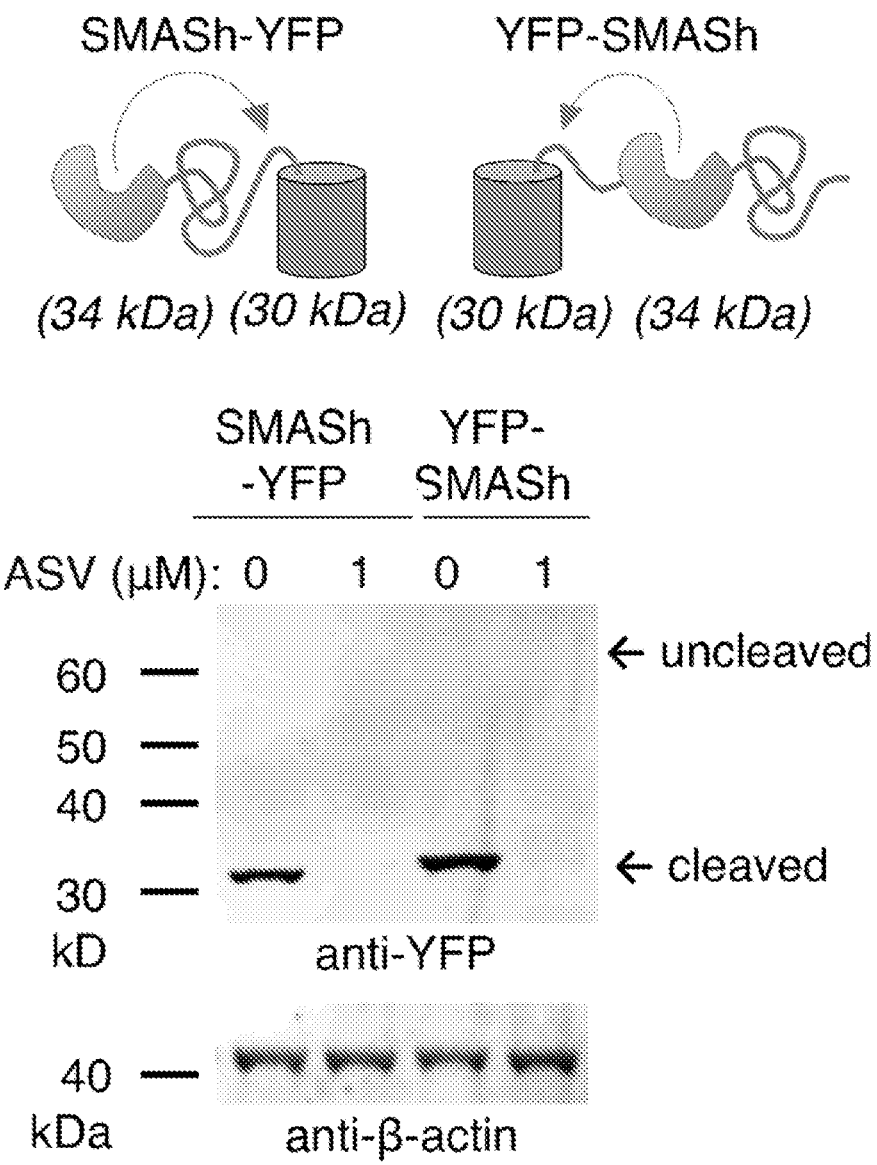
Figure 2C:
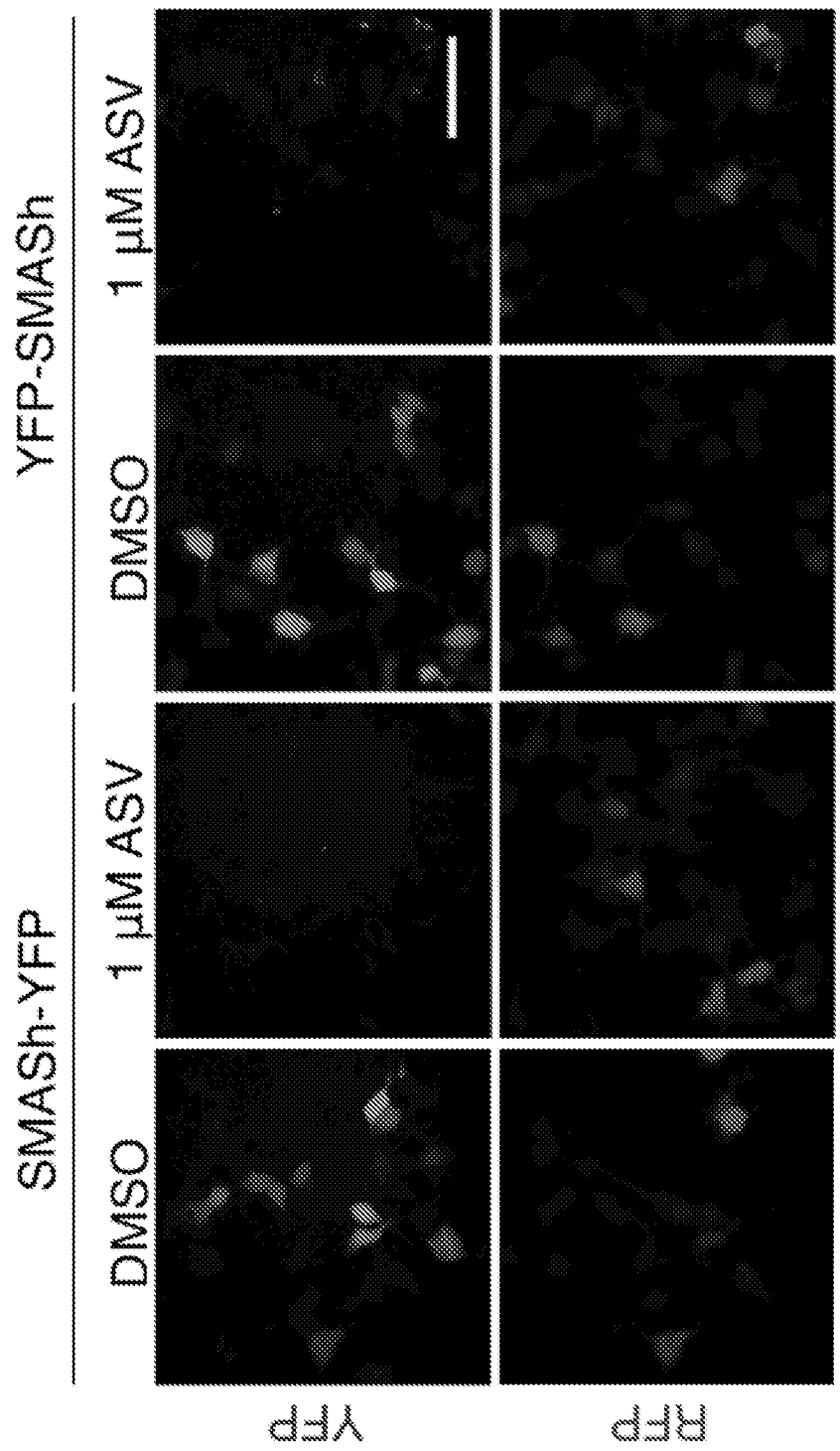
Figure 9A:
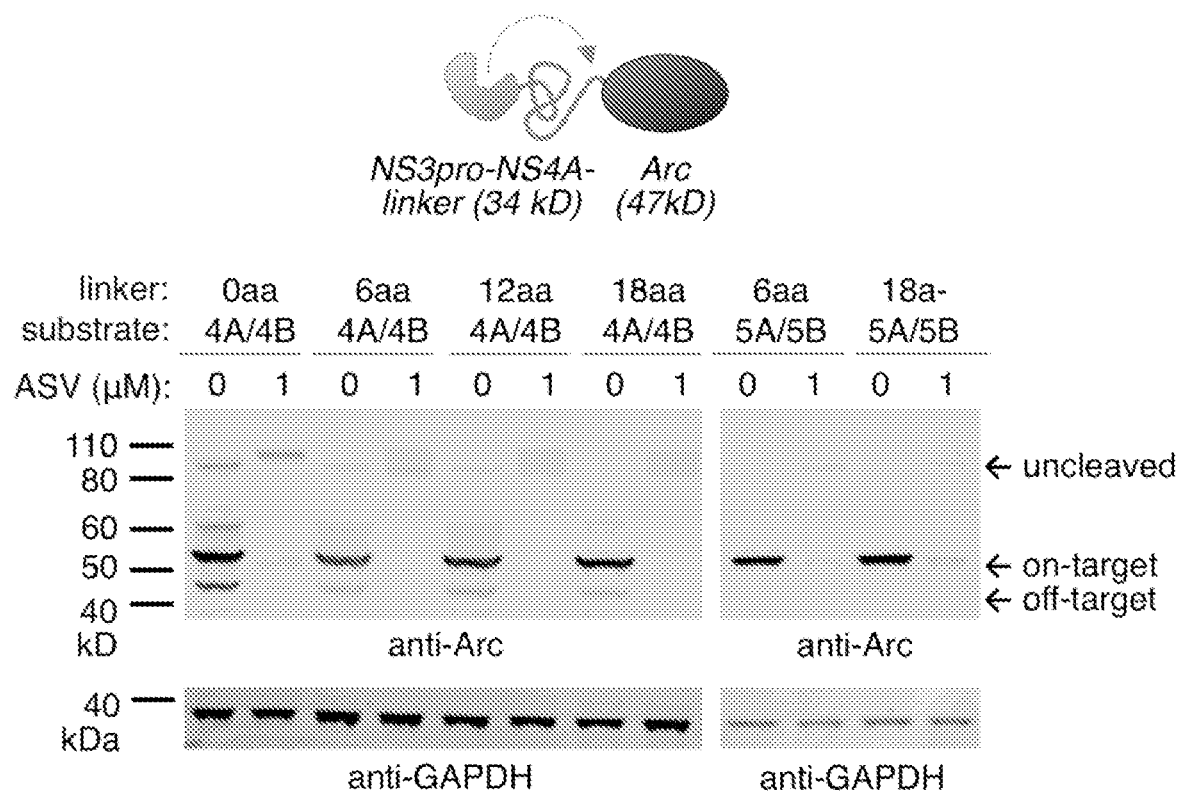
FIGS. 9A and 9B show optimization of an N-terminal SMASh tag.
Figure 9B:
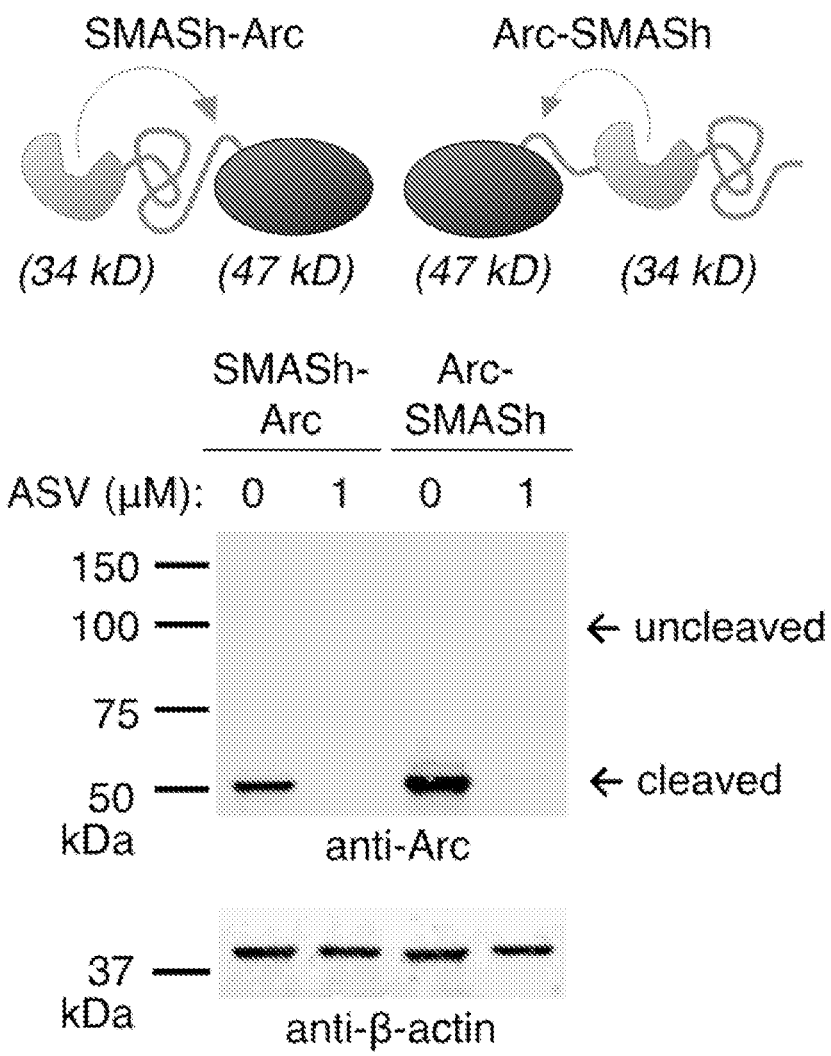

In the above constructs, the NS3 protease-NS4A cassette was fused at the C-termini of proteins and could remove itself via cleavage of a protease cleavage sequence from NS4A/4B in the linker. To create a self-removing degron that could be attached at either end of a protein of interest, we optimized the ability of a NS3 protease-NS4A cassette to remove itself from the N-terminus of the synaptic protein Arc. The incorporation of additional linker sequences and the use of the NS5A/5B protease cleavage site proved optimal for self-removal of the tag while preserving drug responsiveness (FIG. 9A). The final N-terminal SMASh tag (FIG. 2A) regulated Arc production with similar efficacy to the original C-terminal SMASh tag (FIG. 9B). To further confirm that the SMASh tag confers robust control of protein expression by drug when placed at either the N- or C-terminus of a protein, we coexpressed SMASh-YFP or YFP-SMASh in HEK293 cells with a red fluorescent protein (RFP) derived from mNeptune2 (Chu et al. (2014) Nat Methods 11:572-578) as a control. In the absence of NS3 protease inhibitor, YFP was liberated as a single species of the expected size from either N-terminal or C-terminal fusions, while both cleaved and full-length protein were significantly reduced in the presence of asunaprevir (FIG. 2B). Imaging of YFP fluorescence in living cells confirmed this effect, as YFP was nearly undetectable in the presence of asunaprevir (FIG. 2C). There was no difference in RFP expression, showing the selectivity of asunaprevir for the SMASh-tagged target protein.

Figure 3A:
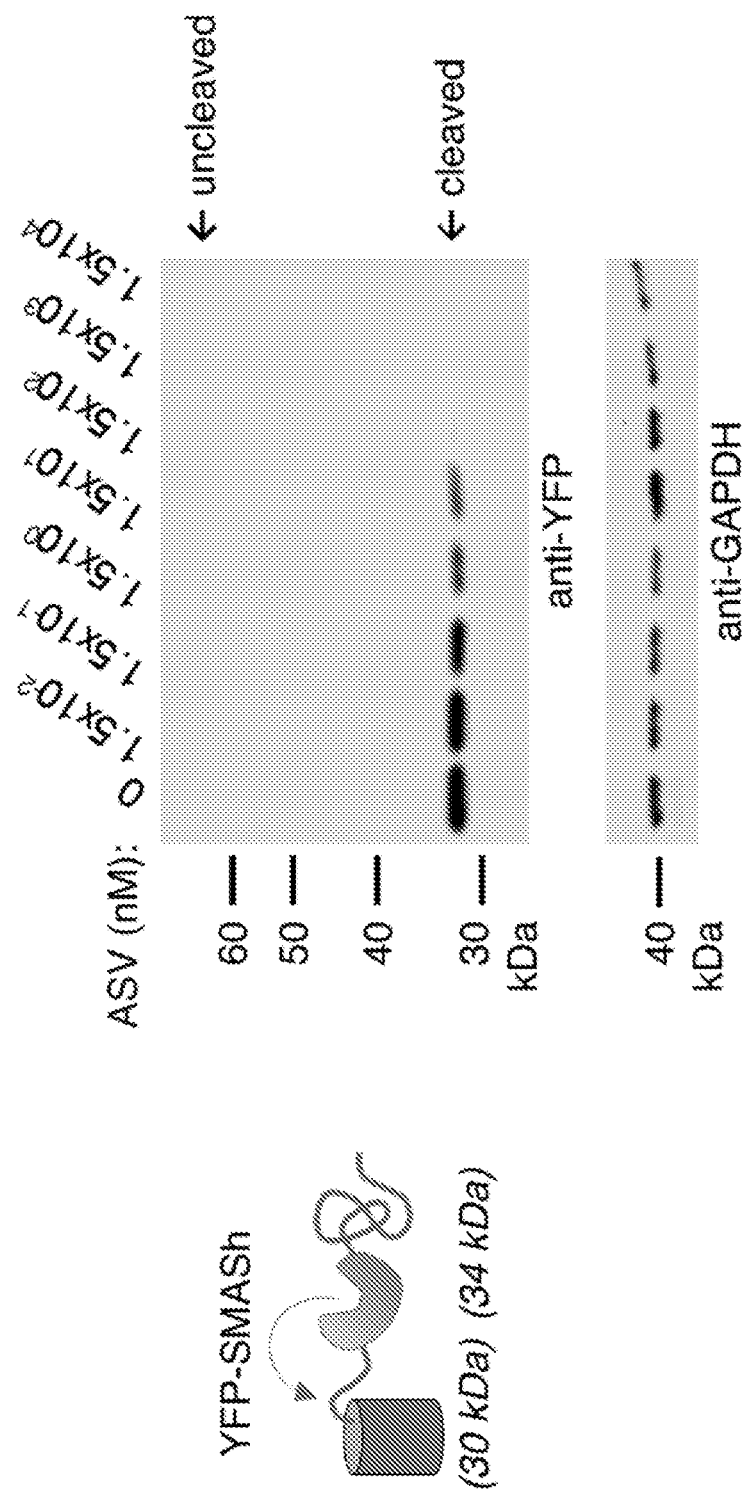
FIGS. 3A-3D show that protein regulation by SMASh-tagging is dose-dependent and reversible.
Figure 3B:
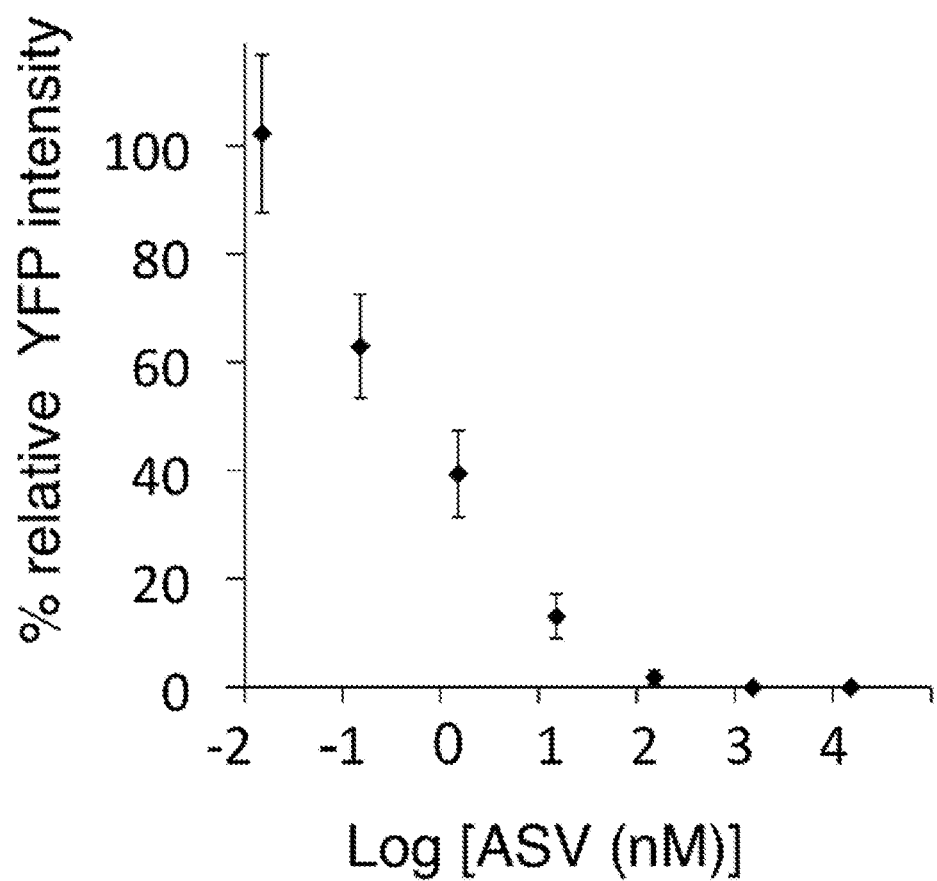

SMASh Allows Tunable and Reversible Control of Protein Expression with Rapid Onset To determine whether SMASh allows tunable control of protein levels, we treated cells expressing YFP-SMASh with asunaprevir at various concentrations from 15 pM to 15 μM. YFP levels were regulated by asunaprevir in a clear dose-dependent manner (FIG. 3A), with YFP intensity related to the log of drug concentration (FIG. 3B). The 50% effective concentration ($EC_{50}$) of asunaprevir as measured by YFP suppression was approximately 1 nM, comparable to the $EC_{50}$ in HCV replicon assays (McPhee et al, supra), demonstrating that the SMASh construct design does not significantly change asunaprevir binding to NS3 protease. Notably, YFP was undetectable with asunaprevir at 1.5 μM, a concentration at which it exhibits no activity against a panel of cellular proteases and is not cytotoxic (McPhee et al, supra). Asunaprevir also achieved protein repression to 1.9% of undrugged levels at 150 nM, a concentration that can be maintained in plasma and organs for hours following oral ingestion of therapeutic non-toxic doses in humans, dogs, and rodents (McPhee et al, supra; Eley et al. (2013) Clin Pharmacol Drug Dev 2(4):316-327; Yuan et al. (2013) J Chromatogr B Analyt Technol Biomed Life Sci 921-922: 81-86). Thus SMASh-mediated repression is tunable across a dynamic range of greater than 50-fold using drug concentrations that are non-toxic and achievable in vivo in mammals by oral administration.

Figure 10A:
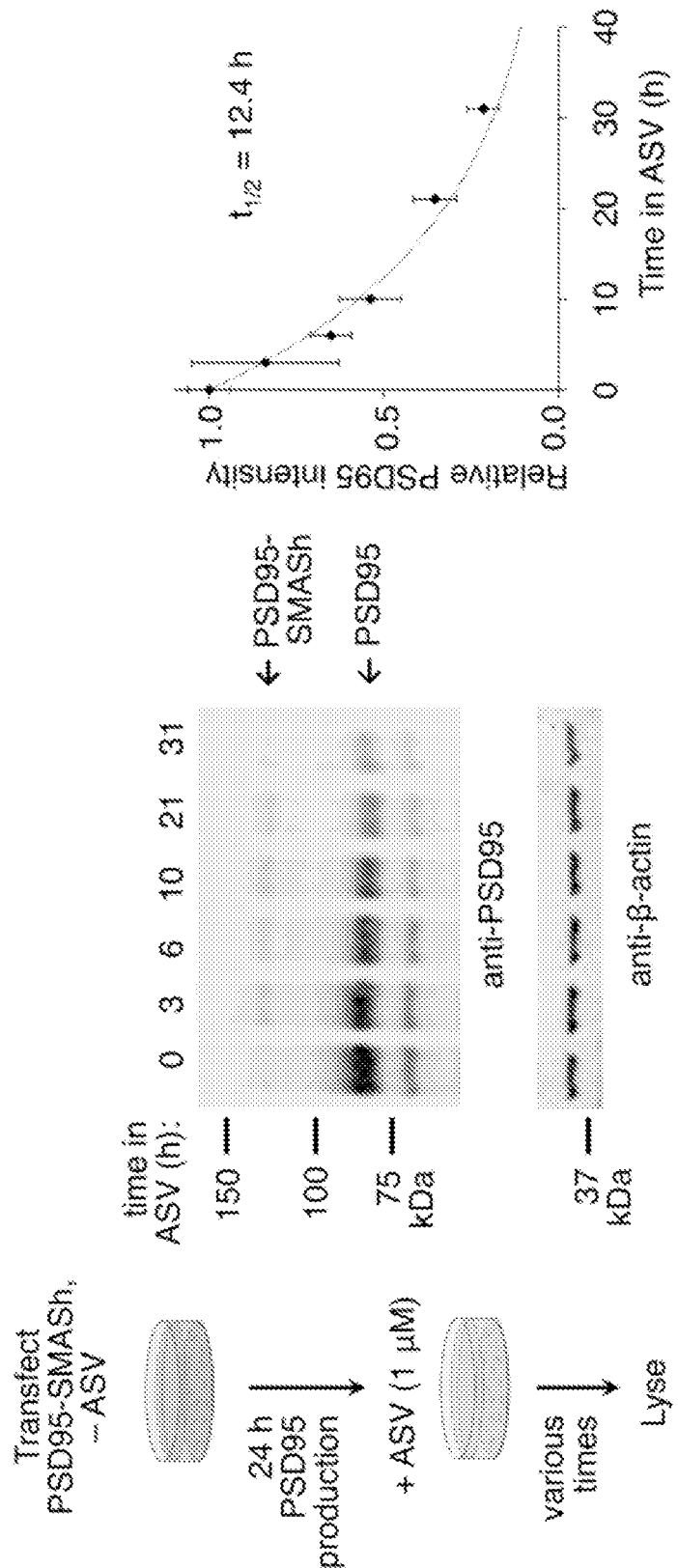
FIGS. 10A and 10B show that SMASh accelerates degradation of the long-lived protein PSD95 by 12-fold.
Figure 10B:
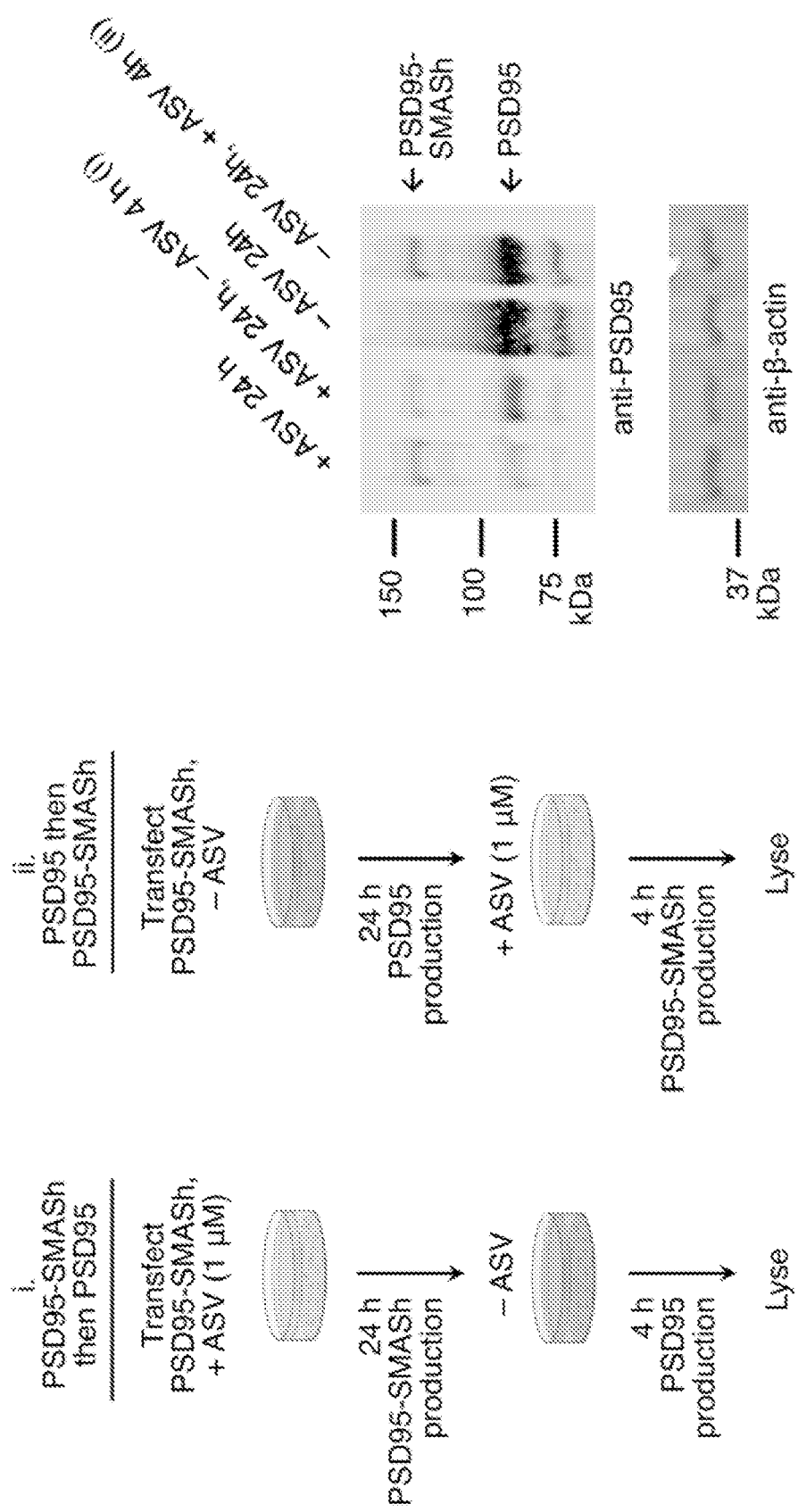
Figure 11A:
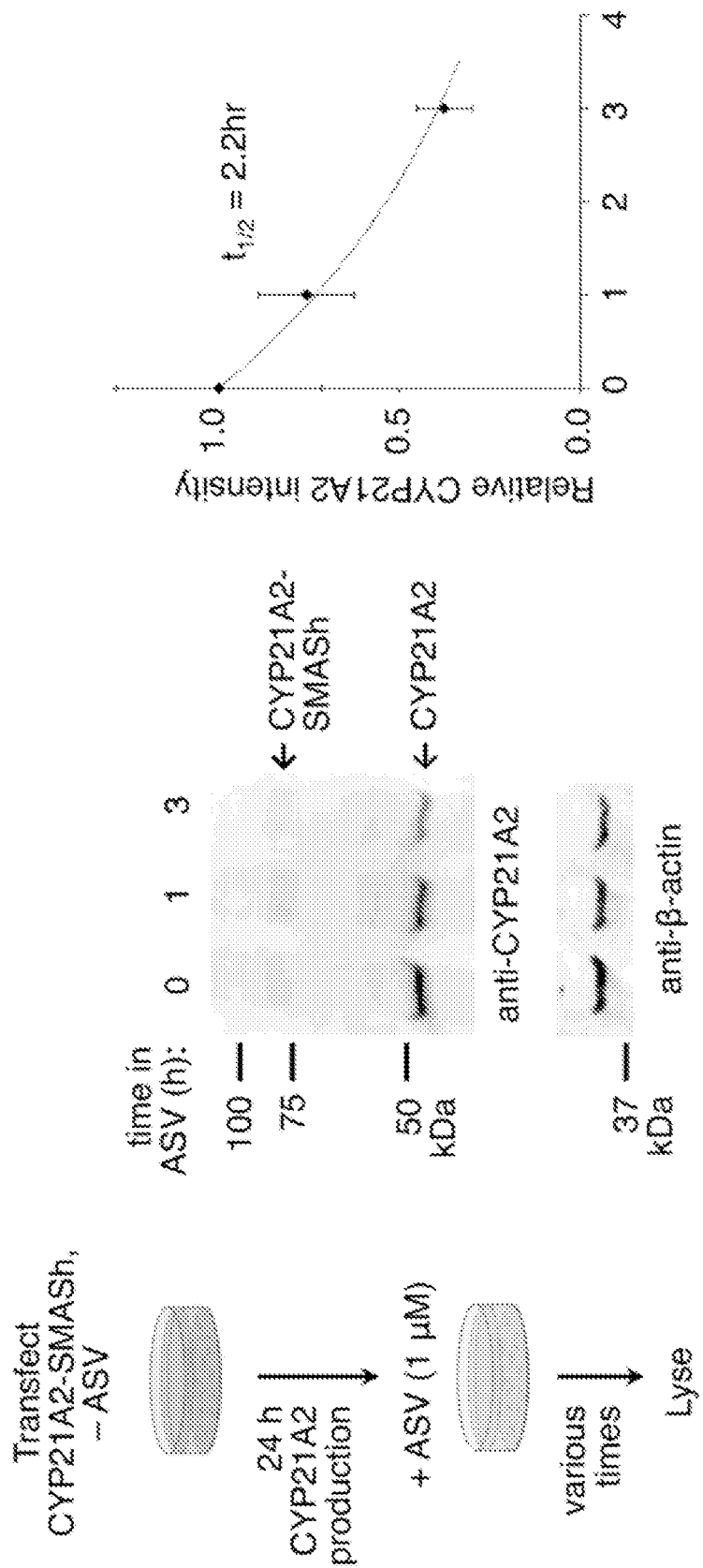
FIGS. 11A and 11B show that SMASh accelerates degradation of the short-lived protein CYP21A2 by 9-fold.
Figure 11B:
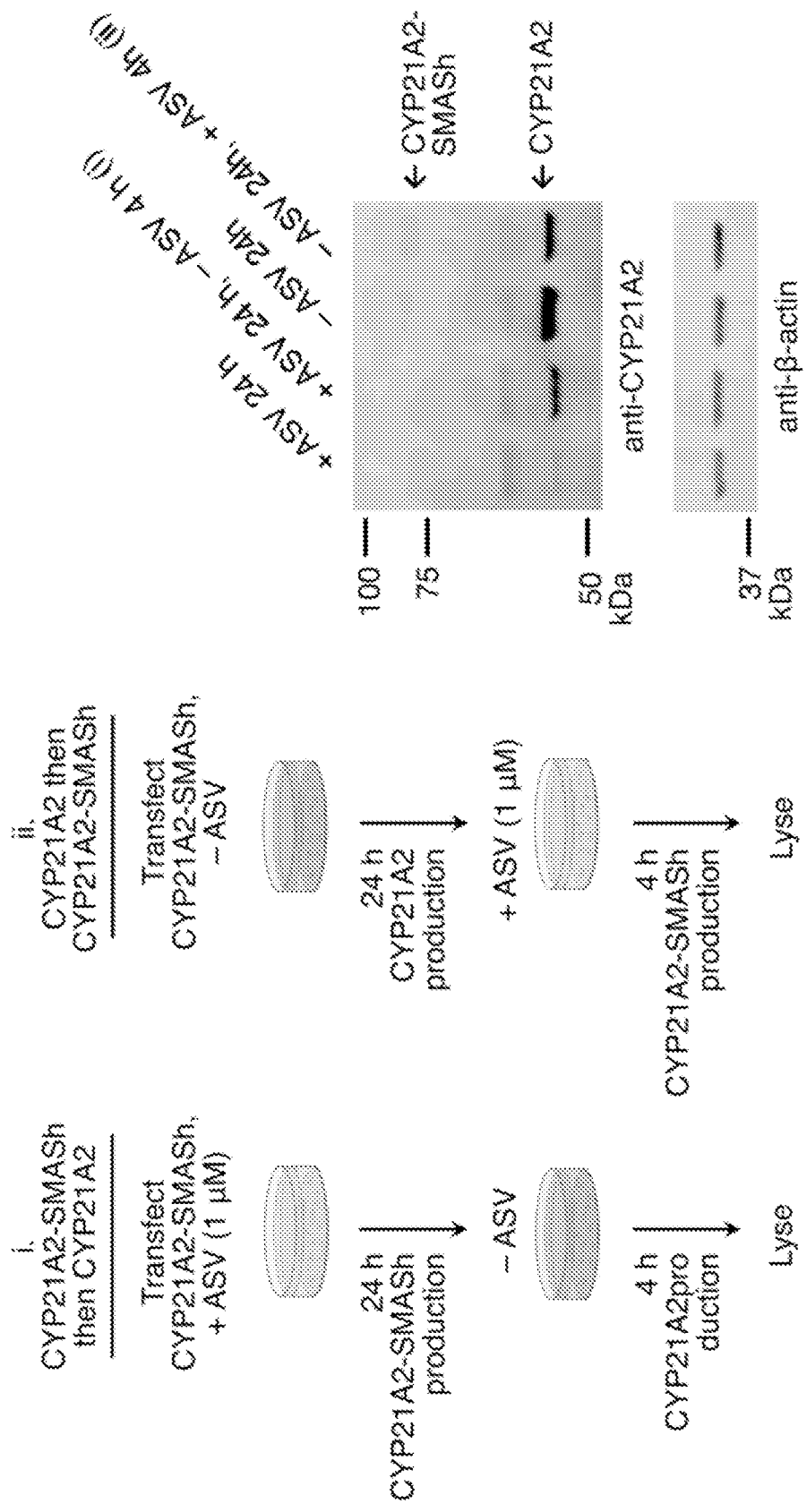

Because HCV protease inhibitor prevents accumulation of new protein copies without affecting old copies, the overall levels of a protein of interest following shutoff depend on its degradation rate. Interestingly, SMASh allows for the easy measurement of protein half-lives, as the liberated species is no longer produced after addition of saturating amounts of drug, and its decay can thus be followed by immunoblotting. We used this method to measure the half-lives in HEK293 cells of the relatively long-lived and short-lived proteins PSD95 and CYP21A2, respectively, as 12.4 hours and 2.2 hours (FIGS. 10A, 11A). This procedure is similar to how cycloheximide is often used to block all protein synthesis and allow the measurement of protein half-lives by following their decay, but in contrast to cycloheximide, SMASh-mediated shutoff is specific to the tagged protein of interest. Next, we characterized how quickly proteins with a retained SMASh tag are degraded compared to their untagged state. Using a simple mathematical model to relate observed relative abundances of protein species to their measured synthesis and degradation rates (Methods), we found that the SMASh tag reduced the half-life of PSD95 from 12.4 hours to 1.1 hours (FIG. 10B) and of CYP21A2 from 130 minutes to 15 minutes (FIG. 11B).

Figure 3C:
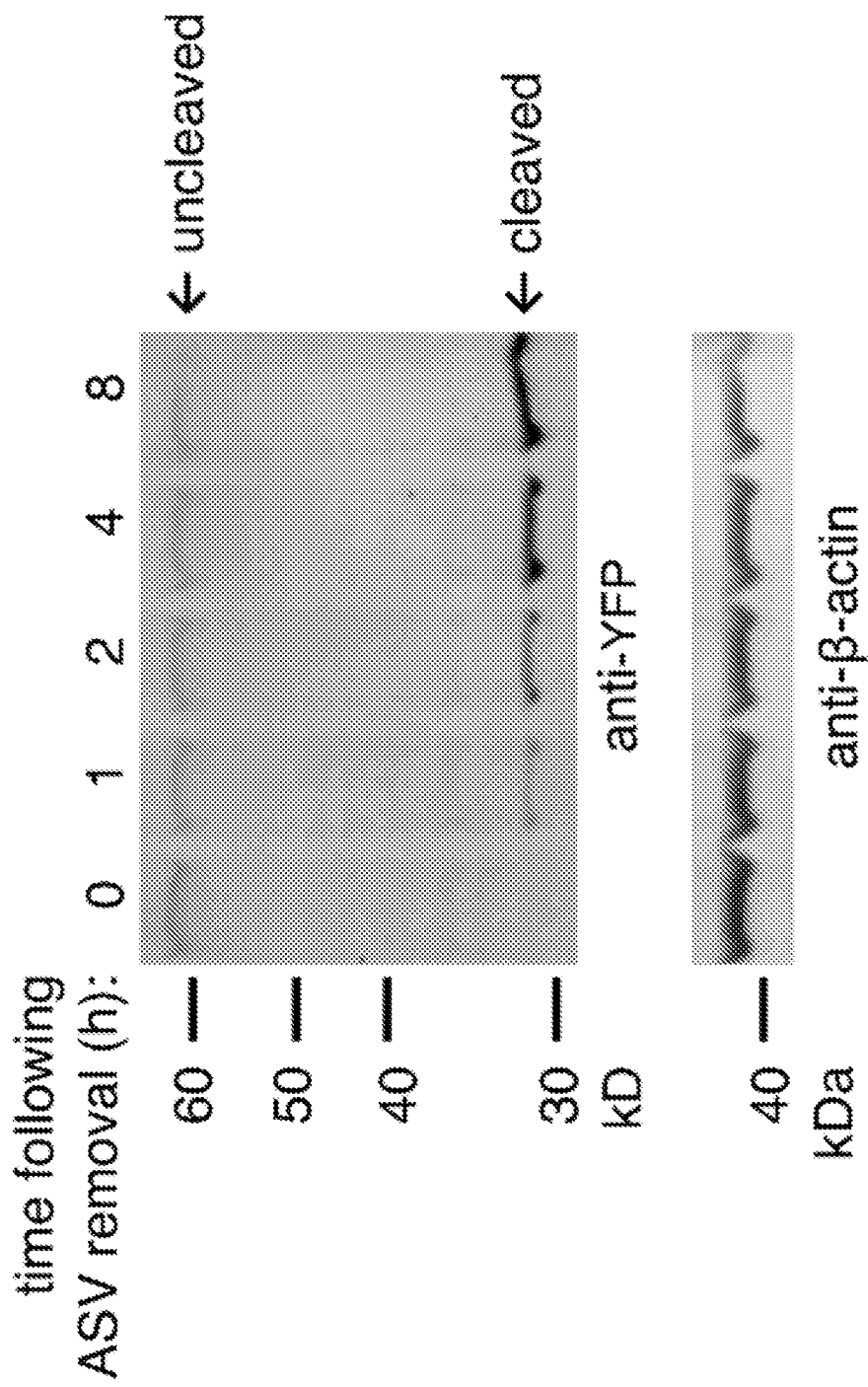
Figure 3D:
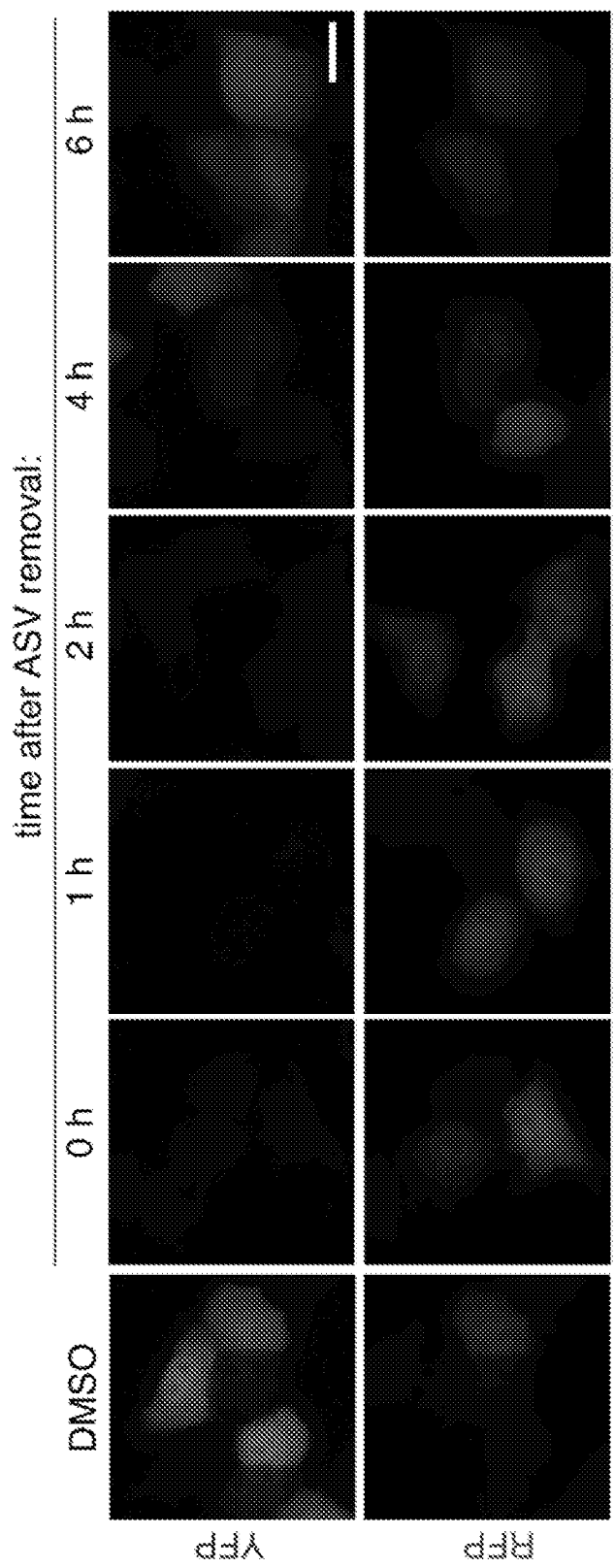

As mRNA transcripts encoding SMASh-regulated proteins are not expected to be affected by protease inhibitor treatment, protein shutoff by SMASh should be readily reversible upon drug removal. To test this, we incubated HeLa cells expressing YFP-SMASh for 12 hours post-transfection in the presence of asunaprevir to ensure total initial shutoff. Then, after drug washout, we followed the appearance of YFP signal over time. By immunoblotting, YFP signal appeared 1 hour after washout (FIG. 3C). By live-cell fluorescence microscopy, YFP signal was visible at 2 hours after washout, and by 6 hours fluorescence intensity approximated that of cells cultured in parallel for 12 hours without asunaprevir (FIG. 3D). The delay in appearance of YFP signal in microscopy relative to immunoblotting is attributable to the time course of maturation of the YFP chromophore, whose time constant of maturation has been measured to be 40 minutes (Iizuka et al. (2011) Anal Biochem 414:173-178).

Taken together, our results demonstrate that the SMASh system can control protein expression in a dose-dependent and reversible manner by causing rapid degradation of tagged proteins synthesized in the presence of drug. Recovery of protein expression after drug removal is rapid as mRNA pools are not depleted, which can be beneficial when fast onset of protein production is required.

SMASh Functions on Multiple Protein Types and in Neurons

Figure 4A:
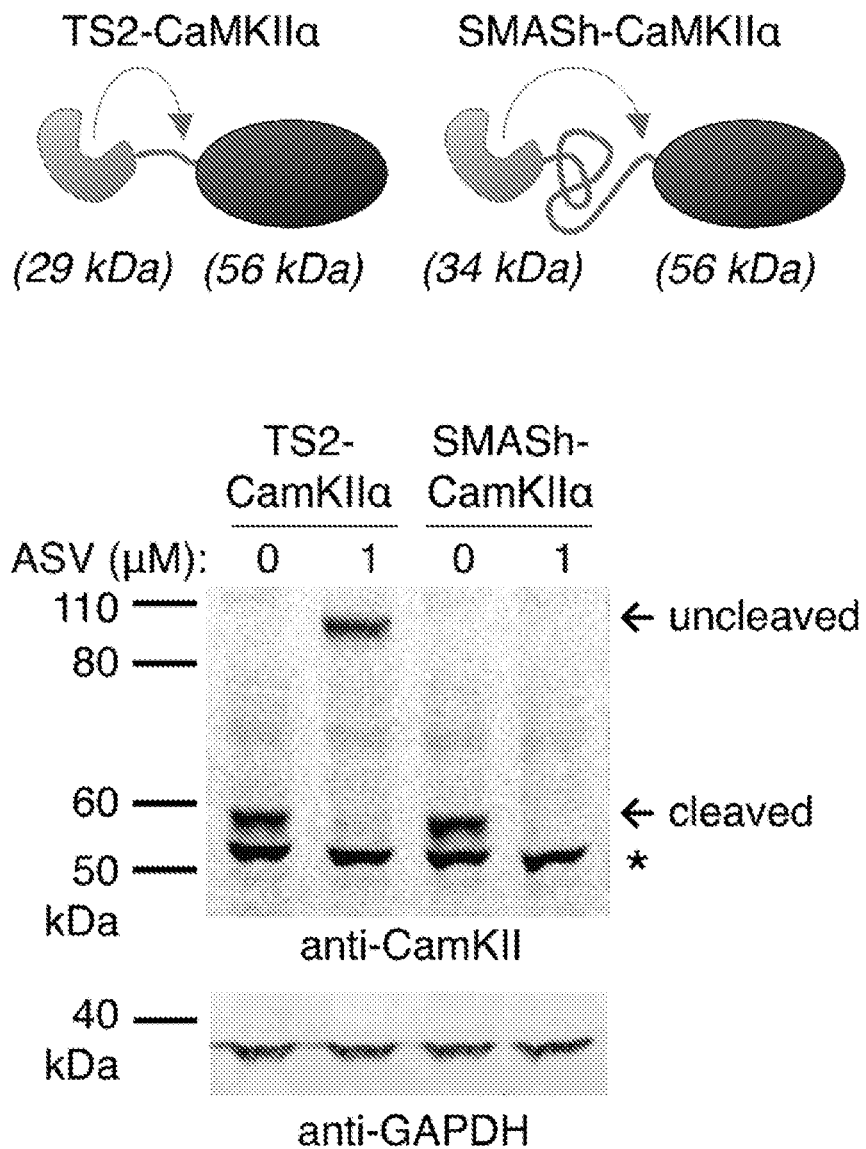
FIGS. 4A-4C show that SMASh functions on a variety of proteins.
Figure 4B:
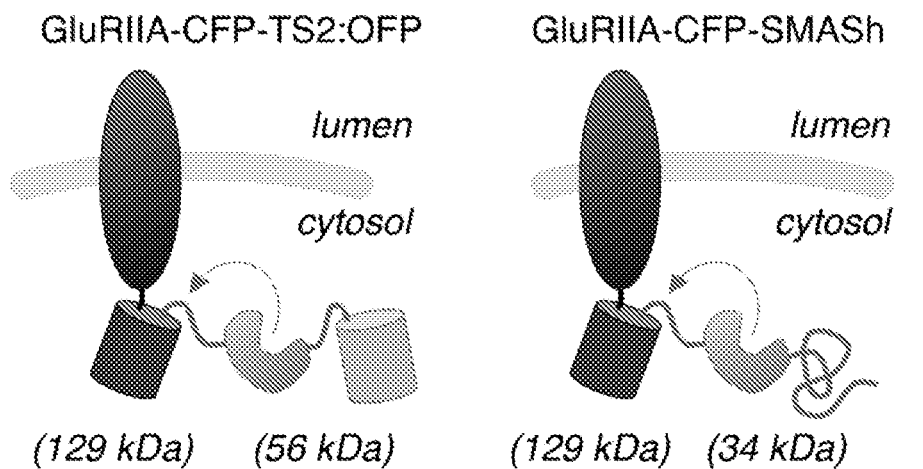
Figure 4B:
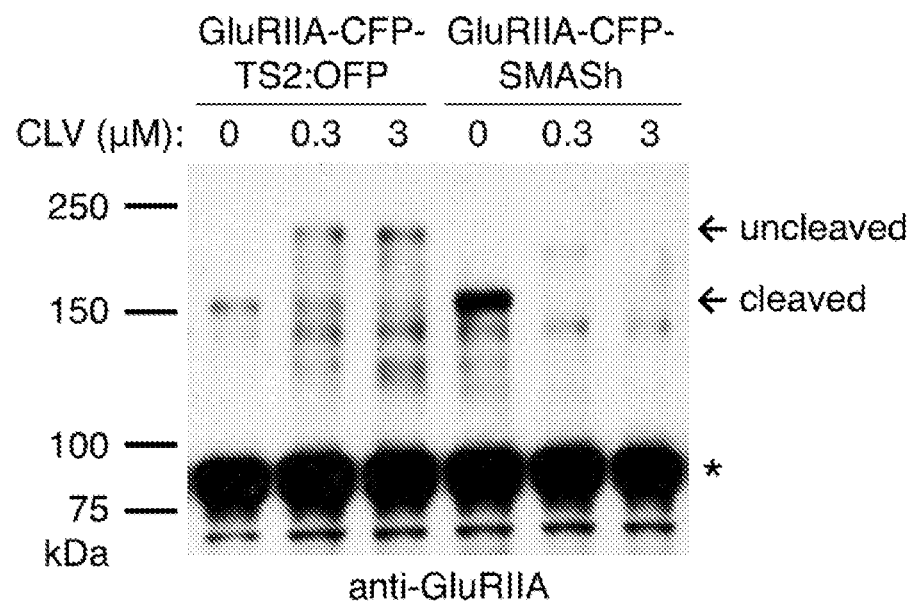
Figure 4C:
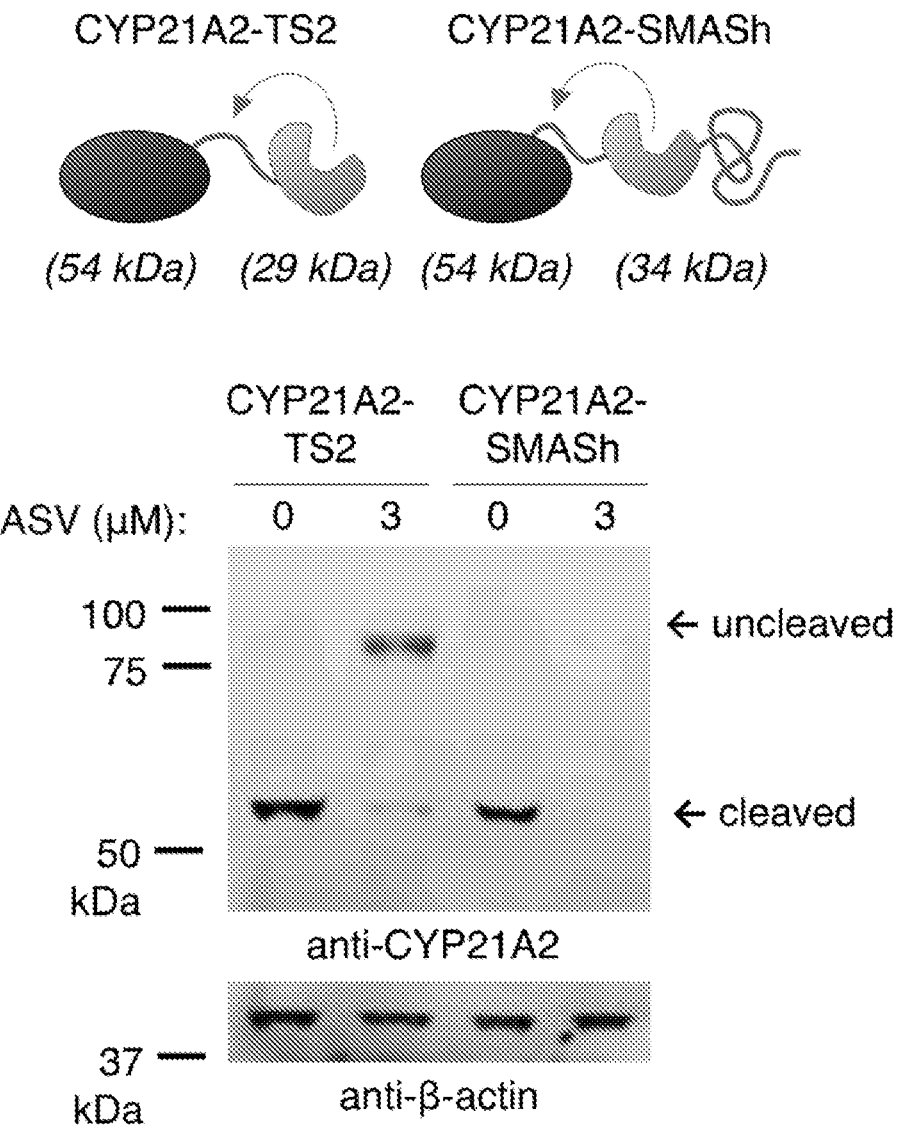

We next determined if SMASh can control production of a variety of protein types. SMASh was able to control the production of a multimeric enzyme, calcium/calmodulin activated protein kinase II α (FIG. 4A), and of a multi-pass transmembrane protein, the *Drosophila* GluRIIA glutamate receptor (FIG. 4B). Additionally, SMASh is also capable of suppressing the expression of a short-lived protein, CYP21A2 (half-life ~2 hours, FIG. 4C). Thus, for the six proteins of various sizes and structures which we tested—PSD95, YFP, Arc, CaMKIIα, GluRIIA and CYP21A2—the SMASh tag was able to confer robust drug inhibition of protein production in all cases.

Synthesis of specific proteins is tightly regulated by growth factors and synaptic activity in neurons, where it is required for long-lasting cellular changes that support memory formation. As our previous experiments using SMASh were only performed in proliferating cell types, we therefore investigated whether SMASh could function in post-mitotic neurons as well. We indeed observed that SMASh conferred drug control over the production of YFP in primary cultures of rat and mouse cortical/hippocampal neurons (FIGS. 12A and 12B).

SMASh Functions in Yeast

We next investigated whether the SMASh tag could enable pharmacological control of protein production in the budding yeast *S. cerevisiae*. Yeast genes can be transcriptionally regulated by substituting drug-responsive promoters for endogenous promoters, but this requires expression of an exogenous transcription factor from another gene and does not preserve endogenous patterns of transcriptional regulation (Mnaimneh et al. (2004) Cell 118(1):31-44). Yeast protein stability can be regulated by a temperature-sensitive degron, but this induces a heat shock response and requires switching growth media (Morawska et al. (2013) Yeast 30:341-351). Researchers have therefore also attempted to regulate protein expression in yeast by controlling protein stability with drugs. The only chemical assisted method that has been successfully adapted to yeast is the auxin-induced degradation (AID) method, which involves attaching proteins of interest to a domain that recruits an ubiquitin ligase in an auxin-dependent manner (Morawska et al., supra; Nishimura et al. (2009) Nat Methods 6:917-922). However, AID requires both permanent tagging of the protein of interest and expression of a second transgene, and can exhibit premature auxin-independent degradation or incomplete auxin-dependent degradation (Morawska et al., supra). Thus, a method for drug regulation of protein production that is both simple and robust is still lacking in yeast.

Figure 5A:
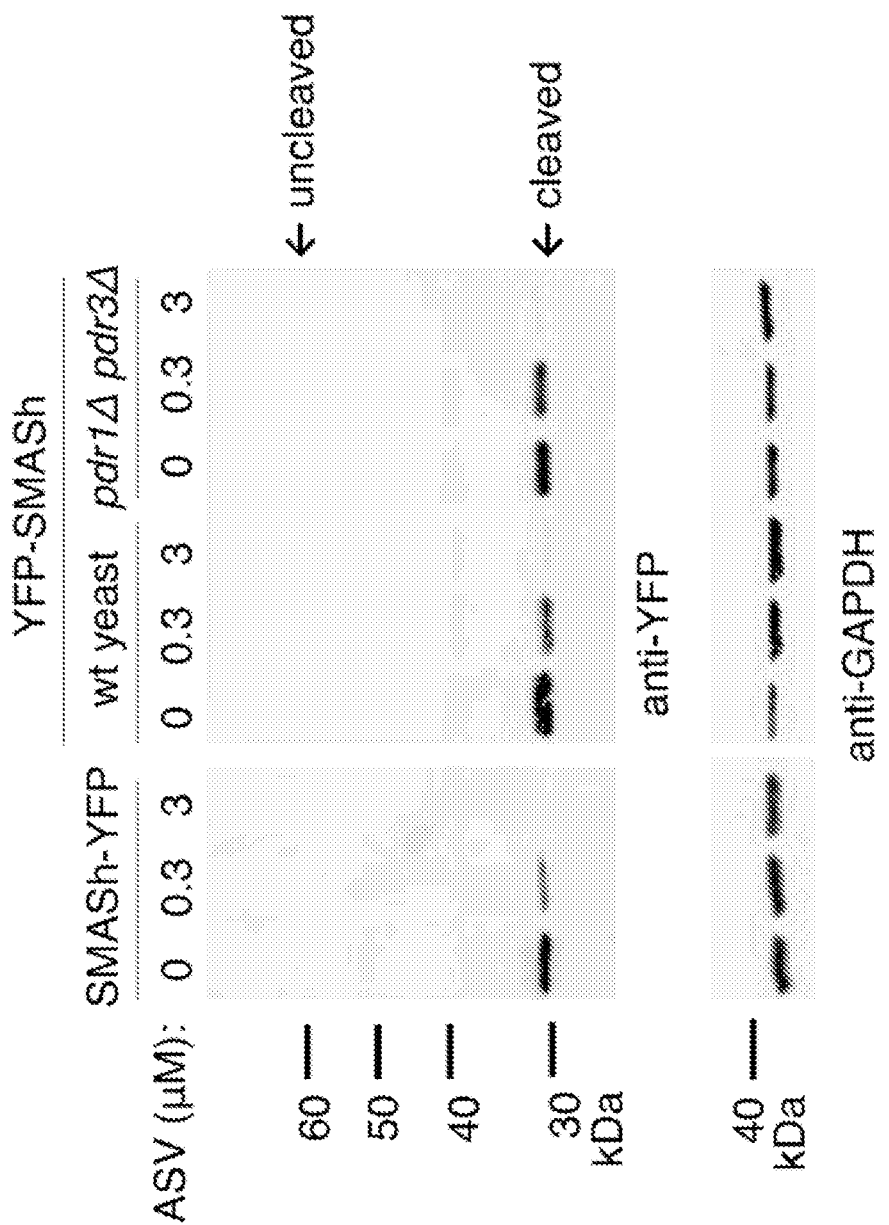
FIGS. 5A-5C show that SMASh functions in budding yeast.
Figure 5B:
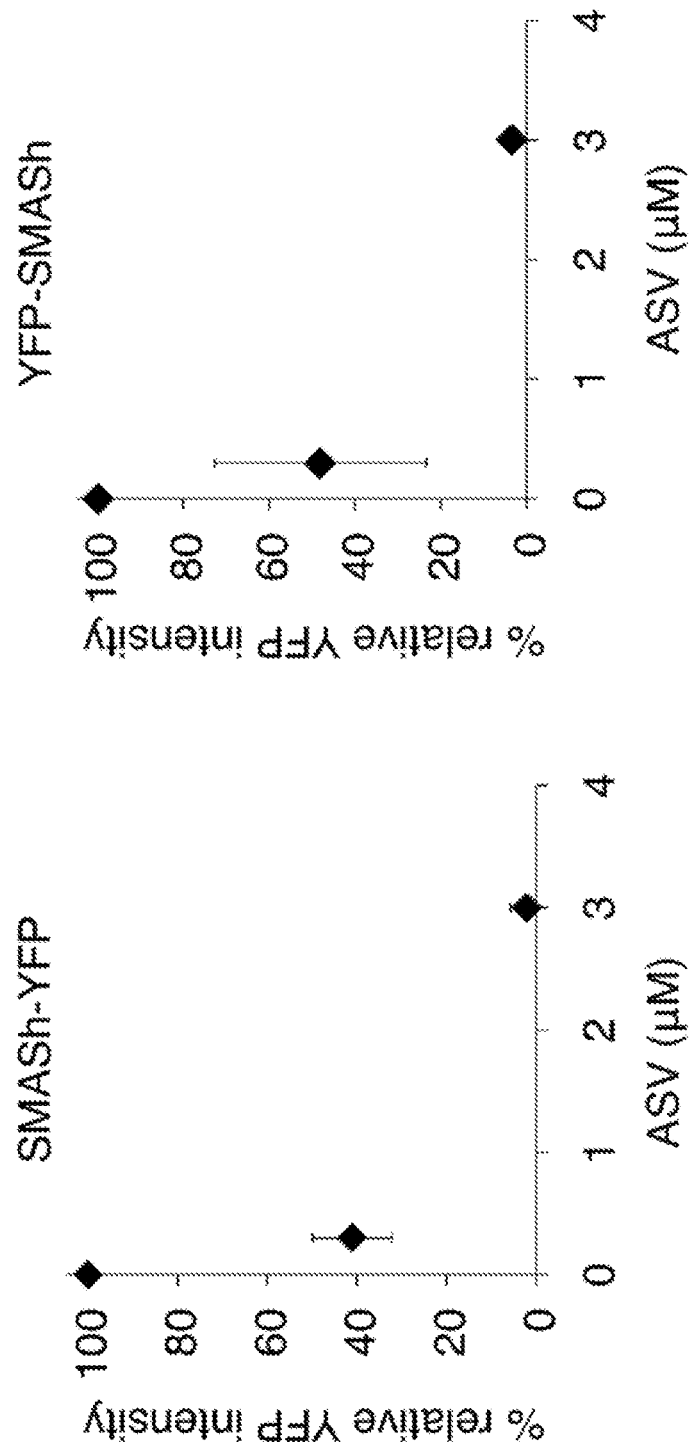
Figure 5C:
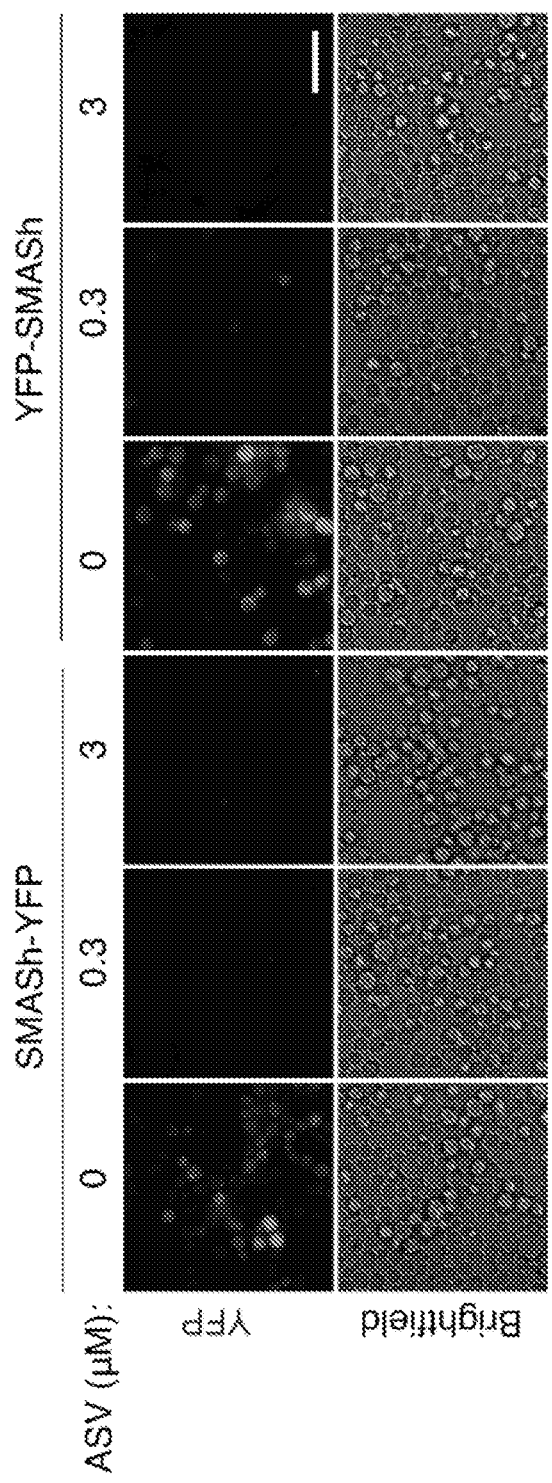

When expressed in yeast from an episomal gene, we found the C-terminal SMASh tag with a protease cleavage site of sequence DEMEEC/S was able to confer drug repression on YFP expression, similarly to its performance in mammalian cells (FIG. 5A, lane 4-6). However, the N-terminal SMASh tag and fast-cleaving site (EDVVPC/S) used in mammalian cells allowed leaky expression of YFP in yeast in the presence of drug (data not shown). Changing the fast protease cleavage site to a slower-cleaving site, DEMEEC/S, fixed this problem (FIG. 5A, lane 1-3), consistent with HCV protease being more active at the lower temperatures of yeast compared to mammalian cells. SMASh was able to repress YFP expression to undetectable levels at 3 µM asunaprevir (FIGS. 5A-5C). We also tested a strain lacking the Pdr1 and Pdr3 transcriptional activators of drug efflux pumps (Su et al. (2010) Dis Model Mech 3:194-208) to see if drug doses can be further lowered, but found no effect (FIG. 5A, lane 7-9). These results demonstrate that SMASh confers drug-mediated control of protein expression in yeast using micromolar concentrations of drug. To the best of our knowledge, SMASh is the first method that uses a single genetic element to impose drug control over the expression of specific proteins in yeast.

Figure 6A:
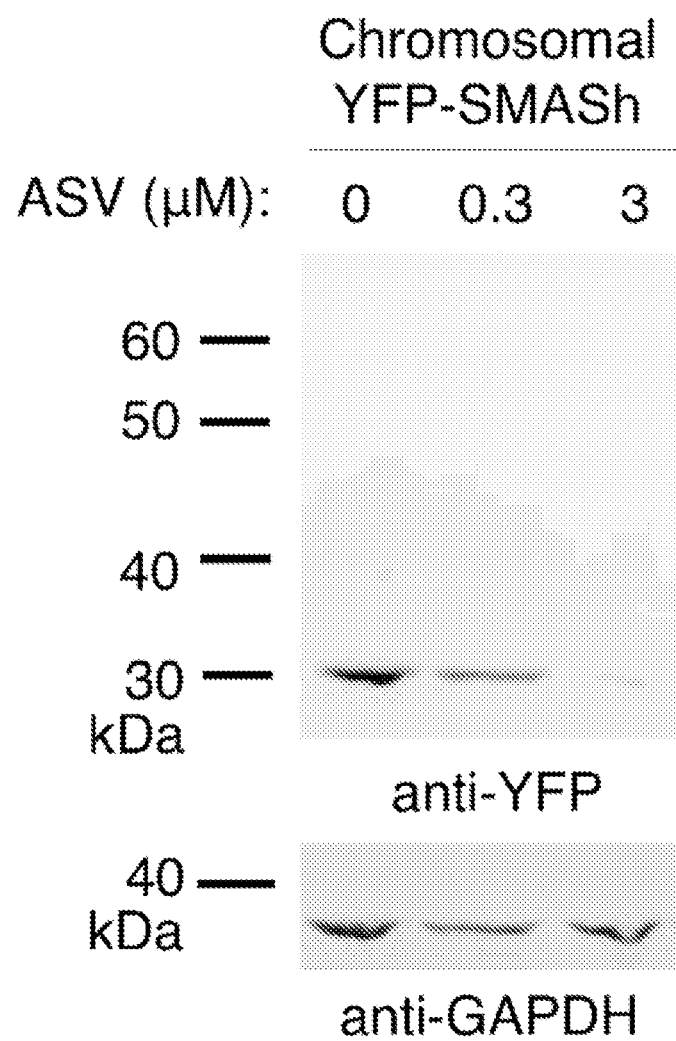
FIGS. 6A-6D show that SMASh mediated drug control of chromosomal protein production.
Figure 6B:
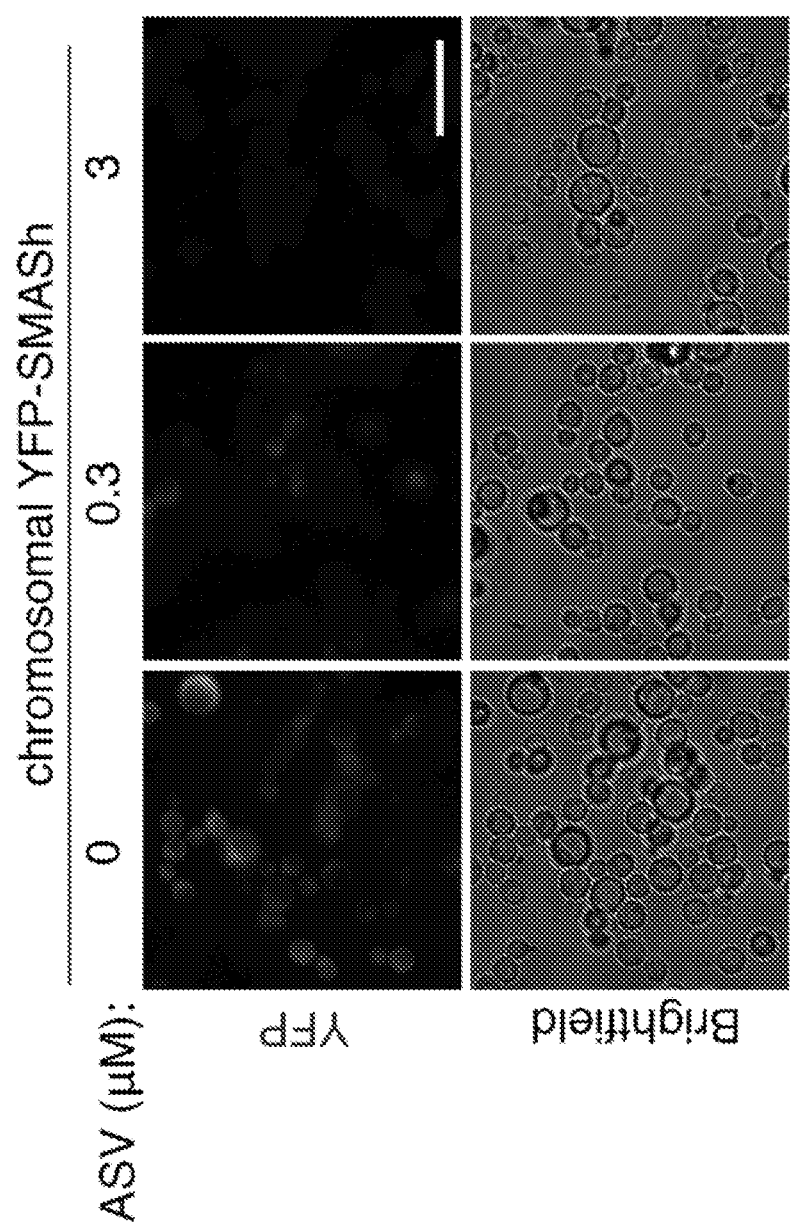
Figure 6C:
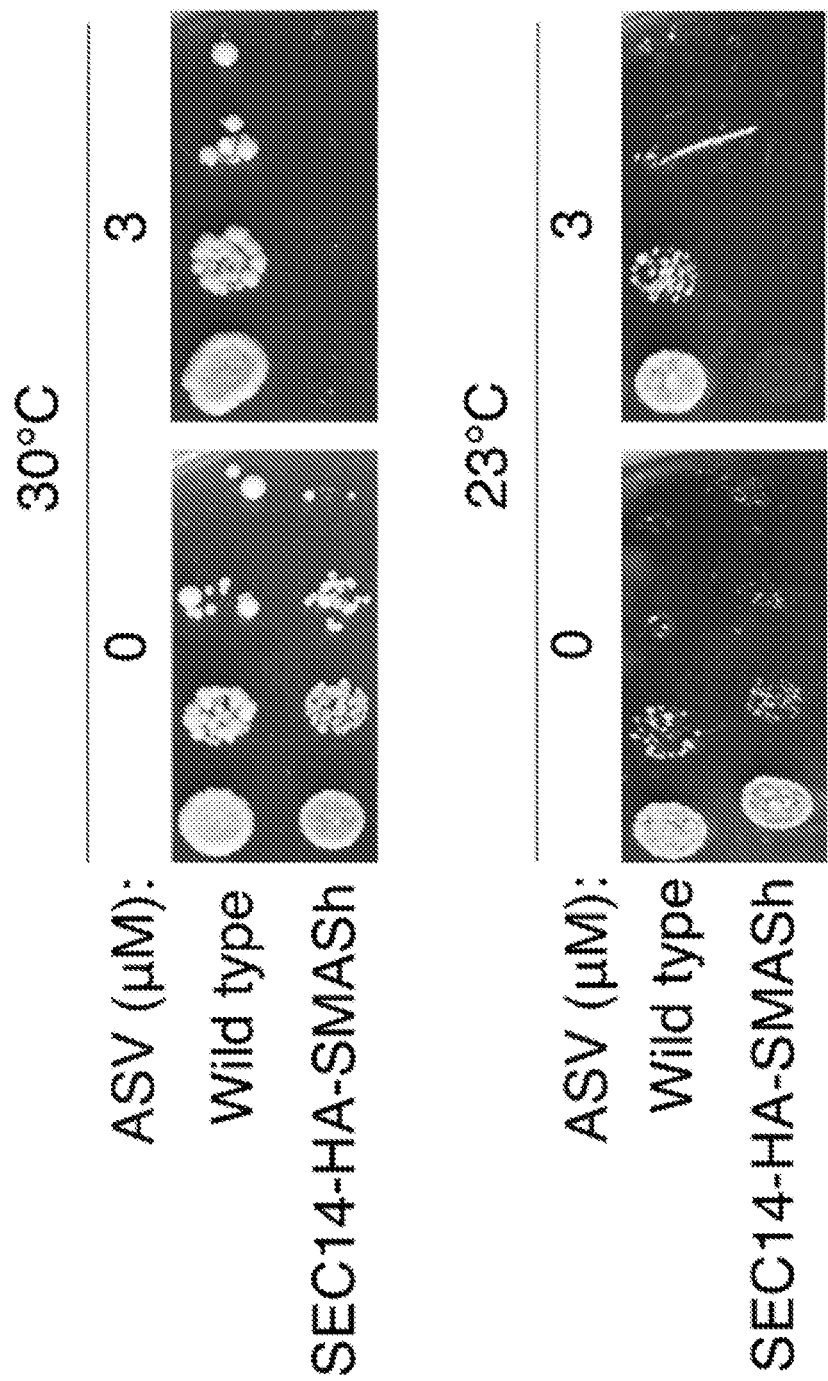
Figure 6D:
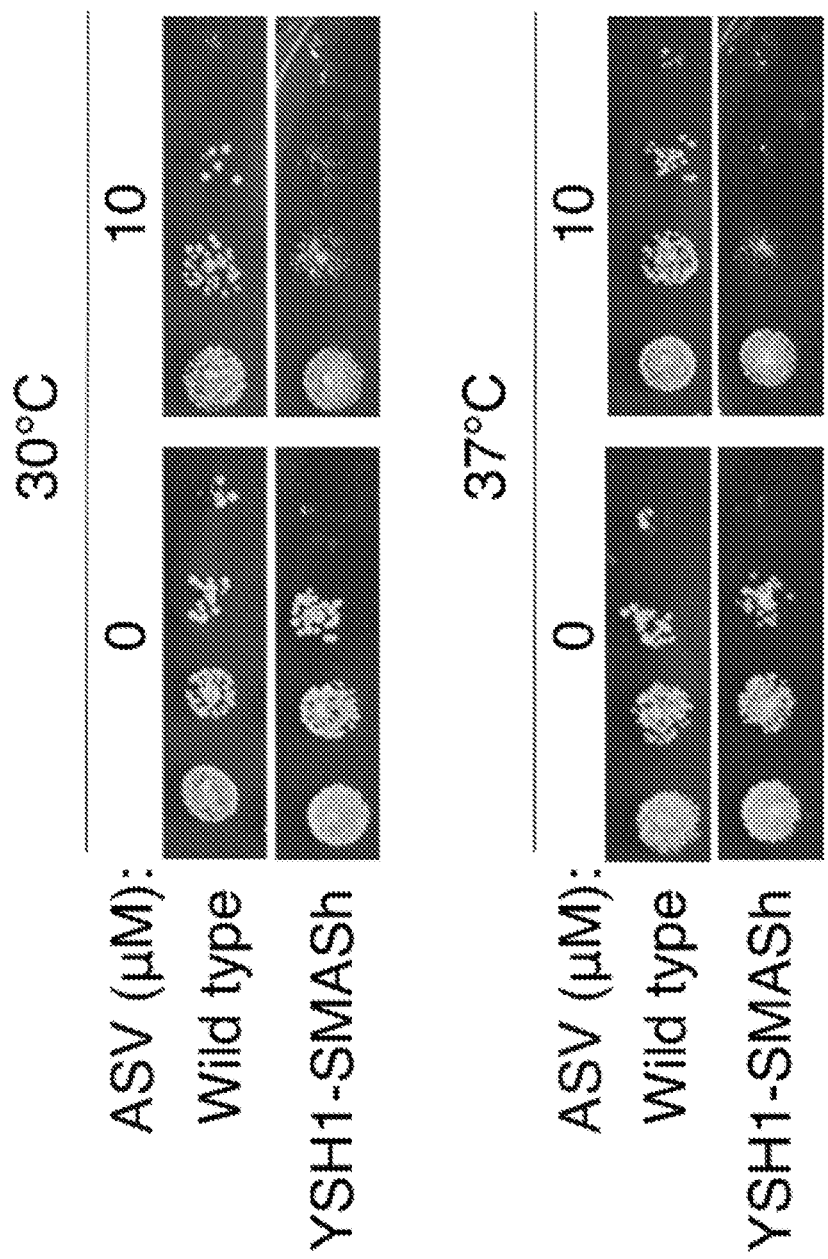

We next determined whether SMASh can regulate the production of proteins encoded by single-copy chromosomal genes in yeast. First, we expressed YFP-SMASh from an integrated chromosomal location and again observed robust suppression of protein levels by a drug (FIGS. 6A and 6B). Next, we integrated the SMASh tag at the ends of endogenous genes encoding essential proteins, such as SEC14 (a phosphatidylinositol/phosphatidylcholine transfer protein) and YSH1 (an endoribonuclease). In the absence of asunaprevir, SEC14-SMASh yeast grew similarly to wild-type yeast, whereas in the presence of asunaprevir, SEC14-SMASh yeast showed complete growth inhibition (FIG. 6C). YSH1-SMASh yeast strain growth was normal in the absence of drug and suppressed in the presence of drug (FIG. 6D). As was the case with mammalian CYP21A2, the ability of SMASh to control the expression in yeast of YSH1, a short-lived protein with a half-life of 34-45 minutes (Belle et al. (2006) Proc Natl Acad Sci USA 103:13004-13009), implies that degradation of SMASh-fused proteins can be very fast.

SMASh Enables Pharmacological Control Over an RNA Virus

Many RNA viruses propagate and induce cell death more efficiently in tumors than in normal cells (Miest et al. (2014) Nat Rev Microbiol 12:23-34; Russell et al. (2012) Nat Biotechnol 30:658-670). These viruses, which include measles virus (MeV), Newcastle disease virus, and stomatitis vesicular virus, are under active clinical investigation as oncolytic agents (Miest et al., supra; Russell et al., supra). While currently tested agents cause either no disease or mild self-limited disease, safety considerations will become a concern if they are engineered for enhanced cytotoxicity or immune evasion, as has been proposed (Miest et al., supra; Russell et al., supra; Msaouel et al. (2013) Expert Opin Biol Ther 13:483-502), or if they are used in immunocompromised patients. It is thus important for the future development of oncolytic RNA viruses to develop drug-responsive off-switches for safety. However, there are no clinically available inhibitors of these viruses to utilize in case of undesirable toxicities. Furthermore, regulation through drug-dependent transcription, a strategy used for DNA viruses such as adenovirus or herpesvirus, is not possible with pure RNA viruses, as their life cycles bypass host-mediated DNA replication and transcription. As SMASh regulates protein production without involving DNA or RNA modulation, we explored the possibility that it could be used as an off-switch to enhance the safety of RNA virus-based therapies.

Figure 7A:
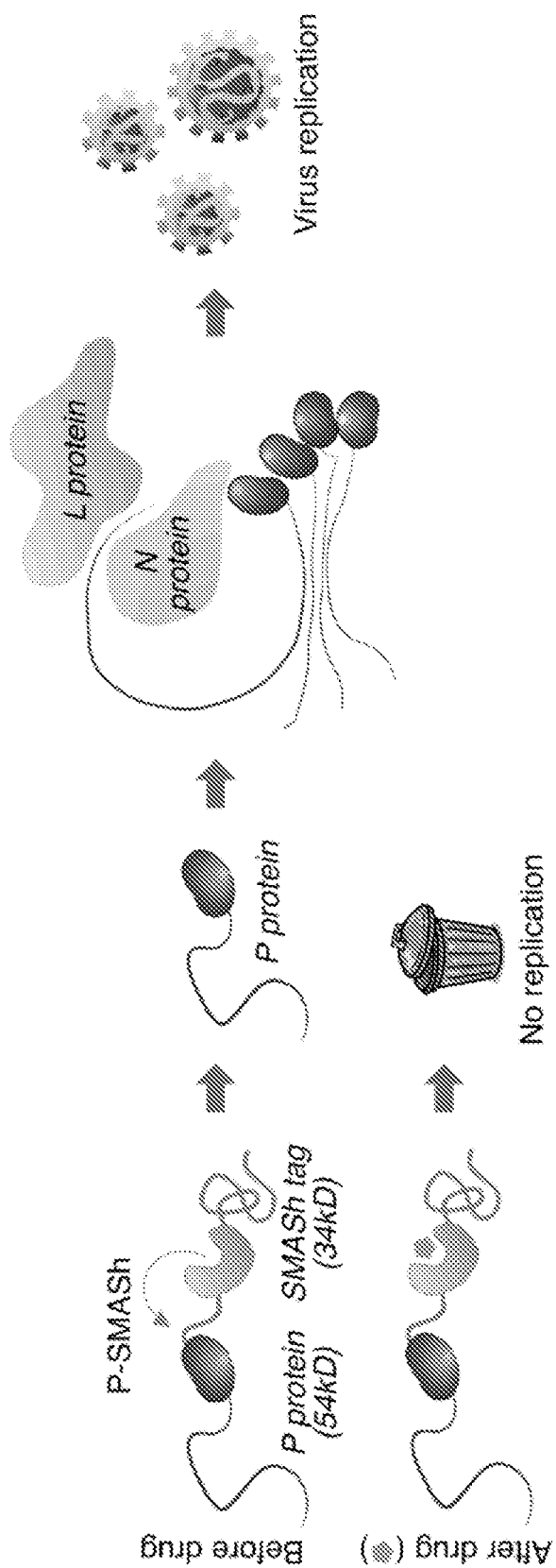
FIGS. 7A-7E show generation of a drug-controllable "SMAShable" measles vaccine virus.
Figure 13A:
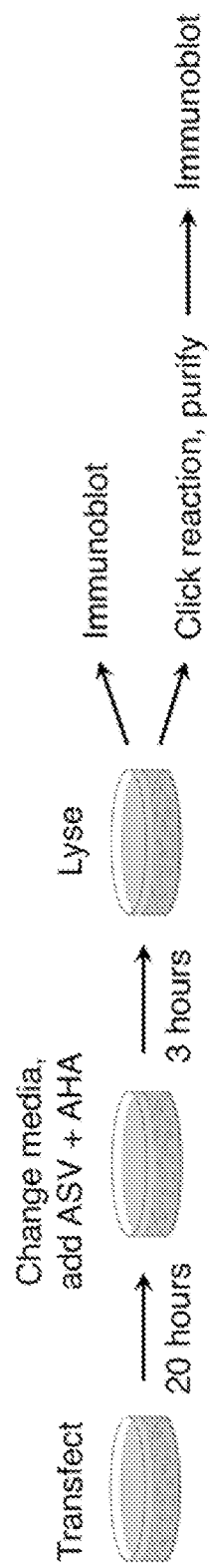
FIGS. 13A and 13B show kinetics of drug-induced shutoff of protein synthesis.
Figure 13B:
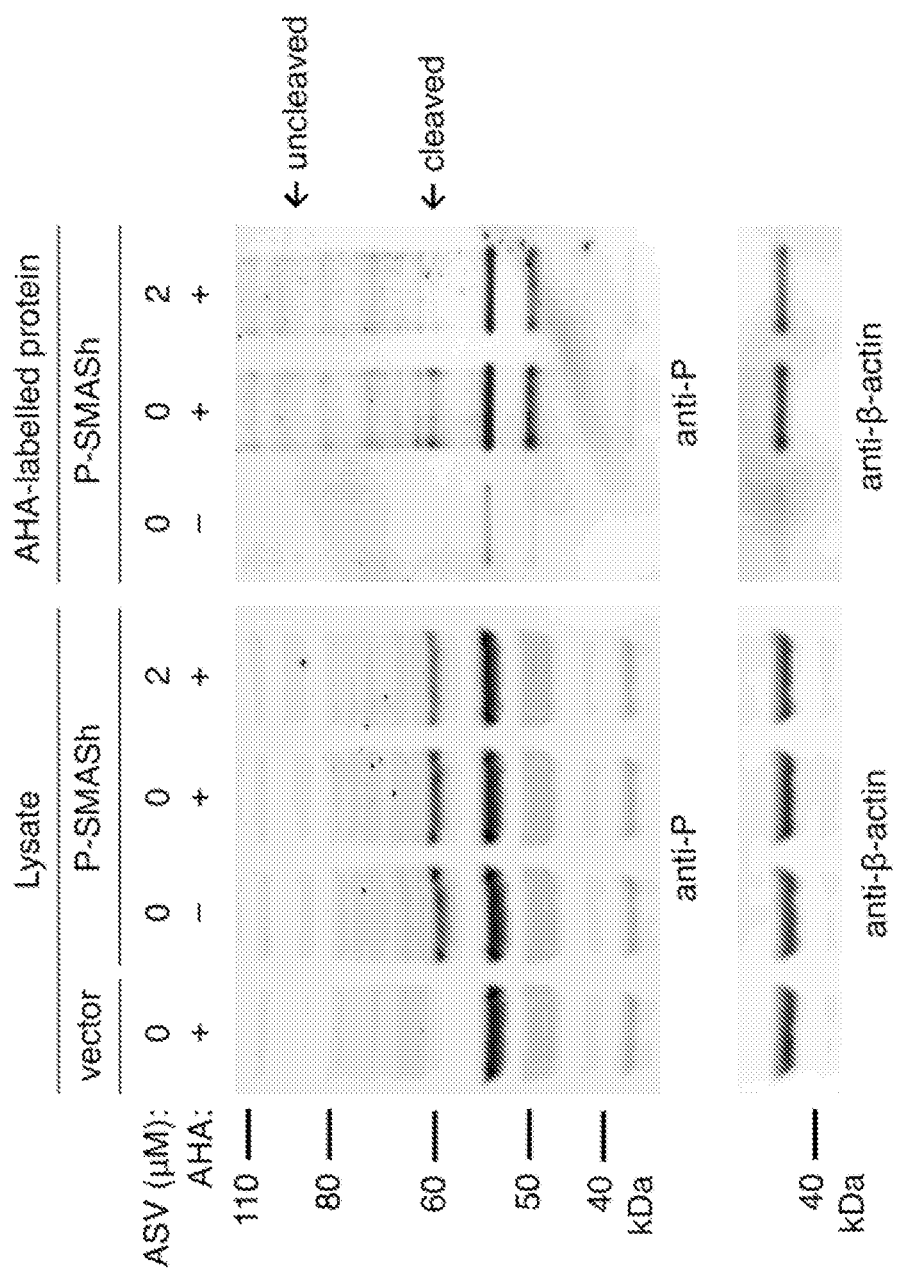
Figure 14A:
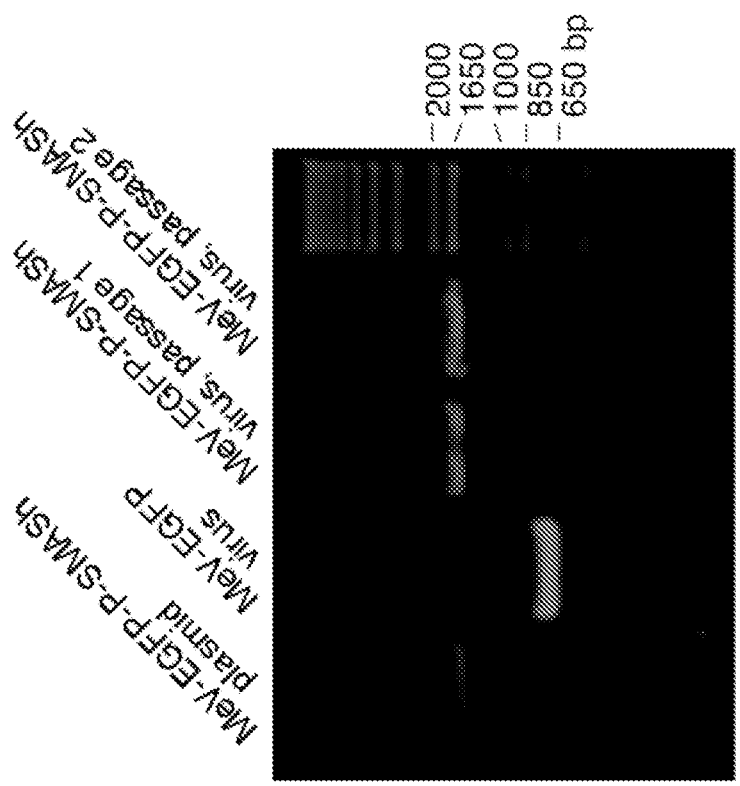
Figure 14A:
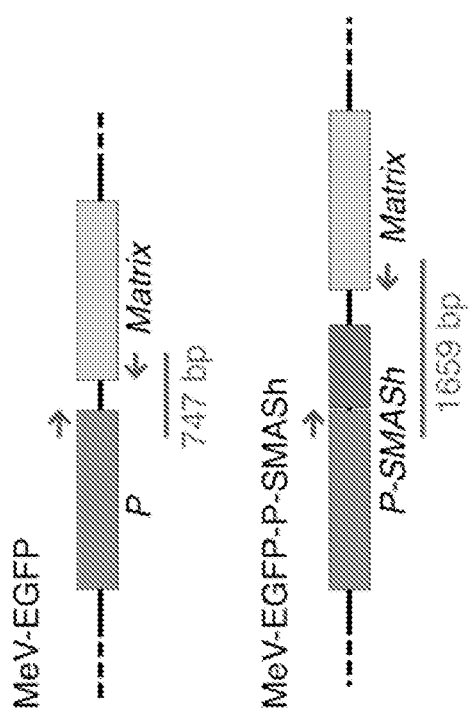

Among oncolytic RNA viruses, measles virus vaccine strain (MeV) is one of the most advanced in clinical testing (Msaouel et al., supra), so we chose to create a SMASh-controlled MeV as a model for engineering drug control into viral therapies. MeV phosphoprotein (P) functions to bring the viral large (L) protein, a RNA-dependent RNA polymerase, to the nucleoprotein (N)-encapsidated viral genome (FIG. 7A, top). We therefore hypothesized that replacing the P gene in the MeV genome with P-SMASh would enable inhibition of MeV replication by HCV NS3 protease inhibitor (FIG. 7A, bottom). To be a suitable off-switch for an RNA virus, drug control of P expression should ideally be rapid. To investigate the dynamics of P protein shutoff with SMASh, we attached the SMASh tag to the C-terminus of P. The infectivity factor C protein is translated from an overlapping open reading frame beginning 19 nucleotides downstream from the P start codon (Rima et al. (2009) Curr Top Microbiol Immunol 329:77-102), and this seemed less likely to be affected by a C-terminal fusion. We then assessed the effect of HCV protease inhibitor on P protein production in cells transiently transfected with a plasmid encoding P-SMASh. After allowing P-SMASh expression for 20 hours, application of asunaprevir for 3 hours (FIG. 13A) caused a noticeable drop in accumulated P protein levels relative to control, indicating that P protein itself is relatively short-lived (FIG. 13B, lanes 3-4). We also measured the tightness of shutoff by specifically labeling protein synthesized after inhibitor addition with the methionine analog azidohomoalanine (AHA), followed by reaction with a biotin-conjugated alkyne and purification on streptavidin-conjugated beads. Immunoblotting revealed no AHA-labeled P or P-SMASh from cells incubated with AHA and asunaprevir simultaneously (FIG. 13B, lane 7), indicating that inhibitor induced the rapid degradation of newly synthesized copies of P to undetectable levels. AHA labeling and purification did detect P in the absence of protease inhibitor (FIG. 13B, lane 6), confirming the efficacy of the labeling and purification steps. These data demonstrate that further production of SMASh-tagged P protein can be robustly shut off by protease inhibitor.

Figure 7B:
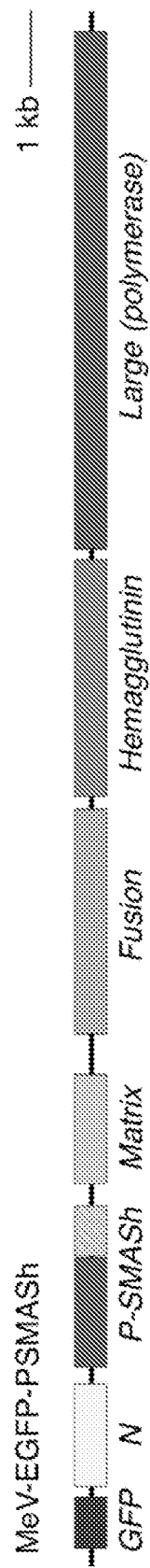
Figure 7C:
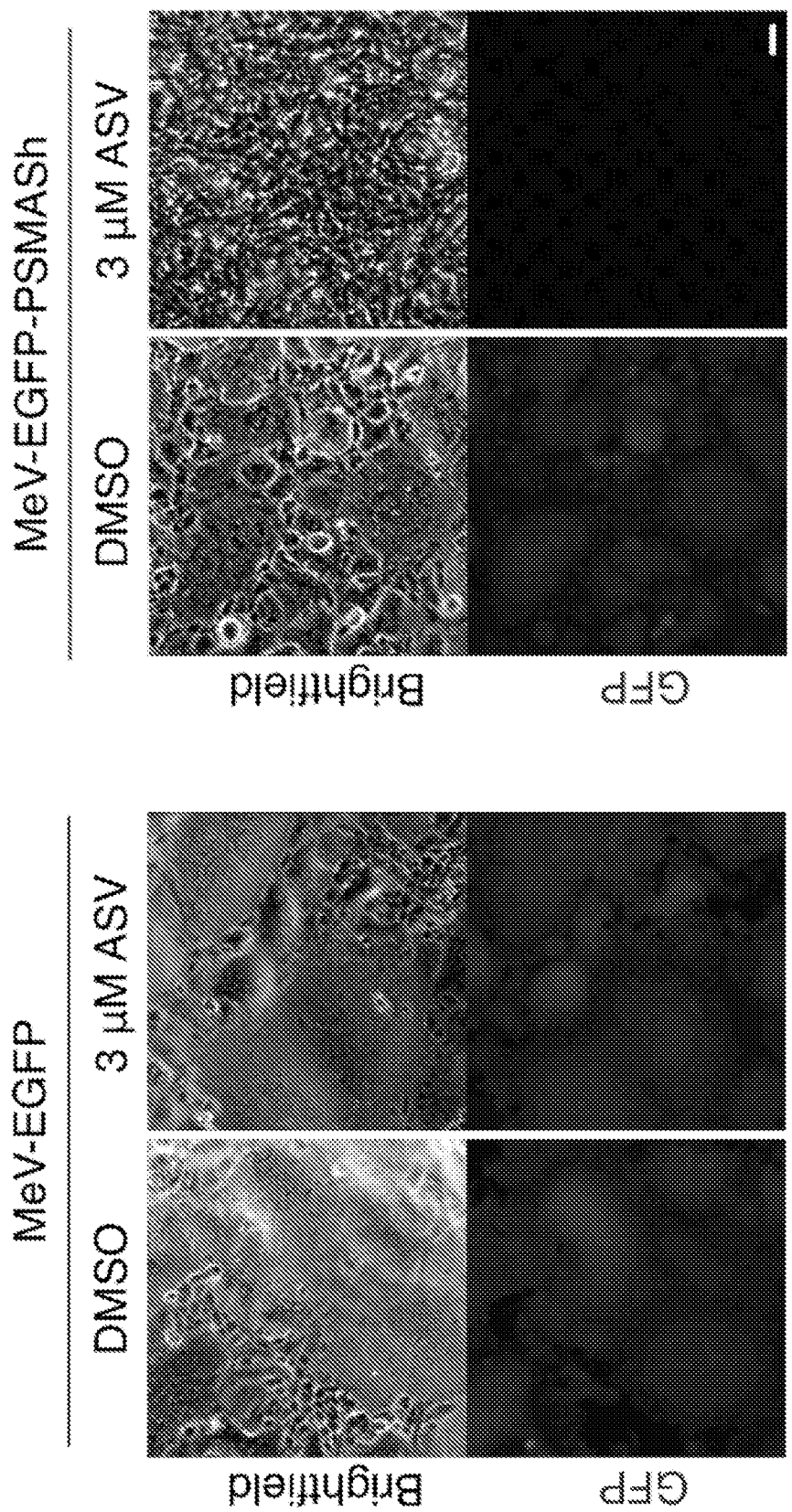
Figure 7D:
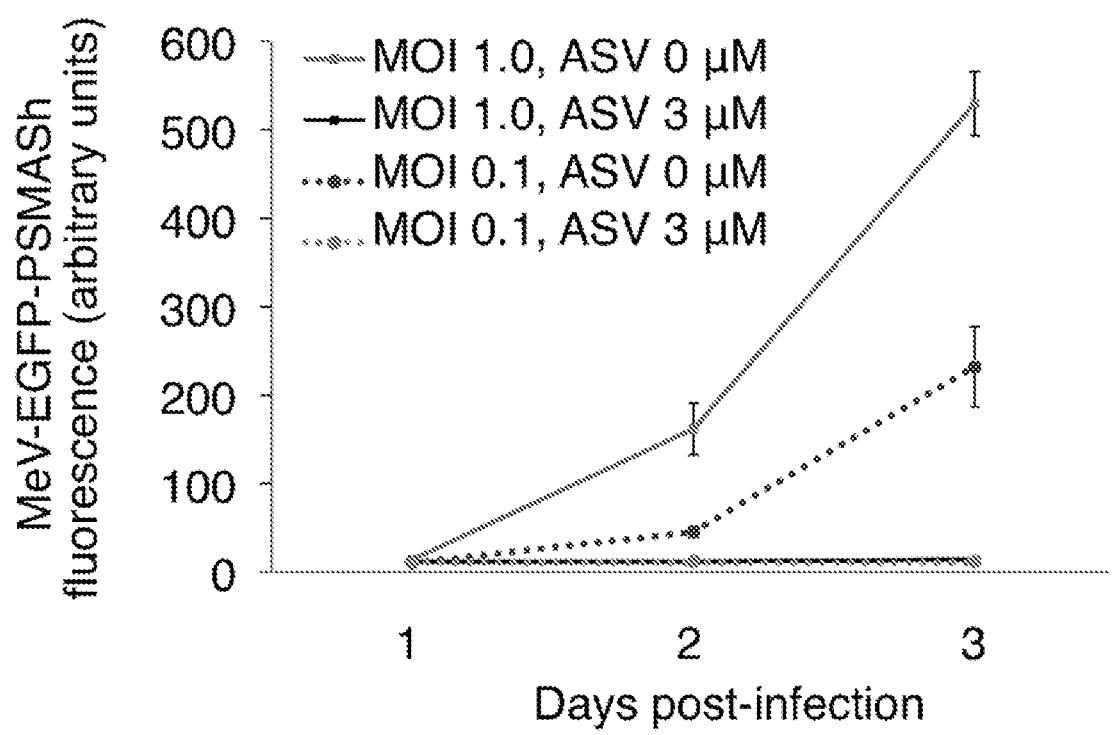
Figure 7E:
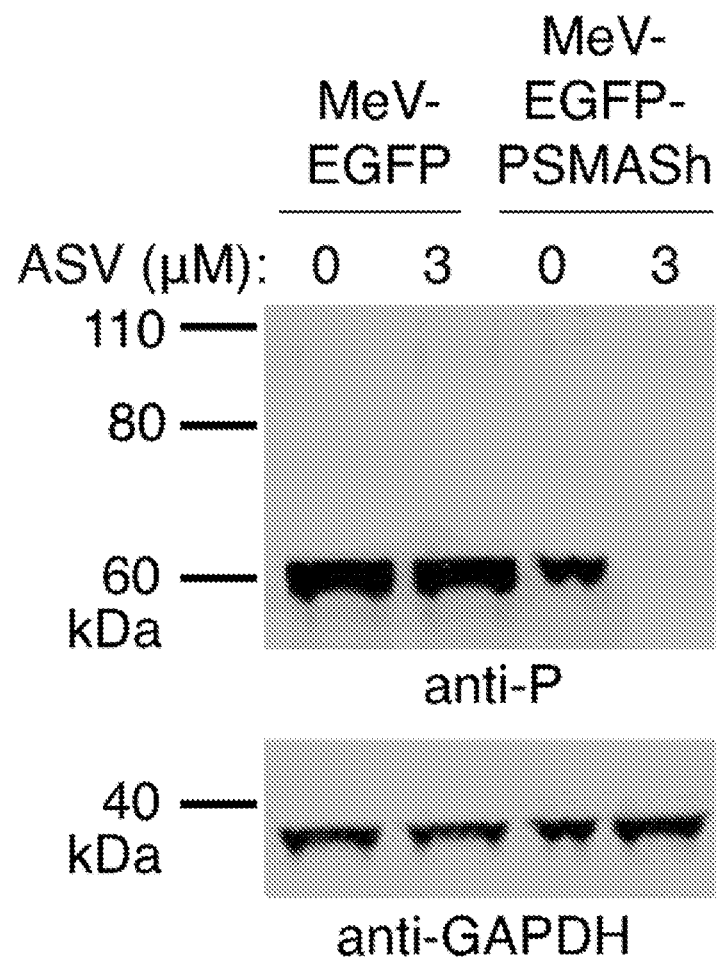

Finally, to make MeV drug-controllable, we replaced the P coding region with P-SMASh in MeV-EGFP, which contains an additional transcriptional unit expressing enhanced green fluorescent protein (EGFP) (Zuniga et al. (2007) Vaccine 25:2974-2983), creating MeV-EGFP-P-SMASh (FIG. 7B, FIG. 13A). In the absence of asunaprevir, MeV-EGFP-P-SMASh replicated to a similar titer as parental MeV-EGFP in the standard Vero host cell line (MeV-EGFP-P-SMASh $1.5 \times 10^7$ TCID50/ml vs. MeV-EGFP $3.8 \times 10^7$ TCID50/ml, measured by end-point dilution), indicating functionality of liberated P in viral replication. MeV-EGFP-P-SMASh also expressed EGFP and induced formation of syncytia in Vero cells as efficiently as parental MeV-EGFP in the absence of drug (FIG. 7C). In contrast, in the presence of asunaprevir, EGFP expression and formation of syncytia by MeV-EGFP-P-SMASh was completely abolished, while parental MeV-EGFP virus was unaffected by drug (FIG. 7C). Suppression was remarkably tight, with drug suppressing 97.3% of EGFP fluorescence compared to the untreated case 3 days post-transfection (FIG. 7D, FIG. 13B). Immunoblotting confirmed that asunaprevir efficiently inhibited P production in virus-infected cells (FIG. 7E). Thus, in summary, SMASh allowed us to render MeV exquisitely sensitive to inhibition by HCV NS3 protease inhibitors. Through the simple insertion of a SMASh tag in one viral gene, we were able to create a drug-regulatable version of this RNA virus for which no specific clinically approved inhibitors previously existed.

Discussion

The ability to reversibly regulate protein production using small molecules would be a valuable tool for biologists. Here we present a new concept, SMASh, for regulating protein production using a cell-permeable drug with rapid onset. Our system is based on genetic fusion of a protein of interest to a degron that is capable of self-removal via cis-cleavage by an internal HCV NS3 protease, so that the protein of interest is expressed by default in a minimally modified state. After addition of one of several clinically available small-molecule NS3 protease inhibitors, the degron is retained on subsequently synthesized proteins, leading to their rapid degradation and effectively shutting off further protein production. We have shown that the SMASh tag functions on either terminus of a protein and generalizes to various proteins and multiple cell types. Moreover, our data raise the interesting possibility that the SMASh degron is capable of eliciting degradation through both major proteolysis pathways of the cell (proteasome and autophagy), which could help to avert saturation of either pathway, contributing to its generalizability for various cell types and contexts. SMASh is unique in combining multiple desirable features, including rapid onset, reversible and robust drug regulation of protein expression, a requirement for only a single genetic element, minimal modification to proteins of interest, and the use of a non-toxic drug that is clinically approved for use in humans.

Several approaches previously existed to control specific protein levels via drug-dependent degradation or stabilization, but these either require multiple components or substantially change the structure of the target protein (Table 1). For example, drug-induced ubiquitin fragment complementation can be used to remove degradation signals (degrons) on proteins of interest (Pratt et al. (2007) Proc Natl Acad Sci USA 104:11209-11214), but this method requires the expression of multiple transgenes and shows poor dynamic range, requiring an additional level of transcriptional repression for tight shutoff (Lin et al. (2014) Chembiochem 15:805-809). The AID system allows drug-induced destabilization of a protein of interest, but requires addition of a large tag to the protein of interest and expression of a second protein (Morawska et al., supra). Single domains that are unstable in the absence or presence of a drug can be attached to proteins of interest to allow chemical control of protein stability, and this approach is similar to SMASh in requiring only a single genetic tag (Banaszynski et al. (2006) Cell 126:995-1004; Cho et al. (2013) PLoS One 8:e72393; Iwamoto et al. (2010) Chem Biol 17:981-988; Rakhit et al. (2011) Bioorg Med Chem Lett 21:4965-4968; Stankunas et al. (2003) Mol Cell 12:1615-1624; Bonger et al. (2011) Nat Chem Biol 7:531-537; Tae et al. (2012) Chembiochem 13:538-541). However, the AID system and these latter methods all require the permanent fusion of a lengthy polypeptide to the protein of interest, and the possibility of a large attachment interfering with protein function is always a concern. Therefore, a simple method for reversible drug control of protein production with rapid onset that allows proteins to be expressed with minimal perturbation has long been desired (Lampson et al. (2006) Cell 126:827-829).

SMASh provides robust drug control of protein expression with only minimal modification to the protein of interest, appending only six amino acids of a protease recognition site when the SMASh tag is fused at the C-terminus, or three amino acids when fused at the N-terminus. Just as fusion to small peptides preserves function in some cases where GFP does not (Andresen et al. (2004) Mol Biol Cell 15:5616-5622), SMASh should be less likely to perturb the function of proteins than methods requiring permanent attachment of structured protein domains. The MeV P protein serves as an example of the minimally disruptive nature of the SMASh tag. Consistent with both termini of P protein being required for interaction with N protein (Chen, et al. (2003) Virus Res 98:123-129; Harty et al. (1995) J Gen Virol 76:2863-2867; Shu et al. (2012) J Biol Chem 287: 11951-11967), the P-GFP fusion is completely nonfunctional, and the GFP-P fusion severely hinders MeV replication (Devaux et al. (2004) J Virol 78:11632-11640). Hence, one would not expect a constitutively attached drug-controllable degron system to be compatible with P function. By contrast, MeV expressing P-SMASh replicated similarly to parental virus, indicating the liberated P protein is functional. Minimal protein modification may also be useful in yeast, as attachment of long protein sequences may adversely affect a large percent of yeast proteins. For instance, among 2086 yeast proteins whose localization was studied by fusion to a 237-residue green fluorescent protein (GFP) tag or a 93-residue tag containing multiple hemagglutinin (HA) tags, a large proportion of proteins, 32%, showed different localizations with the two tags, suggesting that at least one of the tags caused protein mislocalization (Huh et al. (2003) Nature 425:686-691).

SMASh could also be useful where rapid increases in protein levels are desired. Using SMASh, the experimenter can repress expression of a protein of interest by treatment with drug, then when protein expression is desired, the drug can be washed out. Protein will then immediately accumulate from ongoing translation of existing mRNAs. Upregulating proteins by reversal of SMASh shutoff is expected to be faster than by induction of gene transcription. The time course of protein accumulation following pharmacological regulation of gene transcription is many hours in mammalian systems even in systems optimized for speed (Shoulders et al. (2013) J Am Chem Soc 135:8129-8132).

A notable feature of SMASh is that it allows regulation of protein production by HCV protease inhibitors, a class of drugs with high bioavailability and safety which have been approved for long-term use in humans. SMASh-tagged proteins are regulated by these drugs at the same low concentrations used for inhibiting HCV replication (e.g. 1 nM for asunaprevir). SMASh would thus be expected to be especially advantageous for in vivo use in mammals, where most other methods of drug-regulated protein expression use experimental chemical compounds that can be limited by poor bioavailability, toxicity, or expense (Tae et al. (2012) Chembiochem 13:538-541; Limenitakis et al. (2011) FEBS Lett 585:1579-1588). Our experiments also indicate that the HCV protease inhibitor asunaprevir is able to cross the yeast cell wall. Even when overexpressed from episomes using the strong GPD promoter, expression of SMASh-tagged YFP was completely suppressed in 3 µM asunaprevir. In contrast, 1000 µM auxin was required for AID to degrade a target protein expressed from the approximately tenfold weaker ADH promoter (Morawska et al., supra; Mumberg et al. (1995) Gene 156:119-122).

Finally, SMASh differs from most other strategies for regulating protein stability in that it selectively controls the degradation of new copies of a protein of interest, and not pre-existing copies. Cells respond rapidly to environmental stimuli such as growth signals (Shimobayashi et al. (2014) Nat Rev Mol Cell Biol 15:155-162) or, in the nervous system, synaptic activity (Butko et al., supra), by synthesizing new proteins. SMASh can be used to query the role of specific new protein species in such biological responses, similarly to how cycloheximide or anisomycin is used to suggest a role for synthesis of new proteins in general, but without the toxicity of these broadly acting protein synthesis inhibitors. SMASh can also be used to estimate half-lives of proteins of interest, as the persistence of untagged protein copies previously produced in the absence of drug can be measured over time while further production is inhibited in the presence of drug. Here, SMASh can again be used similarly to cycloheximide or anisomycin in estimating protein half-lives (Zhou et al. (2004) Methods Mol Biol 284:67-77), but with much less toxicity. Cycloheximide and anisomycin, by inhibiting all protein synthesis in the cell, can be expected to impair cell health after several hours of treatment, and to generate erroneous half-life calculations if levels of other proteins regulating the stability of the protein of interest also drop. The SMASh system may thus be especially advantageous for measuring half-lives of long-lived proteins such as PSD95 (FIG. 10A).

RNA viruses that replicate more efficiently in certain neoplastic cell types have long been considered as targeted cancer treatments. However, only viruses that cause non-pathogenic or mild disease, such as vaccine-strain MeV, are currently being tested in clinical trials. As the self-limiting nature of these weak viruses is likely to limit their oncolytic efficacy as well, researchers have proposed arming viruses for enhanced cytotoxicity or modifying them for improved immune evasion (Cattaneo et al. (2008) Nat Rev Microbiol 6:529-540; Meng et al. (2010) Mol Ther 18:544-551). But because such steps could lead to unexpected side effects (Chen et al. (2011) Virology 409:328-337), it would be desirable to have pharmacological methods for terminating replication of engineered viruses (Russell et al. (2012) Nat Biotechnol 30:658-670). We found that SMASh enabled robust control by HCV NS3 protease inhibitors over MeV, a RNA virus in clinical trials as a replication-competent oncolytic agent but for which no clinically available specific inhibitors exist. Our results suggest the feasibility of controlling related oncolytic single-strand enveloped RNA viruses by tagging P protein orthologs (Fuentes et al. (2010) Future Microbiol 5:9-13), and open up the possibility of controlling other classes of viruses by tagging other viral proteins.

In summary, SMASh has advantages over other methods for controlling levels of proteins of interest in minimizing modification to the protein, in requiring only one genetically encoded element, and in using a clinically available class of drugs that are nontoxic and cell permeable. The combination of these advantages has not been achieved by other post-translational protein control methods so far. Furthermore, SMASh functions robustly in mitotic and non-mitotic mammalian cells, and also in yeast. Using SMASh, we have also engineered, for the first time, an RNA virus that can be tightly regulated by a drug without the need to develop new, virus-specific small molecule inhibitors. Thus, with its ease of implementation and generalizability, the SMASh technique can be applied to a variety of problems in biomedicine and biotechnology, ranging from the study of gene function to the engineering of drug-dependent features in cellular and viral therapies.

Methods

DNA Constructs. Plasmids encoding PSD95 or Arc fused to TimeSTAMP cassettes (Yuan et al., supra; Iizuka et al., supra) were modified by standard molecular biology techniques including PCR, restriction enzyme digestion and ligation or In-Fusion enzyme (Clontech) to create new TimeSTAMP variants or SMASh variants. All subcloned fragments were sequenced in their entirety to confirm successful construction. Full sequences of all plasmids used in this study are available upon request.

Cell Culture and Transfection. HEK293, Vero, and HeLa cell lines were cultured at 37° C. in 5% $CO_2$ in Dulbecco's Modified Eagle's Medium (DMEM, HyClone) supplemented with 10% fetal bovine serum (Gibco), 2 mM glutamine (Life Technologies) and 100 U/mL penicillin and 100 µg/mL streptomycin (Life Technologies). Cells were transfected using Lipofectamine 2000 (Life Technologies) in Opti-MEM (Life Technologies) according to the manufacturer's recommended protocol.

Chemical Reagents. HCV NS3 inhibitors ciluprevir (CLV) and asunaprevir (ASV) were obtained by custom synthesis (Acme Bioscience) and dissolved in DMSO (Thermo) at 3 mM for medium-term storage at −20° C. These were then diluted into media to achieve the desired final concentration (1-3 µM) for treatment of cells. Further serial dilutions were performed for the dose-dependency experiment. For long-term CLV and ASV incubations, drug was applied simultaneously with transfection media or 1-2 hours after transfection. MG132 (Sigma) was dissolved in DMSO for a 1000× working stock of 10 mM. Bortezomib (Adooq Biosci.) was dissolved in DMSO for a 500× working stock of 33 µM. Chloroquine diphosphate salt (Sigma) was dissolved in $H_2O$ for a 1000× (100 mM) working stock. Bafilomycin A1 (Santa Cruz) was dissolved in DMSO for a 500× (100 µM) working stock. Azidohomoalanine (AHA) (Click-IT, Invitrogen) was dissolved in DMSO for a 500× working stock of 25 mM. Alkyne-PEG4-biotin (Invitrogen) was dissolved in DMSO for a 100× working stock of 4 mM. L-cystine dihydrochloride (Sigma) was dissolved in $H_2O$ pH 2.0 for a working stock of 0.1 M.

Yeast Strains and Cell Growth. All experiments were carried out in the w303-1A ADE2+ strain background (Thomas et al. (1989) Cell 56:619-630) and a pump-deficient w303-1A strain (MATa canl-100, his3-11,15, leu2-3, 112, trp1-1, ura3-1, ade2-1, pdrl::kanMX, pdr3::kanMX) (Su et al. (2010) Dis Model Mech 3:194-208). SMASh strains were made by transformation of yeast episomal plasmid (pAG426) and yeast integrating plasmid (pRS405), expressing SMASh fused YFP under GPD promoter Yeastmaker DNA kit (Clontech) was used for yeast Li-Acetate transformations. Cells were grown at 30° C. in SD media or YDP media. To generate SMASh knock-in yeast, PCR fragments containing SMASh tag followed by yeast ADH1 terminator and NatMX (clonNAT resistance gene) are inserted before the termination codon of the protein of interest by homologous recombination. To perform yeast spotting assay, YDP plates were prepared with ASV or the same concentration of DMSO (1% v/v).

Primary Neuronal Culture. All animal procedures were approved by the Stanford University Administrative Panel on Laboratory Animal Care, and were performed in accordance with the applicable regulatory standards. Sprague-Dawley rat E15 cortico-hippocampal tissue and FVB mouse E18 cortical tissue were dissected, incubated in RPMI (Life Technologies) with papain (Worthington) and DNase I (Roche) for dissociation, triturated, and electroporated using the Amaxa Rat or Mouse Neuron Nucleofector kit (Lonza), before being plated on poly-L-lysine-coated 4-chamber 35 mm glass bottom dishes (In Vitro Scientific), in the presence of 5-10% FBS (Gibco), at a density of ~150K neurons per quadrant. Neurons were cultured in NeuroBasal media (Life Technologies) supplemented with GlutaMAX, B-27, and Pen-strep (Life Technologies) at 37° C. with 5% $CO_2$. Every 3 days, 50% of media was refreshed.

Virus Cloning, Packaging and Infection. To construct p(+)-MeV-EGFP-PSMASh, DNA encoding the SMASh tag was added in frame to the P open reading frame in p(+)-MeV-EGFP, the resulting full-length clone corrected for the paramyxovirus rule-of-six, and verified through sequencing. Recombinant MeV were recovered using a modified rescue system (Brindley et al. (2013) J Virol 87:11693-11703). BSR-T7/5 cells (Buchholz et al. (1999) J Virol 73:251-259) were transfected with p(+)-MeV-EGFP or p(+)-MeV-EGFP-PSMASh (SEQ ID NO:9), respectively, and plasmids encoding the L, N, or P proteins derived from the MeV IC-B strain (Krumm et al. (2013) J Biol Chem 288:29943-29953). All constructs were under the control of the T7 promoter. 48 hours post-transfection, BSR-T7/5 helper cells were overlaid on Vero cells stably expressing human CD150 and SLAM (Ono et al. (2001) J Virol 75:4399-4401), and overlay plates incubated at 32° C. until infectious centers became detectable. Virions from individual centers were transferred to fresh Vero-SLAM cells for generation of passage two virus stocks. To confirm integrity of recombinant viruses, RNA was extracted from infected cells using the RNeasy mini kit (Qiagen) and cDNAs created using random hexamer primers and Superscript III reverse transcriptase (Life Technologies). PCR was performed with primers 28-F: TAATCTCCAAGCTAGAATC (SEQ ID NO:10) and 35-R: AGCCTGCCATCACTGTA (SEQ ID NO:11) and sequenced (FIG. 9A). To prepare virus stocks, Vero cells were infected at an MOI of 0.01 TCID50/cell with the relevant virus and incubated at 32° C. until cytopathic effect (CPE) become detectable. Plates were then moved to 37° C. and incubated until 100% CPE. Cells were scraped in OptiMEM (Life Technologies), and particles released by two freeze-thaw cycles. Titers were determined by TCID50 titration on Vero cells according to the Spearman-Karber method as described[61]. Virus infection for drug controllability tests was initiated through inoculation of Vero cells at an MOI of 0.1 and 1 TCID50/cell at 32° C.

Microscopy. For imaging of MeV-infected cells, brightfield and fluorescence microscopy was performed on a Nikon TE300 with a 10×/0.25-numerical aperture (NA) objective. HEK293A cells were imaged with a 20×/0.15 NA objective on the same microscope. The cells were cultured in 12-well plates (Greiner), MeV-infected cells were imaged in culture media (10% FBS supplemented phenol red free DMEM) and HEK293 were imaged in HBSS. Brightfield and fluorescence microscopy of yeast was done with an Olympus 100×/1.4-NA oil immersion objective on Olympus IX80. Yeast cells were imaged in SD media in a ConA (Sigma) coated TC CU109 chamber (Chamlide). For HeLa and neurons, microscopy was performed on a Zeiss Axiovert 200M with a 40×/1.2-NA water immersion objective. These cells were cultured in 4-chamber 35 mm glass bottom dishes (In Vitro Scientific) and culture media were replaced with HBSS during live imaging sessions. All microscopes were connected to Hamamatsu ORCA-ER cameras and controlled by Micro-Manager software. Image processing was performed in ImageJ.

Immunoblotting. After washing twice with PBS, cells were lysed with 50-100 μl of hot SDS lysis buffer (100 mM Tris HCl pH 8.0, 4% SDS, 20% glycerol, 0.2% bromophenol blue, 10% 2-mercaptoethanol) and DNA was sheared by sonication. After heating to 80-90° C. for several minutes, cell lysates were loaded onto 4%-12% Bis-Tris gels (NuPAGE, Life Technologies) along with Novex Sharp prestained protein standard (Life Technologies) or Precision Plus Protein Dual Color Standards (Bio-Rad), dry-transferred to nitrocellulose or PVDF membranes (iBlot system, Life Technologies), probed with primary and secondary antibodies, and imaged using LI-COR Odyssey imaging system. Quantification of immunoblots was performed in ImageJ.

Antibodies. The following primary antibodies were used for immunoblotting at the indicated dilutions: mouse monoclonal anti-PSD95 (NeuroMab, clone K28/43), 1:2000; mouse monoclonal anti-Arc (Santa Cruz, clone C7, sc-17839), 1:200; mouse monoclonal anti-GFP (Pierce, clone GF28R, MA5-15256), 1:1000; rabbit monoclonal anti-GFP (Abcam, clone E385, ab32146), 1:1000; rabbit polyclonal anti-β-actin (GeneTex, GTX124214) 1:10,000; mouse monoclonal anti-GAPDH (Santa Cruz, clone G-9, sc-365062), 1:4000; rabbit polyclonal anti-GAPDH (Santa Cruz, sc-25778), 1:4000; mouse monoclonal anti-GAPDH (Pierce, clone GA1R, MA5-15738), 1:1000; mouse monoclonal anti-measles phosphoprotein (P) (Novus, clone 9H4, NB110-37247 or Abcam, clone 9H4, ab43820), 1:200; rabbit polyclonal anti-CamKIIα (Santa Cruz, sc-13082), 1:200; mouse monoclonal anti-GluRIIA (DSHB, 8B4D2), 1:1000; antiCYP21A2 (Santa Cruz, clone C-17, sc-48466), 1:200; and rabbit monoclonal anti-HA (Cell Signaling, C29F4), 1:1000. Secondary antibodies were LI-COR 680RD goat-anti-mouse, 680RD goat-anti-rabbit, 680RD donkey-anti-rabbit, 800CW donkey-anti-goat, 800CW goat-anti-mouse, and 800CW goat-anti-rabbit, used at 1:5000.

Metabolic Labeling, Click Chemistry, and Pulldown. HeLa cells were cultured in 12-well plates (Greiner) in standard DMEM supplemented with glutamine, pen-strep, and 10% FBS. 20 hours after transfection, wells were washed 3× with HBSS, and cells were methionine-depleted via 30 minutes incubation in metabolic label DMEM [methionine/cystine-free DMEM (Corning Cellgro) supplemented with glutamine, pen-strep, 0.2 mM L-cystine (Sigma), and 10% dialyzed FBS (Thermo)]. Following depletion step, media were replaced with either standard DMEM, metabolic label DMEM with 50 μM AHA, or metabolic label DMEM with 50 μM AHA and 2 μM ASV. Equivalent volumes of DMSO were used as vehicle controls in negative wells. Labeling incubation lasted 3 hours, after which each well was washed and lysed with 50 μL gentle lysis buffer [1% SDS, 50 mM Tris HCl pH 8.0, EDTA-free protease inhibitor cocktail (Complete Mini, Roche), phosphatase inhibitor cocktail (Halt, Pierce), 3 μM ASV]. For each condition, lysates from 3 separate wells were pooled. Lysates were sonicated and clarified by centrifugation. For pre-click/pulldown samples, 50 μL of each lysate was reserved and combined with 50 μL of hot SDS lysis buffer for SDS-PAGE analysis.

For click reactions, 50 μL of each lysate was processed using the Click-IT Protein Reaction Buffer kit (Invitrogen) with alkyne-PEG4-biotin (Invitrogen) according to manufacturer's recommendations. Following click labeling, methanol-chloroform extracted protein pellets were resuspended by vortexing in 20 μL of gentle lysis buffer+80 μL of nondenaturing buffer (1% Nonidet P40, 50 mM Tris HCl pH 8.0, EDTA-free protease inhibitor cocktail). Proteins were allowed to solubilize at 4° C. overnight. Biotin-labeled proteins were purified via a magnetic streptavidin bead (PureProteome, Millipore) pulldown. Prior to binding reactions, beads were blocked by incubating 1 hour with 5% BSA solution in PBS, on a rotator at room temp, and washing 3× in PBS-T (PBS plus 0.1% Tween-20). Beads were resuspended in PBS-T. Binding reactions (200 μL volume) proceeded for 1 hour on a rotator at room temp, after which beads were washed 3× with PBS-T. Proteins were eluted for SDS-PAGE by heating beads in 50 μL SDS lysis buffer at 95° C. for 10 minutes.

Calculating Half-Lives of SMASh-Tagged Proteins. To calculate production rates of PSD95 and PSD95-SMASh, we assumed that the protein production rate is constant between 24 and 28 hours post-transfection, and are the same for PSD95-SMASh protein expressed from a PSD95-SMASh gene with ASV and PSD95 protein expressed from a PSD95-SMASh gene without ASV. The rate of change in protein concentrations can be modeled with the differential equations:

$$d[PSD95](t)/dt = k_{syn,PSD} - k_{deg,PSD95}[PSD95](t) \quad (1)$$

$$d[PSD95SMASh](t)/dt = k_{syn,PSDSMASh} - k_{deg,PSD95SMASh}[PSD95SMASh](t) \quad (2)$$

where [PSD95](t) is protein concentration of PSD95 at time t, [PSD95SMASh](t) is protein concentration of PSD95-SMASh at time t, $k_{syn,PSD95}$ and $k_{syn,PSD95SMASh}$ are production rate constants of PSD95 and PSD95-SMASh, and $k_{deg,PSD95}$ and $k_{deg,PSD95SMASh}$ are decay rate constants of PSD95 and PSD95-SMASh. Integration of these equations yields:

$$[PSD95](t) = (k_{syn,PSD}/k_{deg,PSD95})(1 - e^{-k_{deg,PSD95}t}) \quad (3)$$

$$[PSD95SMASh](t) = (k_{syn,PSD95SMASh}/k_{deg,PSD95SMASh})(1 - e^{-k_{deg,PSD95SMASh}t}) \quad (4)$$

We measured PSD95 half-life ($t_{1/2,PSD95}$) by fitting the PSD95 band intensities of different time points to monoexponential decay curves (n=3), obtaining 12.4 hours. We then determined the decay rate constant of PSD95 ($k_{deg,PSD95}$=ln 2/$t_{1/2,PSD95}$=0.056/hour). We defined 1 relative intensity unit (RIU) as the mean band density on immunoblotting from net production of PSD95 in 4 hours. By immunoblotting lysates from cells incubated for 24 hours with ASV then for 4 hours without ASV, we obtained a protein amount of 1 RIU for

[PSD95](4 hours) (standard deviation 0.16, n=3). By immunoblotting in parallel lysates from cells incubated for 24 hours without ASV then for 4 hours with ASV, we obtained a protein amount of 0.419 RIU for [PSD95SMASh](4 hours) (standard deviation 0.07, n=3). With values for $k_{deg,PSD95}$ and for [PSD95](4 hours), we then used equation (3) to solve numerically for $k_{syn,PSD95}$, obtaining 0.280 RIU/hour. Assuming $k_{syn,PSD95SMASh}$ equals $k_{syn,PSD95}$, we could then use equation (4) to solve numerically for $k_{deg,PSD95SMASh}$, obtaining 0.607/hour. The PSD95SMASh half-life $t_{1/2,PSD95SMASh}$ was then calculated as 1.14 hours ($t_{1/2,PSD95SMASh}=\ln 2/k_{deg,PSD95SMASh}=1.14$ hours).

The half-life of CYP21A2-SMASh was calculated from the same equations, except CYP21A2 was substituted for PSD95. Values obtained were: $t_{1/2,CYP21A2}=2.2$ hours, $k_{deg,CYP21A2}=0.312$/hour, [CYP21A2](4 hours)=1 RIU (standard deviation 0.019, n=3), [CYP21A2SMASh](4 h)=0.163 RIU (standard deviation 0.025, n=3), $k_{syn,CYP21A2}=k_{syn,CYP21A2SMASh}=0.438$/hour, $k_{deg,CYP21A2SMASh}=2.688$/hour, $t_{1/2,CYP21A2SMASh}=0.258$ hours.

While the preferred embodiments of the invention have been illustrated and described, it will be appreciated that various changes can be made therein without departing from the spirit and scope of the invention.

TABLE 1

Comparison of methods for drug regulation of protein expression.

| | Drug-induced protein expression systems | | | | Drug-induced protein suppression systems | | | |
|---|---|---|---|---|---|---|---|---|
| | MaRaP | ddFKBP | ecDHFR | SURF | LID | AID | Halotag | SMASh |
| Drug | C20-MaRap | Shield-1 | trimethoprim | rapamycin | Shield-1 | auxin | hydrophobic chloroalkane | HCV protease inhibitor |
| Expressed form | fused to FRB*, bound to drug | fused to ddFKBP, bound to drug | fused to ecDHFR, bound to drug | minimally modified | fused to LID | fused to IAA17 | fused to Halotag | minimally modified |
| Suppressed form | fused to FRB* | fused to ddFKBP | fused to ecDHFR | fused to $Ub^C$-FRB-degron | fused to LID, bound to drug | fused to IAA17, bound to drug | fused to Halotag, bound to drug | fused to SMASh tag, bound to drug |
| Single-component | no | yes | yes | no | yes | no | yes | yes |
| Selective for new proteins | no | no | no | yes | no | no | no | yes |
| Reference | 38 | 34 | 36 | 32 | 39 | 21 | 40 | this work |

What is claimed is:

1. A fusion protein comprising:
   a) a polypeptide of interest;
   b) a degron comprising the amino acid sequence of SEQ ID NO: 1, wherein the degron is operably linked to the polypeptide of interest when the fusion protein is in an uncleaved state, such that the degron promotes degradation of the polypeptide of interest in a cell;
   c) a hepatitis C virus (HCV) nonstructural protein 3 (NS3) protease, wherein the protease can be inhibited by contacting said fusion protein with a protease inhibitor; and
   d) a cleavable linker that is located between the polypeptide of interest and the degron, wherein the cleavable linker comprises a cleavage site recognized by the protease, wherein cleavage of the cleavable linker by the protease releases the polypeptide of interest from the fusion protein, such that when the fusion protein is in a cleaved state, the degron no longer controls degradation of the polypeptide of interest.

2. The fusion protein of claim 1, wherein the degron is linked to the N-terminus or the C-terminus of the polypeptide of interest.

3. The fusion protein of claim 2 having the degron linked to the C-terminus of the polypeptide of interest, wherein the fusion protein comprises components arranged from N-terminus to C-terminus in the uncleaved state as follows:
   a) the polypeptide of interest;
   b) the cleavable linker;
   c) the protease; and
   d) the degron.

4. The fusion protein of claim 3 comprising a polypeptide comprising an amino acid sequence having at least 80% identity to the amino acid sequence of SEQ ID NO:7, wherein the degron is capable of promoting degradation of the polypeptide of interest and the protease is capable of cleaving the fusion protein at the cleavage site.

5. The fusion protein of claim 3 comprising a polypeptide comprising an amino acid sequence having at least 95% identity to the amino acid sequence of SEQ ID NO:7, wherein the degron is capable of promoting degradation of the polypeptide of interest and the protease is capable of cleaving the fusion protein at the cleavage site.

6. The fusion protein of claim 3 comprising a polypeptide comprising the amino acid sequence of SEQ ID NO:7.

7. The fusion protein of claim 2 wherein the degron is linked to the N-terminus of the polypeptide of interest, the fusion protein comprising components arranged from N-terminus to C-terminus in the uncleaved state as follows:
   a) the protease;
   b) the degron;
   c) the cleavable linker; and
   d) the polypeptide of interest.

8. The fusion protein of claim 7 comprising a polypeptide comprising an amino acid sequence having at least 80% identity to the amino acid sequence of SEQ ID NO:8, wherein the degron is capable of promoting degradation of the polypeptide of interest and the protease is capable of cleaving the fusion protein at the cleavage site.

9. The fusion protein of claim 7 comprising a polypeptide comprising an amino acid sequence having at least 80% identity to the amino acid sequence of SEQ ID NO:8, wherein the degron is capable of promoting degradation of the polypeptide of interest and the protease is capable of cleaving the fusion protein at the cleavage site.

10. The fusion protein of claim 7 comprising a polypeptide comprising the amino acid sequence of SEQ ID NO:8.

11. The fusion protein of claim 1, further comprising a targeting sequence.

12. The fusion protein of claim 11, wherein the targeting sequence is selected from the group consisting of a secretory protein signal sequence, a membrane protein signal sequence, a nuclear localization sequence, a nucleolar localization signal sequence, an endoplasmic reticulum localization sequence, a peroxisome localization sequence, a mitochondrial localization sequence, and a protein binding motif sequence.

13. The fusion protein of claim 1, further comprising a tag.

14. The fusion protein of claim 13, wherein the tag is selected from the group consisting of a His-tag, a Strep-tag, a TAP-tag, an S-tag, an SBP-tag, an Arg-tag, a calmodulin-binding peptide tag, a cellulose-binding domain tag, a DsbA tag, a c-myc tag, a glutathione S-transferase tag, a FLAG tag, a HAT-tag, a maltose-binding protein tag, a NusA tag, and a thioredoxin tag.

15. The fusion protein of claim 1, further comprising a detectable label.

16. The fusion protein of claim 15, wherein the detectable label is a fluorescent label, a bioluminescent label, a chemiluminescent label, a colorimetric label, or an isotopic label.

17. The fusion protein of claim 16, wherein the detectable label is a fluorescent protein or a bioluminescent protein.

18. The fusion protein of claim 1, wherein the polypeptide of interest is selected from the group consisting of a membrane protein, a receptor, a hormone, a transport protein, a transcription factor, a cytoskeletal protein, an extracellular matrix protein, a signal-transduction protein, and an enzyme.

19. The fusion protein of claim 1, wherein the polypeptide of interest comprises a biologically active domain of a protein.

20. The fusion protein of claim 19, wherein the biologically active domain is a catalytic domain, a ligand binding domain, or a protein-protein interaction domain.

21. An isolated polynucleotide encoding the fusion protein of claim 1.

22. A recombinant polynucleotide comprising the polynucleotide of claim 21 operably linked to a promoter.

23. The recombinant polynucleotide of claim 22, wherein the promoter is an endogenous promoter or exogenous promoter.

24. The recombinant polynucleotide of claim 22 comprising a polynucleotide selected from the group consisting of:

a) a polynucleotide encoding a fusion protein comprising a sequence selected from the group consisting of SEQ ID NO:7 and SEQ ID NO:8; and
b) a polynucleotide encoding a fusion protein comprising a sequence at least 80% identical to a sequence selected from the group consisting of SEQ ID NO:7 and SEQ, ID NO:8, wherein the degron is capable of promoting degradation of the polypeptide of interest, and the protease is capable of cleaving the fusion protein at a cleavage site.

25. The recombinant polynucleotide of claim 22, further comprising a multiple cloning site.

26. The recombinant polynucleotide of claim 22, further comprising a nucleotide sequence encoding a tag, a detectable label, a targeting sequence, or a linker.

27. The recombinant polynucleotide of claim 26, wherein the detectable label is a fluorescent protein or a bioluminescent protein.

28. A host cell transformed with the recombinant polynucleotide of claim 22.

29. The host cell of claim 28, wherein the host cell is a eukaryotic cell.

30. An organoid comprising the host cell of claim 28.

31. A kit comprising the recombinant polynucleotide of claim 22.

32. A kit comprising the host cell of claim 29.

33. A method for producing a fusion protein, the method comprising:
   a) transforming a host cell with the recombinant polynucleotide of claim 22;
   b) culturing the transformed host cell under conditions whereby the fusion protein is expressed; and
   c) isolating the fusion protein from the host cell.

34. A method of controlling production of a polypeptide of interest, the method comprising:
   a) transforming a host cell with the recombinant polynucleotide of claim 22;
   b) culturing the transformed host cell under conditions whereby the fusion protein is produced; and
   c) contacting the cell with a protease inhibitor that inhibits the protease of the fusion protein when production of the polypeptide of interest is no longer desired.

35. The method of claim 34, further comprising removing the protease inhibitor when resuming production of the polypeptide of interest is desired.

36. The method of claim 34, wherein the protease inhibitor is selected from the group consisting of simeprevir, danoprevir, asunaprevir, ciluprevir, boceprevir, sovaprevir, paritaprevir and telaprevir.

37. A method of measuring turnover of a polypeptide of interest, the method comprising:
   a) introducing the recombinant polynucleotide of claim 22 into a cell;
   b) measuring amounts of the polypeptide of interest in the cell before and after contacting the cell with a protease inhibitor that inhibits the protease of the fusion protein; and
   c) calculating the turnover of the polypeptide of interest based on the amounts of the polypeptide of interest in the cell before and after adding the protease inhibitor.

38. The method of claim 37, wherein the measuring is performed continuously over a period of time.

39. The method of claim 37, wherein the measuring is performed periodically.

40. The method of claim 37, further comprising calculating a half-life of the polypeptide of interest in the cell.

* * * * *

UNITED STATES PATENT AND TRADEMARK OFFICE
CERTIFICATE OF CORRECTION

PATENT NO. : 10,550,379 B2
APPLICATION NO. : 15/737712
DATED : February 4, 2020
INVENTOR(S) : Michael Z. Lin et al.

Page 1 of 1

It is certified that error appears in the above-identified patent and that said Letters Patent is hereby corrected as shown below:

In the Claims

In Claim 1, Column 79, Line 17:
Delete "uncleaned" and replace with --uncleaved--.

Signed and Sealed this
First Day of September, 2020

Andrei Iancu
*Director of the United States Patent and Trademark Office*

SEQUENCE LISTING

```
<160> NUMBER OF SEQ ID NOS: 16

<210> SEQ ID NO 1
<211> LENGTH: 42
<212> TYPE: PRT
<213> ORGANISM: Artificial Sequence
<220> FEATURE:
<223> OTHER INFORMATION: Degron

<400> SEQUENCE: 1

Pro Ile Thr Lys Ile Asp Thr Lys Tyr Ile Met Thr Cys Met Ser Ala
1               5                   10                  15

Asp Leu Glu Val Val Thr Ser Thr Trp Val Leu Val Gly Gly Val Leu
            20                  25                  30

Ala Ala Leu Ala Ala Tyr Cys Leu Ser Thr
        35                  40

<210> SEQ ID NO 2
<211> LENGTH: 10
<212> TYPE: PRT
<213> ORGANISM: Artificial Sequence
<220> FEATURE:
<223> OTHER INFORMATION: HCV NS4A/4B protease cleavage site

<400> SEQUENCE: 2

Asp Glu Met Glu Glu Cys Ser Gln His Leu
1               5                   10
```

<210> SEQ ID NO 3
<211> LENGTH: 9
<212> TYPE: PRT
<213> ORGANISM: Artificial Sequence
<220> FEATURE:
<223> OTHER INFORMATION: HCV NS5A/5B protease cleavage site

<400> SEQUENCE: 3

Glu Asp Val Val Pro Cys Ser Met Gly
1               5

<210> SEQ ID NO 4
<211> LENGTH: 186
<212> TYPE: PRT
<213> ORGANISM: Hepatitis C virus

<400> SEQUENCE: 4

Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
                20                  25                  30

Val Gln Ile Val Ser Thr Ala Thr Gln Thr Phe Leu Ala Thr Cys Ile
            35                  40                  45

Asn Gly Val Cys Trp Ala Val Tyr His Gly Ala Gly Thr Arg Thr Ile
    50                  55                  60

Ala Ser Pro Lys Gly Pro Val Ile Gln Met Tyr Thr Asn Val Asp Gln
65                  70                  75                  80

Asp Leu Val Gly Trp Pro Ala Pro Gln Gly Ser Arg Ser Leu Thr Pro
                85                  90                  95

Cys Thr Cys Gly Ser Ser Asp Leu Tyr Leu Val Thr Arg His Ala Asp
                100                 105                 110

Val Ile Pro Val Arg Arg Arg Gly Asp Ser Arg Gly Ser Leu Leu Ser
            115                 120                 125

Pro Arg Pro Ile Ser Tyr Leu Lys Gly Ser Ser Gly Gly Pro Leu Leu
    130                 135                 140

Cys Pro Ala Gly His Ala Val Gly Leu Phe Arg Ala Ala Val Cys Thr
145                 150                 155                 160

Arg Gly Val Ala Lys Ala Val Asp Phe Ile Pro Val Glu Asn Leu Glu
                165                 170                 175

Thr Thr Met Arg Ser Pro Val Phe Thr Asp
                180                 185

<210> SEQ ID NO 5
<211> LENGTH: 33
<212> TYPE: PRT
<213> ORGANISM: Artificial Sequence
<220> FEATURE:
<223> OTHER INFORMATION: NS3 helicase domain with deletion

<400> SEQUENCE: 5

Asn Ser Ser Pro Pro Ala Val Thr Leu Thr His Pro Ile Thr Lys Ile
1               5                   10                  15

Asp Thr Lys Tyr Ile Met Thr Cys Met Ser Ala Asp Leu Glu Val Val
                20                  25                  30

Thr

<210> SEQ ID NO 6
<211> LENGTH: 45

<212> TYPE: PRT
<213> ORGANISM: Hepatitis C virus

<400> SEQUENCE: 6

```
Ser Thr Trp Val Leu Val Gly Gly Val Leu Ala Ala Leu Ala Ala Tyr
1               5                   10                  15

Cys Leu Ser Thr Gly Cys Val Val Ile Val Gly Arg Ile Val Leu Ser
            20                  25                  30

Gly Lys Pro Ala Ile Ile Pro Asp Arg Glu Val Leu Tyr
        35                  40                  45
```

<210> SEQ ID NO 7
<211> LENGTH: 304
<212> TYPE: PRT
<213> ORGANISM: Artificial Sequence
<220> FEATURE:
<223> OTHER INFORMATION: C-terminal SMASh tag with NS4A/4B protease
      cleavage site

<400> SEQUENCE: 7

```
Asp Glu Met Glu Glu Cys Ser Gln His Leu Pro Gly Ala Gly Ser Ser
1               5                   10                  15

Gly Asp Ile Met Asp Tyr Lys Asp Asp Asp Lys Gly Ser Ser Gly
            20                  25                  30

Thr Gly Ser Gly Ser Gly Thr Ser Ala Pro Ile Thr Ala Tyr Ala Gln
            35                  40                  45

Gln Thr Arg Gly Leu Leu Gly Cys Ile Ile Thr Ser Leu Thr Gly Arg
        50                  55                  60

Asp Lys Asn Gln Val Glu Gly Glu Val Gln Ile Val Ser Thr Ala Thr
65                  70                  75                  80

Gln Thr Phe Leu Ala Thr Cys Ile Asn Gly Val Cys Trp Ala Val Tyr
                85                  90                  95

His Gly Ala Gly Thr Arg Thr Ile Ala Ser Pro Lys Gly Pro Val Ile
            100                 105                 110

Gln Met Tyr Thr Asn Val Asp Gln Asp Leu Val Gly Trp Pro Ala Pro
        115                 120                 125

Gln Gly Ser Arg Ser Leu Thr Pro Cys Thr Cys Gly Ser Ser Asp Leu
    130                 135                 140

Tyr Leu Val Thr Arg His Ala Asp Val Ile Pro Val Arg Arg Arg Gly
145                 150                 155                 160

Asp Ser Arg Gly Ser Leu Leu Ser Pro Arg Pro Ile Ser Tyr Leu Lys
                165                 170                 175

Gly Ser Ser Gly Gly Pro Leu Leu Cys Pro Ala Gly His Ala Val Gly
            180                 185                 190

Leu Phe Arg Ala Ala Val Cys Thr Arg Gly Val Ala Lys Ala Val Asp
        195                 200                 205

Phe Ile Pro Val Glu Asn Leu Glu Thr Thr Met Arg Ser Pro Val Phe
    210                 215                 220

Thr Asp Asn Ser Ser Pro Pro Ala Val Thr Leu Thr His Pro Ile Thr
225                 230                 235                 240

Lys Ile Asp Thr Lys Tyr Ile Met Thr Cys Met Ser Ala Asp Leu Glu
                245                 250                 255

Val Val Thr Ser Thr Trp Val Leu Val Gly Gly Val Leu Ala Ala Leu
            260                 265                 270

Ala Ala Tyr Cys Leu Ser Thr Gly Cys Val Val Ile Val Gly Arg Ile
        275                 280                 285
```

```
Val Leu Ser Gly Lys Pro Ala Ile Ile Pro Asp Arg Glu Val Leu Tyr
    290                 295                 300

<210> SEQ ID NO 8
<211> LENGTH: 303
<212> TYPE: PRT
<213> ORGANISM: Artificial Sequence
<220> FEATURE:
<223> OTHER INFORMATION: N-terminal SMASh tag with NS5A/5B protease
      cleavage site

<400> SEQUENCE: 8

Met Asp Tyr Lys Asp Asp Asp Lys Gly Ser Ser Gly Thr Gly Ser
1               5                   10                  15

Gly Ser Gly Thr Ser Ala Pro Ile Thr Ala Tyr Ala Gln Gln Thr Arg
                20                  25                  30

Gly Leu Leu Gly Cys Ile Ile Thr Ser Leu Thr Gly Arg Asp Lys Asn
            35                  40                  45

Gln Val Glu Gly Glu Val Gln Ile Val Ser Thr Ala Thr Gln Thr Phe
        50                  55                  60

Leu Ala Thr Cys Ile Asn Gly Val Cys Trp Ala Val Tyr His Gly Ala
65                  70                  75                  80

Gly Thr Arg Thr Ile Ala Ser Pro Lys Gly Pro Val Ile Gln Met Tyr
                85                  90                  95

Thr Asn Val Asp Gln Asp Leu Val Gly Trp Pro Ala Pro Gln Gly Ser
            100                 105                 110

Arg Ser Leu Thr Pro Cys Thr Cys Gly Ser Ser Asp Leu Tyr Leu Val
        115                 120                 125

Thr Arg His Ala Asp Val Ile Pro Val Arg Arg Arg Gly Asp Ser Arg
130                 135                 140

Gly Ser Leu Leu Ser Pro Arg Pro Ile Ser Tyr Leu Lys Gly Ser Ser
145                 150                 155                 160

Gly Gly Pro Leu Leu Cys Pro Ala Gly His Ala Val Gly Leu Phe Arg
                165                 170                 175

Ala Ala Val Cys Thr Arg Gly Val Ala Lys Ala Val Asp Phe Ile Pro
            180                 185                 190

Val Glu Asn Leu Glu Thr Thr Met Arg Ser Pro Val Phe Thr Asp Asn
        195                 200                 205

Ser Ser Pro Pro Ala Val Thr Leu Thr His Pro Ile Thr Lys Ile Asp
    210                 215                 220

Thr Lys Tyr Ile Met Thr Cys Met Ser Ala Asp Leu Glu Val Val Thr
225                 230                 235                 240

Ser Thr Trp Val Leu Val Gly Gly Val Leu Ala Ala Leu Ala Ala Tyr
                245                 250                 255

Cys Leu Ser Thr Gly Cys Val Val Ile Val Gly Arg Ile Val Leu Ser
            260                 265                 270

Gly Lys Pro Ala Gly Ser Ser Gly Ser Ser Ile Ile Pro Asp Arg Glu
        275                 280                 285

Val Leu Tyr Gln Glu Phe Glu Asp Val Val Pro Cys Ser Met Gly
    290                 295                 300

<210> SEQ ID NO 9
<211> LENGTH: 20722
<212> TYPE: DNA
<213> ORGANISM: Artificial Sequence
<220> FEATURE:
<223> OTHER INFORMATION: MeV-EGFP-P-SMASh plasmid
```

<400> SEQUENCE: 9

```
gttgtaaaac gacggccagt gaattgtaat acgactcact ataaccaaac aaagttgggt      60
aaggatagtt caatcaatga tcatcttcta gtgcacttag gattcaagat cctattatca     120
gggacaagag caggattagg gatatcccga cgcgtacgcc accatggtga gcaagggcga     180
ggagctgttc accggggtgg tgcccatcct ggtcgagctg gacggcgacg taaacggcca     240
caagttcagc gtgtccggcg agggcgaggg cgatgccacc tacggcaagc tgaccctgaa     300
gttcatctgc accaccggca agctgcccgt gcccctggcc cccctcgtga ccaccctgac     360
ctacggcgtg cagtgcttca gccgctaccc cgaccacatg aagcagcacg acttcttcaa     420
gtccgccatg cccgaaggct acgtccagga gcgcaccatc ttcttcaagg acgacggcaa     480
ctacaagacc cgcgccgagg tgaagttcga gggcgacacc ctggtgaacc gcatcgagct     540
gaagggcatc gacttcaagg aggacggcaa catcctgggg cacaagctgg agtacaacta     600
caacagccac aacgtctata tcatggccga caagcagaag aacggcatca aggtgaactt     660
caagatccgc cacaacatcg aggacggcag cgtgcagctc gccgaccact accagcagaa     720
cacccccatc ggcgacggcc ccgtgctgct gcccgacaac cactacctga gcacccagtc     780
cgccctgagc aaagacccca acgagaagcg cgatcacatg gtcctgctgg agttcgtgac     840
cgccgccggg atcactctcg gcatggacga gctgtacaag tagactgacg tctcgcgatc     900
gcgtccgcct accctccatc attgttataa aaaacttagg aaccaggtcc acacagccgc     960
cagcccatca accatccact cccacgattg gagatatccg agatggccac acttttaagg    1020
agcttagcat tgttcaaaag aaacaaggac aaaccaccca ttacatcagg atccggtgga    1080
gccatcagag gaatcaaaca cattattata gtaccaatcc ctggagattc ctcaattacc    1140
actcgatcca gacttctgga ccggttggtc aggttaattg gaaacccgga tgtgagcggg    1200
cccaaactaa caggggcact aataggtata ttatccttat tgtggagtc tccaggtcaa    1260
ttgattcaga ggatcaccga tgaccctgac gttagcataa ggctgttaga ggttgtccag    1320
agtgaccagt cacaatctgg ccttaccttc gcatcaagag gtaccaacat ggaggatgag    1380
gcggaccaat acttttcaca tgatgatcca attagtagtg atcaatccag gttcggatgg    1440
ttcgagaaca aggaaatctc agatattgaa gtgcaagacc ctgagggatt caacatgatt    1500
ctgggtacca tcctagccca aatttgggtc ttgctcgcaa aggcggttac ggccccagac    1560
acggcagctg attcggagct aagaaggtgg ataaagtaca cccaacaaag aagggtagtt    1620
ggtgaattta gattggagag aaaatggttg gatgtggtga ggaacaggat tgccgaggac    1680
ctctccttac gccgattcat ggtcgctcta atcctggaca tcaagagaac acccggaaac    1740
aaacccagga ttgctgaaat gatatgtgac attgatacat atatcgtaga ggcaggatta    1800
gccagttttta tcctgactat taagtttggg atagaaacta tgtatcctgc tcttggactg    1860
catgaatttg ctggtgagtt atccacactt gagtccttga tgaacctta ccagcaaatg    1920
ggggaaactg caccctacat ggtaatcctg gagaactcaa ttcagaacaa gttcagtgca    1980
ggatcatacc ctctgctctg gagctatgcc atgggagtag gagtggaact tgaaaactcc    2040
atgggaggtt tgaactttgg ccgatcttac tttgatccag catattttag attagggcaa    2100
gagatggtaa ggaggtcagc tggaaaggtc agttccacat tggcatctga actcggtatc    2160
actgccgagg atgcaaggct tgtttcagag attgcaatgc atactactga ggacaagatc    2220
agtagagcgg ttggacccag acaagcccaa gtatcatttc tacacggtga tcaaagtgag    2280
aatgagctac cgagattggg gggcaaggaa gataggaggg tcaaacagag tcgaggagaa    2340
```

```
gccagggaga gctacagaga aaccgggccc agcagagcaa gtgatgcgag agctgcccat    2400
cttccaaccg gcacacccct agacattgac actgcatcgg agtccagcca agatccgcag    2460
gacagtcgaa ggtcagctga cgccctgctt aggctgcaag ccatggcagg aatctcggaa    2520
gaacaaggct cagacacgga caccCCtata gtgtacaatg acagaaatct tctagactag    2580
gtgcgagagg ccgaggacca gaacaacatc cgcctaccct ccatcattgt tataaaaaac    2640
ttaggaacca ggtccacaca gccgccagcc catcaaccat ccactcccac gattggagca    2700
gatggcagaa gagcaggcac gccatgtcaa aaacggactg gaatgcatcc gggctctcaa    2760
ggccgagccc atcggctcac tggccatcga ggaagctatg gcagcatggt cagaaatatc    2820
agacaaccca ggacaggagc gagccacctg cagggaagag aaggcaggca gttcgggtct    2880
cagcaaacca tgcctctcag caattggatc aactgaaggc ggtgcacctc gcatccgcgg    2940
tcagggacct ggagagagcg atgacgacgc tgaaactttg gaatccccc caagaaatct    3000 ccaggcatca agcactgggc tacagtgtca ttatgtttat gatcacagcg gtgaagcggt    3060
taagggaatc caagatgctg actctatcat ggttcaatca ggccttgatg gtgatagcac    3120
cctctcagga ggagacaatg aatctgaaaa cagcgatgtg gatattggcg aacctgatac    3180
cgagggatat gctatcactg accggggatc tgctcccatc tctatggggt tcagggcttc    3240
tgatgttgaa actgcagaag gaggggagat ccacgagctc ctgagactcc aatccagagg    3300
caacaacttt ccgaagcttg gaaaaactct caatgttcct ccgcccccgg accccggtag    3360
ggccagcact tccgggacac ccattaaaaa gggcacagac gcgagattag cctcatttgg    3420
aacggagatc gcgtcttcat tgacaggtgg tgcaacccaa tgtgctcgaa agtcaccctc    3480
ggaaccatca gggccaggtg cacctgcggg aacgtcccc gagtgtgtga gcaatgccgc    3540
actgatacag gagtggacac ccgaatctgg caccacaatc tccccgagat cccagaataa    3600
tgaagaaggg ggagaccatt atgatgatga gctgttctct gatgtccaag atattaaaac    3660
agccttggcc aaaatacacg aggataatca gaagataatc tccaagctag aatcactgct    3720
gttattgaag ggagaagttg agtcaattaa gaagcagatc aacaggcaaa atatcagcat    3780
atccaccctg gaaggacacc tctcaagcat catgatcgcc attcctggac ttgggaagga    3840
tcccaacgac cccactgcag atgtcgaaat caatcccgac ttgaaaccca tcataggcag    3900
agattcaggc cgagcactgg ccgaagttct caagaaaccc gttgccagcc gacaactcca    3960
aggaatgaca aatggacgga ccagttccag aggacagctg ctgaaggaat ttcagctaaa    4020
gccgatcggg aaaagatga gctcagccgt cgggtttgtt cctgacaccg gccctgcatc    4080
acgcagtgta atccgctcca ttataaaatc cagccggcta gaggaggatc ggaagcgtta    4140
cctgatgact ctccttgatg atatcaaagg agccaatgat cttgccaagt tccaccagat    4200
gctggtgaag ataataatga aggacgaaat ggaggaatgt tcacagcact acccggcgc    4260 cggcagtagt ggcgatatca tggattacaa ggatgacgac gataagggct cttccgggac    4320
aggctccgga tccggcacta gtgcgcccat cacggcgtac gcccagcaga cgagaggcct    4380
cctagggtgt ataatcacca gcctgactgg ccgggacaaa aaccaagtgg agggtgaggt    4440
ccagatcgtg tcaactgcta cccaaaacctt cctggcaacg tgcatcaatg gggtatgctg    4500
ggcagtctac cacggggccg gaacgaggac catcgcatca cccaagggtc ctgtcatcca    4560
gatgtatacc aatgtggacc aagaccttgt gggctggccc gctcctcaag ttcccgctc    4620 attgacaccc tgtacctgcg gctcctcgga cctttacctg gtcacgaggc acgccgatgt    4680
```

```
cattcccgtg cgccggcgag gtgatagcag gggtagcctg ctttcgcccc ggcccatttc    4740
ctacttgaaa ggctcctcgg ggggtccgct gttgtgcccc gcgggacacg ccgtgggcct    4800
attcagggcc gcggtgtgca cccgtggagt ggctaaagcg gtggacttta tccctgtgga    4860
gaacctagag acaaccatga gatccccggt gttcacggac aactcctctc caccagcagt    4920
caccctgacg cacccaatca ccaaaatcga taccaaatac atcatgacat gcatgtcggc    4980
cgacctggag gtcgtcacga gcacctgggt gctcgttggc ggcgtcctgg ctgctctggc    5040
cgcgtattgc ctgtcaacag gctgcgtggt catagtgggc aggatcgtct tgtccgggaa    5100
gccggcaatt atacctgaca gggaggttct ctaccaggag ttcggcgcgc cttgactaca    5160
gctcaactta cctgccaacc ccatgccagt cgacccaact agtacaacct aaatccatta    5220
taaaaaactt aggagcaaag tgattgcctc caagttcca caatgacaga gatctacgac     5280
ttcgacaagt cggcatggga catcaaaggg tcgatcgctc cgatacaacc caccacctac    5340
agtgatggca ggctggtgcc ccaggtcaga gtcatagatc ctggtctagg cgacaggaag    5400
gatgaatgct ttatgtacat gtttctgctg ggggttgttg aggacagcga ttccctaggg    5460
cctccaatcg ggcgagcatt tgggtccctg cccttaggtg ttggcagatc cacagcaaag    5520
cccgaaaaac tcctcaaaga ggccactgag cttgacatag ttgttagacg tacagcaggg    5580
ctcaatgaaa aactggtgtt ctacaacaac accccactaa ctctcctcac accttggaga    5640
aaggtcctaa caacagggag tgtcttcaac gcaaaccaag tgtgcaatgc ggttaatctg    5700
ataccgctcg atacccgca gaggttccgt gttgtttata tgagcatcac ccgtctttcg     5760
gataacgggt attacaccgt tcctggaaga atgctggaat tcagatcggt caatgcagtg    5820
gccttcaacc tgctggtgac ccttaggatt gacaaggcga taggccctgg gaagatcatc    5880
gacaatacag agcaacttcc tgaggcaaca tttatggtcc acatcgggaa cttcaggaga    5940
aagaagagtg aagtctactc tgccgattat tgcaaaatga aaatcgaaaa gatgggcctg    6000 gttttttgcac ttggtgggat aggggggcacc agtcttcaca ttagaagcac aggcaaaatg    6060
agcaagactc tccatgcaca actcgggttc aagaagacct tatgttaccc gctgatggat    6120
atcaatgaag accttaatcg attactctgg aggagcagat gcaagatagt aagaatccag    6180
gcagttttgc agccatcagt tcctcaagaa ttccgcattt acgacgacgt gatcataaat    6240
gatgaccaag gactattcaa agttctgtag accgtagtgc ccagcaatgc ccgaaaacga    6300
cccccctcac aatgacagcc agaaggcccg gacaaaaaag ccccctccga aagactccac    6360
ggaccaagcg agaggccagc cagcagccga cggcaagcgc gaacaccagg cggccccagc    6420
acagaacagc cctgacacaa ggccaccacc agccaccccca atctgcatcc tcctcgtggg    6480 accccgagg accaacccc aaggctgccc ccgatccaaa ccaccaaccg catccccacc      6540
accccgggga agaaacccc cagcaattgg aaggcccctc ccctcttcc tcaacacaag      6600 aactccacaa ccgaaccgca caagcgaccg aggtgaccca accgcaggca tccgactccc    6660
tagacagatc ctctctcccc ggcaaactaa acaaaactta gggccaagga acatacacac    6720
ccaacagaac ccagaccccg gcccacggcg ccgcgccccc aaccccgac aaccagaggg     6780 agcccccaac caatcccgcc ggctcccccg gtgcccacag gcagggacac caaccccga    6840 acagacccag cacccaacca tcgacaatcc aagacggggg ggccccccca aaaaaggcc     6900 cccaggggcc gacagccagc accgcgagga gcccaccca cccacacac gaccacggca     6960 accaaaccag aacccagacc accctgggcc accagctccc agactcggcc atcccccgc    7020 agaaaggaaa ggccacaacc cgcgcacccc agccccgatc cggcggggag ccacccaacc   7080
```

```
cgaaccagca cccaagagcg atccccgaag gaccccgaa  ccgcaaagga catcagtatc   7140
ccacagcctc tccaagtccc ccggtctcct cctcttctcg aagggaccaa aagatcaatc   7200
caccacaccc gacgacactc aactcccac  ccctaaagga gacaccggga atcccagaat   7260
caagactcat ccaatgtcca tcatgggtct caaggtgaac gtctctgcca tattcatggc   7320
agtactgtta actctccaaa cacccaccgg tcaaatccat tggggcaatc tctctaagat   7380
aggggtggta ggaataggaa gtgcaagcta caaagttatg actcgttcca gccatcaatc   7440
attagtcata aaattaatgc ccaatataac tctcctcaat aactgcacga gggtagagat   7500
tgcagaatac aggagactac tgagaacagt tttggaacca attagagatg cacttaatgc   7560
aatgacccag aatataagac cggttcagag tgtagcttca agtaggagac acaagagatt   7620
tgcgggagta gtcctggcag gtgcggccct aggcgttgcc acagctgctc agataacagc   7680
cggcattgca cttcaccagt ccatgctgaa ctctcaagcc atcgacaatc tgagagcgag   7740
cctggaaact actaatcagg caattgaggc aatcagacaa gcaggcagg  agtgatatt    7800 ggctgttcag ggtgtccaag actacatcaa taatgagctg ataccgtcta tgaaccaact   7860
atcttgtgat ttaatcggcc agaagctcgg gctcaaattg ctcagatact atacagaaat   7920
cctgtcatta tttggcccca gcttacggga ccccatatct gcggagatat ctatccaggc   7980
tttgagctat gcgcttggag gagacatcaa taaggtgtta gaaaagctcg gatacagtgg   8040
aggtgattta ctgggcatct tagagagcag aggaataaag gcccggataa ctcacgtcga   8100
cacagagtcc tacttcattg tcctcagtat agcctatccg acgctgtccg agattaaggg   8160
ggtgattgtc caccggctag aggggtctc  gtacaacata ggctctcaag agtggtatac   8220
cactgtgccc aagtatgttg caacccaagg gtaccttatc tcgaattttg atgagtcatc   8280 gtgtacttc  atgccagagg ggactgtgtg cagccaaaat gccttgtacc cgatgagtcc   8340
tctgctccaa gaatgcctcc gggggtccac caagtcctgt gctcgtacac tcgtatccgg   8400
gtcttttggg aaccggttca tttatcaca  agggaaccta atagccaatt gtgcatcaat   8460
cctttgcaag tgttacacaa caggaacgat cattaatcaa gaccctgaca agatcctaac   8520
atacattgct gccgatcact gcccggtagt cgaggtgaac ggcgtgacca tccaagtcgg   8580
gagcaggagg tatccagacg ctgtgtactt gcacagaatt gacctcggtc ctcccatatc   8640
attggagagg ttggacgtag ggacaaatct ggggaatgca attgctaagt tggaggatgc   8700
caaggaattg ttggagtcat cggaccagat attgaggagt atgaaaggtt tatcgagcac   8760
tagcatagtc tacatcctga ttgcagtgtg tcttggaggg ttgatagga  tccccgcttt   8820 aatatgttgc tgcaggggc  gttgtaacaa aaagggagaa caagttggta tgtcaagacc   8880
aggcctaaag cctgatctta cgggaacatc aaaatcctat gtaaggtcgc tctgatcctc   8940
tacaactctt gaaacacaaa tgtcccacaa gtctcctctt cgtcatcaag caaccaccgc   9000
acccagcatc aagcccacct gaaattatct ccggtttcca agcggaagaa caatatcggt   9060
agttaattaa aacttagggt gcaagatcat ccacaatgtc accacaacga gaccggataa   9120
atgccttcta caaagataac ccccatccca agggaagtag gatagtcatt aacagagaac   9180
atcttatgat tgatagacct tatgttttgc tggctgttct gtttgtcatg tttctgagct   9240
tgatcgggtt gctagccatt gcaggcatta gacttcatcg ggcagccatc tacaccgcag   9300
agatccataa aagcctcagc accaatctag atgtaactaa ctcaatcgag catcaggtca   9360
aggacgtgct gacaccactc ttcaaaatca tcggtgatga agtgggcctg aggacacctc   9420
```

```
agagattcac tgacctagtg aaattcatct ctgacaagat taaattcctt aatccggata   9480
gggagtacga cttcagagat ctcacttggt gtatcaaccc gccagagaga atcaaattgg   9540
attatgatca atactgtgca gatgtggctg ctgaagagct catgaatgca ttggtgaact   9600
caactctact ggagaccaga acaaccaatc agttcctagc tgtctcaaag ggaaactgct   9660
cagggcccac tacaatcaga ggtcaattct caaacatgtc gctgtccctg ttagacttgt   9720
atttaggtcg aggttacaat gtgtcatcta tagtcactat gacatcccag gaatgtatg    9780 ggggaactta cctagtggaa aagcctaatc tgagcagcaa aaggtcagag ttgtcacaac   9840
tgagcatgta ccgagtgttt gaagtaggtg ttatcagaaa tccgggtttg ggggctccgg   9900
tgttccatat gacaaactat cttgagcaac cagtcagtaa tgatctcagc aactgtatgg   9960
tggctttggg ggagctcaaa ctcgcagccc tttgtcacgg ggaagattct atcacaattc  10020
cctatcaggg atcagggaaa ggtgtcagct tccagctcgt caagctaggt gtctggaaat  10080
ccccaaccga catgcaatcc tgggtcccct tatcaacgga tgatccagtg atagacaggc  10140
tttacctctc atctcacaga ggtgttatcg ctgacaacca agcaaaatgg gctgtcccga  10200
caacacgaac agatgacaag ttgcgaatgg agacatgctt ccaacaggcg tgtaagggta  10260
aaatccaagc actctgcgag aatcccgagt gggcaccatt gaaggataac aggattcctt  10320
catacggggt cttgtctgtt gatctgagtc tgacagttga gcttaaaatc aaaattgctt  10380
cgggattcgg gccattgatc acacacggtt cagggatgga cctatacaaa tccaaccaca  10440
acaatgtgta ttggctgact atcccgccaa tgaagaacct agccttaggt gtaatcaaca  10500
cattggagtg gataccgaga ttcaaggtta gtccctacct cttcactgtc ccaattaagg  10560
aagcaggcgg agactgccat gccccaacat acctacctgc ggaggtggat ggtgatgtca  10620
aactcagttc caatctggtg attctacctg gtcaagatct ccaatatgtt ttggcaacct  10680
acgatacttc cagggttgaa catgctgtgg tttattacgt ttacagccca agccgctcat  10740
tttcttactt ttatccttt aggttgccta taaaggggt ccccatcgaa ttacaagtgg    10800
aatgcttcac atgggaccaa aaactctggt gccgtcactt ctgtgtgctt gcggactcag  10860
aatctggtgg acatatcact cactctggga tggtgggcat gggagtcagc tgcacagtca  10920
cccgggaaga tggaaccaat cgcagatagg gctgctagtg aaccaatcac atgatgtcac  10980
ccagacatca ggcatacccca ctagtgtgaa atagacatca gaattaagaa aaacgtaggg  11040
tccaagtggt tccccgttat ggactcgcta tctgtcaacc agatcttata ccctgaagtt  11100
cacctagata gcccgatagt taccaataag atagtagcca tcctggagta tgctcgagtc  11160
cctcacgctt acagcctgga ggaccctaca ctgtgtcaga acatcaagca ccgcctaaaa  11220
aacggatttt ccaaccaaat gattataaac aatgtggaag ttgggaatgt catcaagtcc  11280
aagcttagga gttatccggc ccactctcat attccatatc caaattgtaa tcaggattta  11340
tttaacatag aagacaaaga gtcaacgagg aagatccgtg aactcctcaa aaaggggaat  11400
tcgctgtact ccaaagtcag tgataaggtt ttccaatgct taagggacac taactcacgg  11460
cttggcctag ctccgaatt gagggaggac atcaaggaga aagttattaa cttgggagtt  11520
tacatgcaca gctcccagtg gtttgagccc tttctgtttt ggtttacagt caagactgag  11580
atgaggtcag tgattaaatc acaaacccat acttgccata ggaggagaca cacacctgta  11640
ttcttcactg gtagttcagt tgagttgcta atctctcgtg accttgttgc tataatcagt  11700
aaagagtctc aacatgtata ttacctgaca tttgaactgg ttttgatgta ttgtgatgtc  11760
atagagggga ggttaatgac agagaccgct atgactattg atgctaggta tacagagctt  11820
```

```
ctaggaagag tcagatacat gtggaaactg atagatggtt tcttccctgc actcgggaat   11880
ccaacttatc aaattgtagc catgctggag cctctttcac ttgcttacct gcagctgagg   11940
gatataacag tagaactcag aggtgctttc cttaaccact gctttactga aatacatgat   12000
gttcttgacc aaaacgggtt ttctgatgaa ggtacttatc atgagttaat tgaagctcta   12060
gattacattt tcataactga tgacatacat ctgacagggg agattttctc attttttcaga   12120 agtttcggcc acccccagact tgaagcagta acggctgctg aaaatgttag gaaatacatg   12180
aatcagccta agtcattgt gtatgagact ctgatgaaag gtcatgccat attttgtgga   12240
atcataatca acggctatcg tgacaggcac ggaggcagtt ggccaccgct gaccctcccc   12300
ctgcatgctg cagacacaat ccggaatgct caagcttcag gtgatgggtt aacacatgag   12360
cagtgcgttg ataactggaa atcttttgct ggagtgaaat ttggctgctt tatgcctctt   12420
agcctggata gtgatctgac aatgtaccta aaggacaagg cacttgctgc tctccaaagg   12480
gaatgggatt cagtttaccc gaaagagttc ctgcgttacg accctcccaa gggaaccggg   12540
tcacggaggc ttgtagatgt tttccttaat gattcgagct tgacccata tgatgtgata   12600 atgtatgttg taagtggagc ttacctccat gaccctgagt caacctgtc ttacagcctg   12660 aaagaaaagg agatcaagga aacaggtaga cttttgcta aaatgactta caaatgagg   12720 gcatgccaag tgattgctga aaatctaatc tcaaacggga ttggcaaata ttttaaggac   12780
aatgggatgg ccaaggatga gcacgatttg actaaggcac tccacactct agctgtctca   12840
ggagtcccca aagatctcaa agaaagtcac agggggggggc cagtcttaaa aacctactcc   12900
cgaagcccag tccacacaag taccaggaac gtgagagcag caaaagggtt tatagggttc   12960
cctcaagtaa ttcggcagga ccaagacact gatcatccgg agaatatgga agcttacgag   13020
acagtcagtg catttatcac gactgatctc aagaagtact gccttaattg gagatatgag   13080
accatcagct tgtttgcaca gaggctaaat gagatttacg gattgccctc attttttccag   13140 tggctgcata agaggcttga gacctctgtc ctgtatgtaa gtgaccctca ttgcccccc    13200 gaccttgacg cccatatccc gttatataaa gtccccaatg atcaaatctt cattaagtac   13260
cctatgggag gtatagaagg gtattgtcag aagctgtgga ccatcagcac cattccctat   13320
ctatacctgg ctgcttatga gagcggagta aggattgctt cgttagtgca aggggacaat   13380
cagaccatag ccgtaacaaa aagggtaccc agcacatggc cctacaacct taagaaacgg   13440
gaagctgcta gagtaactag agattacttt gtaattctta ggcaaaggct acatgatatt   13500
ggccatcacc tcaaggcaaa tgagacaatt gtttcatcac attttttttgt ctattcaaaa   13560 ggaatatatt atgatgggct acttgtgtcc caatcactca agagcatcgc aagatgtgta   13620
ttctggtcag agactatagt tgatgaaaca agggcagcat gcagtaatat tgctacaaca   13680
atggctaaaa gcatcgagag aggttatgac cgttaccttg catattccct gaacgtccta   13740
aaagtgatac agcaaattct gatctctctt ggcttcacaa tcaattcaac catgacccgg   13800
gatgtagtca taccccctcct cacaaacaac gacctcttaa taaggatggc actgttgccc   13860
gctcctattg gggggatgaa ttatctgaat atgagcaggc tgtttgtcag aaacatcggt   13920
gatccagtaa catcatcaat tgctgatctc aagagaatga ttctcgcctc actaatgcct   13980
gaagagaccc tccatcaggt aatgacacaa caaccggggg actcttcatt cctagactgg   14040
gctagcgacc cttactcagc aaatcttgta tgtgtccaga gcatcactag actcctcaag   14100
aacataactg caaggtttgt cctgatccat agtccaaacc caatgttaaa aggattattc   14160
```

```
catgatgaca gtaaagaaga ggacgaggga ctggcggcat tcctcatgga caggcatatt    14220
atagtaccta gggcagctca tgaaatcctg gatcatagtg tcacagggggc aagagagtct    14280 attgcaggca tgctggatac cacaaaaggc ttgattcgag ccagcatgag aaggggggt     14340 ttaacctctc gagtgataac cagattgtcc aattatgact atgaacaatt cagagcaggg    14400
atggtgctat tgacaggaag aaagagaaat gtcctcattg acaaagagtc atgttcagtg    14460
cagctggcga gagctctaag aagccatatg tgggcgaggc tagctcgagg acggcctatt    14520
tacggccttg aggtccctga tgtactagaa tctatgcgag gccaccttat tcggcgtcat    14580
gagacatgtg tcatctgcga gtgtggatca gtcaactacg gatggttttt tgtcccctcg    14640
ggttgccaac tggatgatat tgacaaggaa acatcatcct tgagagtccc atatattggt    14700
tctaccactg atgagagaac agacatgaag cttgccttcg taagagcccc aagtcgatcc    14760
ttgcgatctg ctgttagaat agcaacagtg tactcatggg cttacggtga tgatgatagc    14820
tcttggaacg aagcctggtt gttggctagg caaagggcca atgtgagcct ggaggagcta    14880
agggtgatca ctcccatctc aacttcgact aatttagcgc ataggttgag ggatcgtagc    14940
actcaagtga atactcagg tacatcccctt gtccgagtgg cgaggtatac cacaatctcc    15000
aacgacaatc tctcatttgt catatcagat aagaaggttg atactaactt tatataccaa    15060
caaggaatgc ttctagggtt gggtgtttta gaaacattgt ttcgactcga gaaagatacc    15120
ggatcatcta acacggtatt acatcttcac gtcgaaacag attgttgcgt gatcccgatg    15180
atagatcatc ccaggatacc cagctcccgc aagctagagc tgagggcaga gctatgtacc    15240
aacccattga tatatgataa tgcacccttta attgacagat atgcaacaag gctatacacc    15300
cagagccata ggaggcacct tgtggaattt gttacatggt ccacacccca actatatcac    15360 atttttagcta agtccacagc actatctatg attgacctgg taacaaaatt tgagaaggac    15420
catatgaatg aaatttcagc tctcatagggg gatgacgata tcaatagttt cataactgag    15480
tttctgctca tagagccaag attattcact atctacttgg gccagtgtgc ggccatcaat    15540
tgggcatttg atgtacatta tcatagacca tcagggaaat atcagatggg tgagctgttg    15600
tcatcgttcc tttctagaat gagcaaagga gtgtttaagg tgcttgtcaa tgctctaagc    15660
cacccaaaga tctacaagaa attctggcat tgtggtatta tagagcctat ccatggtcct    15720
tcacttgatg ctcaaaactt gcacacaact gtgtgcaaca tggtttacac atgctatatg    15780
acctacctcg acctgttgtt gaatgaagag ttagaagagt tcacatttct cttgtgtgaa    15840
agcgacgagg atgtagtacc ggacagattc gacaacatcc aggcaaaaca cttatgtgtt    15900
ctggcagatt tgtactgtca accagggacc tgcccaccaa ttcaaggtct aagaccggta    15960
gagaaatgtg cagttctaac cgaccatatc aaggcagagg ctatgttatc ccagcagga    16020 tcttcgtgga acataaatcc aattattgta gaccattact catgctccct gacttatctc    16080
cggcgaggat cgatcaaaca gataagattg agagttgatc caggattcat tttcgacgcc    16140
ctcgctgagg taaatgtcag tcagccaaag atcggcagca acaacatctc aaatatgagc    16200
atcaaggctt tcagaccccc acacgatgat gttgcaaaat tgctcaaaga tatcaacaca    16260
agcaagcaca atcttcccat ttcaggggc aatctcgcca attatgaaat ccatgctttc    16320
cgcagaatcg ggttgaactc atctgcttgc tacaaagctg ttgagatatc aacattaatt    16380
aggagatgcc ttgagccagg ggaggacggc ttgttcttgg gtgagggatc gggttctatg    16440
ttgatcactt ataaggagat acttaaacta agcaagtgct tctataatag tggggttccc    16500
gccaattcta gatctggtca aagggaatta gcaccctatc cctccgaagt tggccttgtc    16560
```

```
gaacacagaa tgggagtagg taatattgtc aaagtgctct ttaacgggag gcccgaagtc    16620
acgtgggtag gcagtgtaga ttgcttcaat ttcatagtta gtaatatccc tacctctagt    16680
gtggggttta tccattcaga tatagagacc ttgcctgaca aagatactat agagaagcta    16740
gaggaattgg cagccatctt atcgatggct ctgctcctgg gcaaaatagg atcaatactg    16800
gtgattaagc ttatgccttt cagcggggat tttgttcagg gatttataag ttatgtaggg    16860
tctcattata gagaagtgaa ccttgtatac cctagataca gcaacttcat atctactgaa    16920
tcttatttgg ttatgacaga tctcaaggct aaccggctaa tgaatcctga aaagattaag    16980
cagcagataa ttgaatcatc tgtgaggact tcacctggac ttataggtca catcctatcc    17040
attaagcaac taagctgcat acaagcaatt gtgggagacg cagttagtag aggtgatatc    17100
aatcctactc tgaaaaaact tacacctata gagcaggtgc tgatcaattg cgggttggca    17160
attaacggac ctaagctgtg caaagaattg atccaccatg atgttgcctc agggcaagat    17220
ggattgctta attctatact catcctctac agggagttgg caagattcaa agacaaccaa    17280
agaagtcaac aagggatgtt ccacgcttac cccgtattgg taagtagcag gcaacgagaa    17340
cttatatcta ggatcacccg caaattttgg gggcacattc ttctttactc cgggaacaga    17400
aagttgataa ataagtttat ccagaatctc aagtccggct atctgatact agacttacac    17460
cagaatatct tcgttaagaa tctatccaag tcagagaaac agattattat gacgggggt    17520 ttgaaacgtg agtgggtttt taaggtaaca gtcaaggaga ccaaagaatg gtataagtta    17580
gtcggataca gtgccctgat taaggactaa ttggttgaac tccggaaccc taatcctgcc    17640
ctaggtggtt aggcattatt tgcaatatat taaagaaaac tttgaaaata cgaagtttct    17700
attcccagct ttgtctggtg gccggcatgg tcccagcctc ctcgctgcg ccggctgggc     17760 aacattccga ggggaccgtc ccctcggtaa tggcgaatgg gacgcggccg atccggctgc    17820
taacaaagcc cgaaaggaag ctgagttggc tgctgccacc gctgagcaat aactagcata    17880
accccttggg gcctctaaac gggtcttgag gggttttttg ctgaaaggag gaactatatc    17940
cggatgcggc cgcaggtacc agcttttgtt ccctttagtg agggttaatt tcgagcttgg    18000
cgtaatcatg gtcatagctg tttcctgtgt gaaattgtta tccgctcaca attccacaca    18060
acatacgagc cggaagcata aagtgtaaag cctggggtgc ctaatgagtg agctaactca    18120
cattaattgc gttgcgctca ctgcccgctt tccagtcggg aaacctgtcg tgccagctgc    18180
attaatgaat cggccaacgc gcggggagag gcggtttgcg tattgggcgc tcttccgctt    18240
cctcgctcac tgactcgctg cgctcggtcg ttcggctgcg gcgagcggta tcagctcact    18300
caaaggcggt aatacggtta tccacagaat caggggataa cgcaggaaag aacatgtgag    18360
caaaaggcca gcaaaaggcc aggaaccgta aaaaggccgc gttgctggcg tttttccata    18420
ggctccgccc ccctgacgag catcacaaaa atcgacgctc aagtcagagg tggcgaaacc    18480
cgacaggact ataaagatac caggcgtttc ccctggaag ctccctcgtg cgctctcctg      18540
ttccgaccct gccgcttacc ggatacctgt ccgcctttct cccttcggga agcgtggcgc    18600
tttctcatag ctcacgctgt aggtatctca gttcggtgta ggtcgttcgc tccaagctgg    18660
gctgtgtgca cgaacccccc gttcagcccg accgctgcgc cttatccggt aactatcgtc    18720
ttgagtccaa cccggtaaga cacgacttat cgccactggc agcagccact ggtaacagga    18780
ttagcagagc gaggtatgta ggcggtgcta cagagttctt gaagtggtgg cctaactacg    18840
gctacactag aagaacagta tttggtatct gcgctctgct gaagccagtt accttcggaa    18900
```

-continued

```
aaagagttgg tagctcttga tccggcaaac aaaccaccgc tggtagcggt ggttttttg      18960
tttgcaagca gcagattacg cgcagaaaaa aaggatctca agaagatcct ttgatctttt      19020
ctacggggtc tgacgctcag tggaacgaaa actcacgtta agggattttg gtcatgagat      19080
tatcaaaaag gatcttcacc tagatccttt taaattaaaa atgaagtttt aaatcaatct      19140
aaagtatata tgagtaaact tggtctgaca gttaccaatg cttaatcagt gaggcaccta      19200
tctcagcgat ctgtctattt cgttcatcca tagttgcctg actccccgtc gtgtagataa      19260
ctacgatacg ggagggctta ccatctggcc ccagtgctgc aatgataccg cgagacccac      19320
gctcaccggc tccagattta tcagcaataa accagccagc cggaagggcc gagcgcagaa      19380
gtggtcctgc aactttatcc gcctccatcc agtctattaa ttgttgccgg gaagctagag      19440
taagtagttc gccagttaat agtttgcgca acgttgttgc cattgctaca ggcatcgtgg      19500
tgtcacgctc gtcgtttggt atggcttcat tcagctccgg ttcccaacga tcaaggcgag      19560
ttacatgatc ccccatgttg tgcaaaaaag cggttagctc cttcggtcct ccgatcgttg      19620
tcagaagtaa gttggccgca gtgttatcac tcatggttat ggcagcactg cataattctc      19680
ttactgtcat gccatccgta agatgctttt ctgtgactgg tgagtactca accaagtcat      19740
tctgagaata gtgtatgcgg cgaccgagtt gctcttgccc ggcgtcaata cgggataata      19800
ccgcgccaca tagcagaact ttaaaagtgc tcatcattgg aaaacgttct cggggcgaa       19860
aactctcaag gatcttaccg ctgttgagat ccagttcgat gtaacccact cgtgcaccca      19920
actgatcttc agcatctttt actttcacca gcgtttctgg gtgagcaaaa acaggaaggc      19980
aaaatgccgc aaaaaaggga ataagggcga cacggaaatg ttgaatactc atactcttcc      20040
ttttcaata ttattgaagc atttatcagg gttattgtct catgagcgga tacatatttg       20100
aatgtattta gaaaaataaa caataggggg ttccgcgcac atttccccga aaagtgccac      20160
ctaaattgta agcgttaata ttttgttaaa attcgcgtta aatttttgtt aaatcagctc      20220
attttttaac caataggccg aaatcggcaa aatcccttat aaatcaaaag aatagaccga      20280
gatagggttg agtgttgttc cagtttggaa caagagtcca ctattaaaga acgtggactc      20340
caacgtcaaa gggcgaaaaa ccgtctatca gggcgatggc ccactacgtg aaccatcacc      20400
ctaatcaagt tttttggggt cgaggtgccg taaagcacta aatcggaacc ctaaagggag      20460
cccccgattt agagcttgac ggggaaagcc ggccatttag gccatagggc gctggcaagt      20520
gtagcggtca cgctgcgcgt aaccaccaca cccgccgcac ttaatgcgcc gctacagggc      20580
gcgtcccatt cgccattcag gctgcgcaac tgttgggaag ggcgatcggt gcgggcctct      20640
tcgctattac gccagctggc gaaaggggga tgtgctgcaa ggcgattaag ttgggtaacg      20700
ccagggtttt cccagtcacg ac                                               20722
```

<210> SEQ ID NO 10
<211> LENGTH: 19
<212> TYPE: DNA
<213> ORGANISM: Artificial Sequence
<220> FEATURE:
<223> OTHER INFORMATION: PCR primer 28-F

<400> SEQUENCE: 10
taatctccaa gctagaatc                                                          19

<210> SEQ ID NO 11
<211> LENGTH: 17
<212> TYPE: DNA
<213> ORGANISM: Artificial Sequence

```
<220> FEATURE:
<223> OTHER INFORMATION: PCR primer 35-R

<400> SEQUENCE: 11
agcctgccat cactgta                                                    17

<210> SEQ ID NO 12
<211> LENGTH: 5
<212> TYPE: PRT
<213> ORGANISM: Artificial Sequence
<220> FEATURE:
<223> OTHER INFORMATION: nucleus targeting sequence

<400> SEQUENCE: 12

Lys Lys Lys Arg Lys
1               5

<210> SEQ ID NO 13
<211> LENGTH: 26
<212> TYPE: PRT
<213> ORGANISM: Artificial Sequence
<220> FEATURE:
<223> OTHER INFORMATION: mitochondria targeting sequence

<400> SEQUENCE: 13

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 14
<211> LENGTH: 4
<212> TYPE: PRT
<213> ORGANISM: Artificial Sequence
<220> FEATURE:
<223> OTHER INFORMATION: endoplasmic reticulum targeting sequence

<400> SEQUENCE: 14

Lys Asp Glu Leu
1

<210> SEQ ID NO 15
<211> LENGTH: 4
<212> TYPE: PRT
<213> ORGANISM: Artificial Sequence
<220> FEATURE:
<223> OTHER INFORMATION: plasma membrane targeting sequence
<220> FEATURE:
<221> NAME/KEY: misc_feature
<222> LOCATION: (2)..(3)
<223> OTHER INFORMATION: Xaa is an aliphatic amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 15

Cys Xaa Xaa Xaa
1

<210> SEQ ID NO 16
<211> LENGTH: 4
<212> TYPE: PRT
<213> ORGANISM: Artificial Sequence
<220> FEATURE:
<223> OTHER INFORMATION: plasma membrane targeting sequence
<220> FEATURE:
<221> NAME/KEY: misc_feature
```

-continued

```
<222> LOCATION: (3)..(4)
<223> OTHER INFORMATION: Xaa can be any naturally occurring amino acid

<400> SEQUENCE: 16

Cys Cys Xaa Xaa
1
```